United States Patent
Andjelkovic et al.

(10) Patent No.: US 7,812,028 B2
(45) Date of Patent: Oct. 12, 2010

(54) 3-PYRIDINECARBOXAMIDE DERIVATIVES AS HDL-CHOLESTEROL RAISING AGENTS

(75) Inventors: Mirjana Andjelkovic, Basel (CH); Agnes Benardeau, Saint Louis (FR); Evelyne Chaput, Sierentz (FR); Paul Hebeisen, Basel (CH); Matthias Nettekoven, Grenzach-Wyhlen (DE); Ulrike Obst Sander, Reinach BL (CH); Constantinos G. Panousis, Bottmingen (CH); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/366,692

(22) Filed: Feb. 6, 2009

(65) Prior Publication Data
US 2009/0143409 A1    Jun. 4, 2009

Related U.S. Application Data

(63) Continuation of application No. 11/904,425, filed on Sep. 27, 2007, now abandoned.

(30) Foreign Application Priority Data
Oct. 4, 2006    (EP) .................................. 06121755

(51) Int. Cl.
*A61K 31/4965*    (2006.01)
(52) U.S. Cl. .................. 514/255.06; 546/315
(58) Field of Classification Search ............ 514/255.06; 546/315
See application file for complete search history.

(56) References Cited

U.S. PATENT DOCUMENTS

| | | | |
|---|---|---|---|
| 7,229,999 | B2 | 6/2007 | Hoffmann-La Roche Inc. |
| 2007/0293509 | A1 | 12/2007 | Hebeisen et al. |
| 2008/0070931 | A1 | 3/2008 | Hebeisen et al. |
| 2008/0085905 | A1 | 4/2008 | Dietz et al. |

FOREIGN PATENT DOCUMENTS

| | | |
|---|---|---|
| WO | WO 03/051850 A1 | 6/2003 |
| WO | WO 2004/111033 A1 | 12/2004 |
| WO | WO 2006/106054 | 10/2006 |
| WO | WO 2007/011760 A2 | 1/2007 |
| WO | WO 2007/147746 | 12/2007 |
| WO | WO 2008/031734 | 3/2008 |

OTHER PUBLICATIONS

Jordan, V.C., Nature Reviews: Drug Discovery, 2, 2003, p. 2005.
Dörwald, F. Zaragoza. Side Reactions in Organic Synthesis: A Guide to Successful Synthesis Design, Weinheim: WILEY-VCH Verlag GmbH & Co. KGaA, 2005, Preface.
Belsey, et al., Curr. Med. Res. Opin., 24(09), 2008, pp. 2703-2709.
Gomaraschi, et al., Expert Opin. Ther. Targets, 10(4), 2006, pp. 561-572.
Hackman, D., JAMA, 296(14), 2006, p. 1731.
Hackman, D., BMJ, 334, 2007, pp. 163-164.

*Primary Examiner*—James O Wilson
*Assistant Examiner*—Douglas M Willis
(74) *Attorney, Agent, or Firm*—George W. Johnston; Dennis P. Tramaloni; Brian C. Remy

(57) ABSTRACT

The present invention relates to a method of raising HDL cholesterol comprising administering to a patient in need thereof a compound of the formula

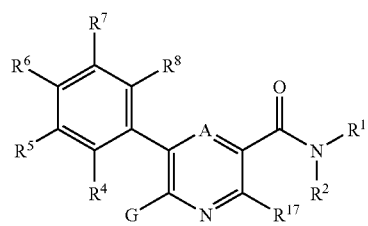

wherein A, G, $R^1$ to $R^8$ and $R^{17}$ are as defined in the description.

8 Claims, No Drawings

3-PYRIDINECARBOXAMIDE DERIVATIVES AS HDL-CHOLESTEROL RAISING AGENTS

PRIORITY TO RELATED APPLICATION(S)

This application is a continuation of U.S. application Ser. No. 11/904,425, filed Sep. 27, 2007; which claims the benefit of European Patent Application No. 06121755.0, filed Oct. 4, 2006. The entire contents of the above-identified applications are hereby incorporated by reference.

BACKGROUND OF THE INVENTION

The present invention is concerned with the use of 3-pyridinecarboxamide or 2-pyrazinecarboxamide derivatives as HDL-cholesterol raising agents.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as pharmaceutical compositions for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

SUMMARY OF THE INVENTION

In sum, the present invention relates to the use of the compounds of formula I:

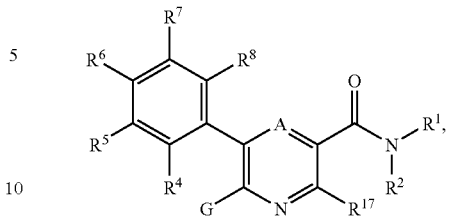

for raising HDL-cholesterol, wherein A, G, X and R1-R17 are as defined in the detailed description and the claims.

An object of the present invention is therefore to provide compounds which are potent HDL-cholesterol raising agents. It has been found that compounds of formula I show such a potential.

Further, the present invention relates to pharmaceutical compositions comprising a compound of formula I for use as HDL-cholesterol raising agents, and methods for the treatment and/or prophylaxis of diseases which are amenable to treatment with HDL-cholesterol raising agents, which methods comprise administering a compound of formula I to a human being or animal.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "alkyl", alone or in combination with other groups, refers to a branched or straight-chain monovalent saturated aliphatic hydrocarbon radical of one to twenty carbon atoms. In preferred embodiments, the alkyl has one to sixteen carbon atoms, and more preferably one to ten carbon atoms.

The term "lower alkyl" or "$C_{1-7}$-alkyl", alone or in combination with other groups, refers to a branched or straight-chain monovalent alkyl radical of one to seven carbon atoms. In preferred embodiments, the carbon has one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups are, for instance, methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are, for instance, —$CH_2$—O—$CH_3$, —$CH_2$—$CH_2$—O—$CH_3$, —$CH_2$—O—$CH_2$—$CH_3$ and the groups specifically exemplified herein. Most preferably, lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Preferred are $C_{3-7}$-hydroxyalkyl groups.

Examples of lower hydroxyalkyl groups are 2-hydroxybutyl, 3-hydroxy-2,2-dimethylpropyl and the groups specifically exemplified therein.

The term "halogen" refers to fluorine, chlorine, bromine or iodine. Preferred "halogen" groups are fluorine and chlorine.

The term "lower halogenalkyl" or "halogen-$C_{1-7}$-alkyl" refers to lower alkyl groups which are mono- or multiply substituted with halogen, preferably with fluoro or chloro, most preferably with fluoro. Examples of lower halogenalkyl groups are, for example, $-CF_3$, $-CHF_2$, $-CH_2Cl$, $-CH_2CF_3$, $-CH(CF_3)_2$, $-CF_2-CF_3$ and the groups specifically exemplified herein.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyhalogenalkyl" or "hydroxy-halogen-$C_{1-7}$-alkyl" refers to lower halogenalkyl groups as defined herein before which are additionally substituted with a hydroxy group. Examples of lower hydroxyhalogenalkyl groups are, for instance, 3,3,3-trifluoro-2-hydroxy-propyl and the groups specifically exemplified herein.

The term "carbamoyl" refers to the group $-CO-NH_2$.

The term "lower carbamoylalkyl" or "carbamoyl-$C_{1-7}$-alkyl" refers to lower alkyl groups as defined above wherein one of the hydrogen atoms of the lower alkyl group is replaced by a carbamoyl group. Examples of preferred lower carbamoylalkyl groups are 3-carbamoylpropyl, 4-carbamoylbutyl and 5-carbamoylpentyl, most preferably 4-carbamoylbutyl.

The term "lower alkylcarbonyl" refers to the group $-CO-R''$, wherein $R''$ is lower alkyl as defined above. "Lower alkylcarbonylamino" refers to the group $-NH-CO-R''$, wherein $R''$ is lower alkyl as defined above.

The term "lower alkylcarbonylaminoalkyl" or "$C_{1-7}$-alkylcarbonylamino-$C_{1-7}$-alkyl" refers to lower alkyl groups as defined above wherein one of the hydrogen atoms of the lower alkyl group is replaced by a lower alkylcarbonylamino group. A preferred lower alkylcarbonylaminoalkyl group is ethylcarbonylaminoethyl.

The term "cycloalkyl" or "$C_{3-7}$-cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclopropyl being especially preferred.

The term "lower cycloalkylalkyl" or "$C_{3-7}$-cycloalkyl-$C_{1-7}$-alkyl" refers to a lower alkyl group as defined above which is mono- or multiply substituted with a cycloalkyl group as defined above. Examples of lower cycloalkylalkyl groups are, for instance, $-CH_2$-cyclopropyl, $-CH_2-CH_2$-cyclopropyl, $-CH_2$-cyclopentyl and the groups specifically exemplified herein.

The term "heterocyclyl" refers to a saturated or partly unsaturated 3-, 4-, 5-, 6- or 7-membered ring which can comprise one, two or three atoms independently selected from the group consisting of nitrogen, oxygen and sulphur. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuryl, tetrahydrofuryl, dihydropyranyl, tetrahydropyranyl, and thiomorpholinyl. Preferred heterocyclyl groups are oxetanyl and [1,3]dioxolanyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "heteroaryl" refers to an aromatic 5- or 6-membered ring which can comprise one, two or three atoms independently selected from the group consisting of nitrogen, oxygen and sulphur. Examples of heteroaryl groups are, for instance, furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, or pyrrolyl. The heteroaryl group can optionally be mono- or disubstituted by lower alkyl. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrimidinyl, imidazolyl, triazolyl, and thiazolyl which groups can optionally be mono- or disubstituted by lower alkyl. Especially preferred are 3-methylisoxazolyl, 5-methylisoxazolyl, pyridyl, 3-methylpyridyl, pyrimidinyl, 1-methylimidazolyl, 2-methyl[1,2,4]triazolyl and 4-methylthiazolyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "form a 4-, 5-, 6- or 7-membered heterocyclic ring" refers to a N-heterocyclic ring such as azetidinyl, pyrrolidinyl, piperidinyl or azepanyl. Preferred is piperidinyl. The heterocyclic ring may optionally contain a further nitrogen, oxygen or sulfur atom, such as an imidazolidinyl, pyrazolidinyl, oxazolidinyl, isoxazolidinyl, thiazolidinyl, isothiazolidinyl, piperazinyl, morpholinyl or thiomorpholinyl.

The term "oxo" means that a C-atom of the heterocyclic ring may be substituted by $=O$, thus meaning that the heterocyclic ring may contain one or more carbonyl ($-CO-$) groups.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to a method of raising HDL cholesterol comprising administering to a patient in need thereof a compound of the formula

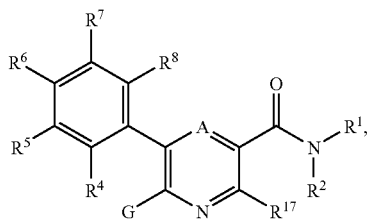

I or a pharmaceutically acceptable salt thereof, wherein

A is CH or N;

$R^2$ is hydrogen and $R^1$ is selected from the group consisting of:
  (a) cycloalkyl, which is optionally substituted by hydroxy, lower hydroxyalkyl or lower alkoxy,
  (b) 1-hydroxy-2-indanyl,
  (c) lower hydroxyalkyl,
  (d) lower hydroxyhalogenalkyl,
  (e) lower hydroxyalkoxyalkyl,
  (f) —$CH_2$—$CR^9R^{10}$-cycloalkyl, wherein $R^9$ is hydrogen or lower alkyl; and wherein $R^{10}$ is hydrogen, hydroxy or lower alkoxy; and
  (g) —$CR^{11}R^{12}$—$COOR^{13}$; wherein $R^{11}$ and $R^{12}$ independently from each other are hydrogen or lower alkyl; and wherein $R^{13}$ is lower alkyl;

or alternatively, $R^1$ and $R^2$ together with the nitrogen atom to which they are attached form a morpholinyl ring;

G is a group selected from the group consisting of:
  (a) —X—$R^3$, wherein X is O or $NR^{14}$, wherein $R^{14}$ is selected from the group consisting of hydrogen, lower alkyl and lower hydroxyalkyl; and $R^3$ is selected from the group consisting of:
    (1) lower alkyl,
    (2) cycloalkyl,
    (3) lower cycloalkylalkyl,
    (4) lower hydroxyalkyl,
    (5) lower alkoxyalkyl,
    (6) lower halogenalkyl,
    (7) lower carbamoylalkyl,
    (8) lower alkylcarbonylaminoalkyl,
    (9) lower phenylalkyl,
    (10) lower heterocyclylalkyl wherein the heterocyclyl group is unsubstituted or substituted by oxo,
    (11) lower heteroarylalkyl wherein the heteroaryl group is unsubstituted or mono- or di-substituted by lower alkyl, and
    (12) phenyl which is unsubstituted or mono- or di-substituted by halogen;
  or alternatively $R^3$ and $R^{14}$ together with the nitrogen atom to which they are attached form a 4-, 5-, 6- or 7-membered heterocyclic ring optionally containing a further heteroatom selected from the group consisting of nitrogen, oxygen and sulfur, said heterocyclic ring being optionally substituted by one or two groups independently selected from the group consisting of hydroxy, lower alkoxy and halogen;
  (b) —C≡C—$R^{15}$, wherein $R^{15}$ is selected from the group consisting of lower alkoxyalkyl, cycloalkyl and furanyl substituted by halogen; and
  (c) —$CH_2$—$CH_2$—$R^{16}$, wherein $R^{16}$ is selected from the group consisting of:
    (1) a cycloalkyl which is optionally substituted by hydroxy or lower alkoxy,
    (2) a heteroaryl which is pyridyl or imidazolyl, which is optionally substituted by lower alkyl or halogen, and
    (3) lower alkylaminocarbonyl;

$R^4$ and $R^8$ independently from each other are hydrogen or halogen;

$R^5$ and $R^7$ independently from each other are selected from the group consisting of hydrogen, lower alkyl, lower alkoxy, halogen, lower halogenalkyl, lower halogenalkoxy and cyano;

$R^6$ is selected from the group consisting of hydrogen, lower alkoxy, halogen, lower halogenalkyl, lower halogenalkoxy and cyano; and $R^{17}$ is selected from the group consisting of hydrogen, lower alkyl and lower halogenalkyl.

In a preferred aspect, the present invention relates to a method of raising HDL cholesterol comprising administering to a patient in need thereof the compounds of formula I having the formula

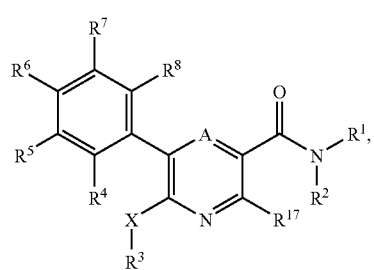

I-A wherein
A is CH or N;
R$^1$ is selected from the group consisting of
  cycloalkyl which is unsubstituted or substituted by hydroxy, lower hydroxyalkyl or lower alkoxy,
  1-hydroxy-2-indanyl,
  lower hydroxyalkyl, lower hydroxyhalogenalkyl, lower hydroxyalkoxyalkyl,
  —CH$_2$—CR$^9$R$^{10}$-cycloalkyl, and
  —CR$^{11}$R$^{12}$—COOR$^{13}$;
R$^9$ is hydrogen or lower alkyl;
R$^{10}$ is hydrogen, hydroxy or lower alkoxy;
R$^{11}$ and R$^{12}$ independently from each other are hydrogen or lower alkyl;
R$^{13}$ is lower alkyl;
R$^2$ is hydrogen;
or R$^1$ and R$^2$ together with the nitrogen atom they are attached to form a morpholinyl ring;
X is O or NR$^{14}$;
R$^{14}$ is selected from the group consisting of hydrogen, lower alkyl and lower hydroxyalkyl;
R$^3$ is selected from the group consisting of lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
or R$^3$ and R$^{14}$ together with the nitrogen atom they are attached to form a 4-, 5-, 6- or 7-membered heterocyclic ring optionally containing a further heteroatom selected from nitrogen, oxygen or sulfur, said heterocyclic ring being unsubstituted or substituted by one or two groups independently selected from hydroxy, lower alkoxy and halogen;
R$^4$ and R$^8$ independently from each other are hydrogen or halogen;
R$^5$ and R$^7$ independently from each other are selected from the group consisting of hydrogen, lower alkyl, lower alkoxy, halogen, lower halogenalkyl, lower halogenalkoxy and cyano;
R$^6$ is selected from the group consisting of hydrogen, lower alkoxy, halogen, lower halogenalkyl, lower halogenalkoxy and cyano;
R$^{17}$ is selected from the group consisting of hydrogen, lower alkyl and lower halogenalkyl; and pharmaceutically acceptable salts thereof.

In another aspect, the present invention relates to the use of compounds of formula I having the formula

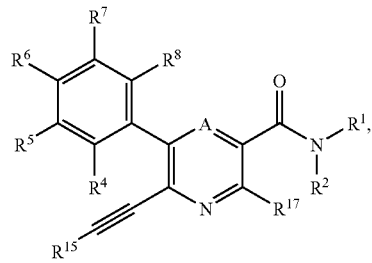

I-B wherein A, R$^1$ to R$^8$, R$^{15}$ and R$^{17}$ are as defined herein before, and pharmaceutically acceptable salts thereof, for the preparation of pharmaceutical compositions for the treatment and/or prophylaxis of diseases which can be treated with HDL-cholesterol raising agents.

In a further aspect, the present invention relates to the use of compounds of formula I having the formula

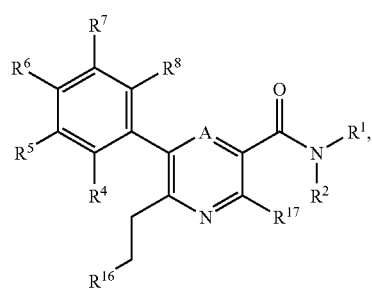

I-C wherein A, R$^1$ to R$^8$, R$^{16}$ and R$^{17}$ are as defined herein before, and pharmaceutically acceptable salts thereof, for the preparation of pharmaceutical compositions for the treatment and/or prophylaxis of diseases which can be treated with HDL-cholesterol raising agents.

In a preferred aspect, the present invention relates to the use of compounds of the formula I, wherein A is CH, for the treatment and/or prophylaxis of diseases which can be treated with HDL-cholesterol raising agents.

More preferably, the present invention relates to a method of raising HDL cholesterol comprising administering to a patient in need thereof a compound of the formula

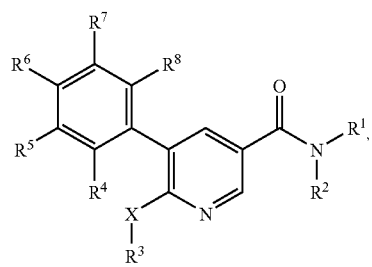

I-D wherein
R$^1$ is selected from the group consisting of
  cycloalkyl which is unsubstituted or substituted by hydroxy or lower alkoxy, lower hydroxyalkyl, lower hydroxyhalogenalkyl, —CH$_2$—CR$^9$R$^{10}$-cycloalkyl, and
—CR$^{11}$R$^{12}$—COOR$^{13}$;
R$^9$ is hydrogen or lower alkyl;
R$^{10}$ is hydrogen, hydroxy or lower alkoxy;
R$^{11}$ and R$^{12}$ independently from each other are hydrogen or lower alkyl;
R$^{13}$ is lower alkyl;
R$^2$ is hydrogen;
X is O or NR$^{14}$;
R$^{14}$ is hydrogen or lower alkyl;
R$^3$ is selected from the group consisting of lower alkyl,
  cycloalkyl,
  lower cycloalkylalkyl,
  lower alkoxyalkyl,
  lower halogenalkyl,
  lower carbamoylalkyl,
  lower phenylalkyl,
  lower heterocyclylalkyl,
  lower heteroarylalkyl wherein the heteroaryl group is unsubstituted or mono- or di-substituted by lower alkyl, and
  phenyl which is unsubstituted or mono- or di-substituted by halogen;
or R$^3$ and R$^{14}$ together with the nitrogen atom they are attached to form a 5-, 6- or 7-membered heterocyclic ring;
R$^4$ and R$^8$ independently from each other are hydrogen or halogen;
R$^5$ and R$^7$ independently from each other are selected from the group consisting of hydrogen, halogen, lower halogenalkyl, lower halogenalkoxy and cyano;
R$^6$ is selected from the group consisting of hydrogen, halogen, lower halogenalkyl, lower halogenalkoxy and cyano;

and pharmaceutically acceptable salts thereof.

Preferably, the invention relates to the use of compounds of formula I, wherein X is O. Also preferred is the use of compounds of formula I, wherein R$^1$ is cycloalkyl which is substituted by hydroxy, with those compounds, wherein R$^1$ is cyclohexyl substituted by hydroxy, being especially preferred.

In addition, compounds of formula I are preferably used, wherein R$^1$ is —CH$_2$—CR$^9$R$^{10}$-cycloalkyl and wherein R$^9$ is hydrogen and R$^{10}$ is hydroxy, with those compounds of formula I, wherein R$^1$ is —CH$_2$—CR$^9$R$^{10}$-cyclopropyl and wherein R$^9$ is hydrogen and R$^{10}$ is hydroxy, being more preferred.

Furthermore, the use of compounds of formula I is preferred, wherein R$^3$ is selected from the group consisting of lower cycloalkylalkyl, lower alkoxyalkyl and lower halogenalkyl, with those compounds of formula I, wherein R$^3$ is cyclopropylmethyl, 2-methoxyethoxy or 2,2,2-trifluoroethyl, being especially preferred.

Also preferably used are compounds of formula I according to the invention, wherein R$^6$ is halogen and R$^4$, R$^5$, R$^7$ and R$^8$ are hydrogen.

Thus, in a preferred embodiment, the invention relates to a method of raising HDL cholesterol comprising administering to a patient in need thereof compounds of formula I having the formula

I-E wherein
R$^1$ is cycloalkyl which is substituted by hydroxy, or —CH$_2$—CR$^9$R$^{10}$-cycloalkyl;
R$^9$ is hydrogen or lower alkyl;
R$^{10}$ is hydrogen, hydroxy or lower alkoxy;
R$^2$ is hydrogen;
R$^3$ is selected from the group consisting of lower cycloalkylalkyl, lower alkoxyalkyl and lower halogenalkyl;
R$^4$, R$^5$, R$^7$ and R$^8$ are hydrogen;
R$^6$ is halogen;

and pharmaceutically acceptable salts thereof.

Preferably, the invention relates to the use of compounds of formula I selected from the group consisting of:
5-(4-chloro-phenyl)-6-cyclopropylmethoxy-N-((1R,2R)-2-hydroxy-cyclohexyl)-nicotinamide,
5-(4-chloro-phenyl)-N-((1R,2R)-2-hydroxy-cyclohexyl)-6-(2-methoxy-ethoxy)-nicotinamide,
6-cyclopropylmethoxy-5-(4-fluoro-phenyl)-N-((1R,2R)-2-hydroxy-cyclohexyl)-nicotinamide,
5-(4-chloro-phenyl)-N-((1R,2R)-2-hydroxy-cyclohexyl)-6-(2,2,2-trifluoro-ethoxy)-nicotinamide,
N—((R)-2-cyclopropyl-2-hydroxy-propyl)-6-cyclopropylmethoxy-5-(4-fluoro-phenyl)-nicotinamide,
5-(2-chloro-5-trifluoromethyl-phenyl)-6-cyclopentyloxy-N-((1R,2R)-2-hydroxy-cyclohexyl)-nicotinamide,
6-butoxy-5-(2-fluoro-5-trifluoromethyl-phenyl)-N-((1R,2R)-2-hydroxy-cyclohexyl)-nicotinamide,
6-cyclohexyloxy-5-(2-fluoro-5-trifluoromethyl-phenyl)-N-((1R,2R)-2-hydroxy-cyclohexyl)-nicotinamide,
6-butoxy-N-(2-cyclopropyl-2-hydroxy-propyl)-5-(2-fluoro-5-trifluoromethyl-phenyl)-nicotinamide,
5-(4-chloro-phenyl)-6-cyclohexyloxy-N-((1R,2R)-2-hydroxy-cyclohexyl)-nicotinamide,
6-butoxy-5-(4-chloro-phenyl)-N-((1R,2R)-2-hydroxy-cyclohexyl)-nicotinamide,
5-(4-chloro-phenyl)-N-(2-cyclopropyl-2-hydroxy-propyl)-6-cyclopropylmethoxy-nicotinamide,
6-cyclopentyloxy-5-(2-fluoro-5-trifluoromethyl-phenyl)-N-((1R,2R)-2-hydroxy-cyclohexyl)-nicotinamide,
6-cyclopentyloxy-N-(2-cyclopropyl-2-hydroxy-propyl)-5-(2-fluoro-5-trifluoromethyl-phenyl)-nicotinamide,
6-(2-chloro-phenyl)-5-pyrrolidin-1-yl-pyrazine-2-carboxylic acid ((1R,2R)-2-hydroxy-cyclohexyl)-amide,
6-(2-chloro-phenyl)-5-cyclopentylamino-pyrazine-2-carboxylic acid ((1R,2R)-2-hydroxy-cyclohexyl)-amide,
5-(4-chloro-phenyl)-6-cyclopentyloxy-N-((1R,2R)-2-hydroxy-cyclohexyl)-nicotinamide,
5-(2-chloro-5-trifluoromethyl-phenyl)-N-(2-cyclopropyl-2-hydroxy-propyl)-6-cyclopropylmethoxy-nicotinamide,
5-(4-chloro-phenyl)-N-((1R,2R)-2-hydroxy-cyclohexyl)-6-phenoxy-nicotinamide, 6-(4-chloro-phenyl)-5-piperidin-1-yl-pyrazine-2-carboxylic acid (1-hydroxy-indan-2-yl)-amide,
6-(3,4-dichloro-phenyl)-5-pyrrolidin-1-yl-pyrazine-2-carboxylic acid (2-cyclopropyl-2-hydroxy-propyl)-amide,
5-(4-chloro-phenyl)-N-(2-cyclopropyl-2-hydroxy-propyl)-6-(2-methoxy-ethoxy)-nicotinamide,
[5-(4-chloro-phenyl)-6-(2-methoxy-ethoxy)-pyridin-3-yl]-morpholin-4-yl-methanone,
5-(4-chloro-phenyl)-N—((R)-1-hydroxymethyl-3-methyl-butyl)-6-(2-propionylamino-ethoxy)-nicotinamide,
5-(4-chloro-phenyl)-N—((R)-1-hydroxymethyl-pentyl)-6-(2-methoxy-ethoxy)-nicotinamide,
5-(4-chloro-phenyl)-N—((S)-1-hydroxymethyl-2,2-dimethyl-propyl)-6-(2-methoxy-ethoxy)-nicotinamide,
6-cyclopropylmethoxy-5-(3,4-difluoro-phenyl)-N-((trans)-2-hydroxy-cyclohexyl)-nicotinamide,
6-cyclopropylmethoxy-5-(4-fluoro-phenyl)-N-((trans)-2-hydroxy-cyclohexyl)-nicotinamide,
6-cyclopropylmethoxy-N-((trans)-2-hydroxy-cyclohexyl)-5-(4-trifluoromethyl-phenyl)-nicotinamide,
6-cyclopropylmethoxy-5-(3,4-dichloro-phenyl)-N-((trans)-2-hydroxy-cyclohexyl)-nicotinamide,
5-(4-cyano-phenyl)-6-cyclopropylmethoxy-N-((trans)-2-hydroxy-cyclohexyl)-nicotinamide,
6-(4-chloro-phenyl)-5-cyclopropylmethoxy-pyrazine-2-carboxylic acid ((R)-1-hydroxymethyl-3-methyl-butyl)-amide,
5-(4-chloro-phenyl)-N-(2-hydroxy-3-methoxy-propyl)-6-(2-methoxy-ethoxy)-nicotinamide,
6-(4-chloro-phenyl)-5-(3-methyl-butoxy)-pyrazine-2-carboxylic acid ((1R,2R)-2-hydroxy-cyclohexyl)-amide,
5-(2-chloro-phenoxy)-6-(4-chloro-phenyl)-pyrazine-2-carboxylic acid ((1R,2R)-2-hydroxy-cyclohexyl)-amide,
6-(4-fluoro-phenyl)-5-(3-methoxy-propoxy)-pyrazine-2-carboxylic acid (2-cyclopropyl-2-hydroxy-propyl)-amide,
5-cyclopropylmethoxy-6-(4-fluoro-phenyl)-pyrazine-2-carboxylic acid (2-cyclopropyl-2-hydroxy-propyl)-amide,
6-((R)-sec-butoxy)-5-(4-chloro-phenyl)-N-((1R,2R)-2-hydroxy-cyclohexyl)-nicotinamide,
N-((1R,2R)-2-hydroxy-cyclohexyl)-6-(2-methoxy-ethoxy)-5-(4-trifluoromethyl-phenyl)-nicotinamide,
N-((1R,2R)-2-hydroxy-cyclohexyl)-6-(2-methoxy-ethoxy)-5-(4-trifluoromethoxy-phenyl)-nicotinamide,
5-(4-chloro-phenyl)-N-((1R,2R)-2-hydroxy-cyclohexyl)-6-(2-isopropoxy-ethoxy)-nicotinamide,
5-(4-chloro-phenyl)-N-((1R,2R)-2-hydroxy-cyclohexyl)-6-isopropoxy-nicotinamide,
5-(4-chloro-phenyl)-N-((1R,2R)-2-hydroxy-cyclohexyl)-6-[(2-methoxy-ethyl)-methyl-amino]-nicotinamide,
5-(4-chloro-phenyl)-N-((1R,2R)-2-hydroxy-cyclohexyl)-6-(2-methoxy-1-methyl-ethoxy)-nicotinamide,
5-(4-chloro-phenyl)-N-((1R,2R)-2-hydroxy-cyclohexyl)-6-(1-methoxymethyl-propoxy)-nicotinamide,
6-(4-fluoro-phenyl)-5-((R)-2-methoxy-propoxy)-pyrazine-2-carboxylic acid (2-cyclopropyl-2-hydroxy-propyl)-amide,
5-(4-chloro-phenyl)-N-((1R,2R)-2-hydroxy-cyclohexyl)-6-isobutoxy-nicotinamide,
5-(4-chloro-phenyl)-6-(2-ethoxy-ethoxy)-N-((1R,2R)-2-hydroxy-cyclohexyl)-nicotinamide,
6-(4-chloro-phenyl)-5-[(R)-1-(tetrahydro-furan-2-yl)methoxy]-pyrazine-2-carboxylic acid ((S)-2-cyclopropyl-2-hydroxy-propyl)-amide,
6-(4-chloro-phenyl)-5-[(R)-1-(tetrahydro-furan-2-yl)methoxy]-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-((S)-2-methoxy-propoxy)-nicotinamide,
6-sec-butoxy-5-(4-chloro-phenyl)-N-((1R,2R)-2-hydroxy-cyclohexyl)-nicotinamide,
5-(4-chloro-phenyl)-N-((1R,2R)-2-hydroxy-cyclohexyl)-6-(oxetan-2-ylmethoxy)-nicotinamide,
5-(2-methoxy-ethoxy)-6-(4-trifluoromethyl-phenyl)-pyrazine-2-carboxylic acid (2-cyclopropyl-2-hydroxy-propyl)-amide,
5-cyclopropylmethoxy-6-(4-trifluoromethyl-phenyl)-pyrazine-2-carboxylic acid (2-cyclopropyl-2-hydroxy-propyl)-amide,
5-(3-methoxy-propoxy)-6-(4-trifluoromethyl-phenyl)-pyrazine-2-carboxylic acid (2-cyclopropyl-2-hydroxy-propyl)-amide,
5-butoxy-6-(4-trifluoromethyl-phenyl)-pyrazine-2-carboxylic acid (2-cyclopropyl-2-hydroxy-propyl)-amide,
6-(4-chloro-phenyl)-5-pyrrolidin-1-yl-pyrazine-2-carboxylic acid ((R)-2-cyclopropyl-2-hydroxy-propyl)-amide,
6-(4-chloro-phenyl)-5-(3-methyl-butylamino)-pyrazine-2-carboxylic acid ((R)-2-cyclopropyl-2-hydroxy-propyl)-amide,
6-(4-chloro-phenyl)-5-(cyclopropylmethyl-amino)-pyrazine-2-carboxylic acid ((R)-2-cyclopropyl-2-hydroxy-propyl)-amide,
6-(4-chloro-phenyl)-5-cyclopropylamino-pyrazine-2-carboxylic acid ((R)-2-cyclopropyl-2-hydroxy-propyl)-amide,
6-(4-chloro-phenyl)-5-(3-methoxy-azetidin-1-yl)-pyrazine-2-carboxylic acid ((R)-2-cyclopropyl-2-hydroxy-propyl)-amide,
6-(4-chloro-phenyl)-5-(3-hydroxy-azetidin-1-yl)-pyrazine-2-carboxylic acid ((R)-2-cyclopropyl-2-hydroxy-propyl)-amide,
5-(4-chloro-phenyl)-N-(2-cyclopropyl-2-hydroxy-propyl)-6-(2,2,2-trifluoro-ethoxy)-nicotinamide,
N-((1R,2R)-2-hydroxy-cyclohexyl)-6-(2,2,2-trifluoro-ethoxy)-5-(4-trifluoromethyl-phenyl)-nicotinamide,
5-(4-chloro-phenyl)-N-((1R,2R)-2-hydroxy-cyclohexyl)-6-[3-(2-oxo-pyrrolidin-1-yl)-propoxy]-nicotinamide,
5-cyclopropylmethoxy-6-(4-fluoro-phenyl)-pyrazine-2-carboxylic acid ((R)-2-cyclopropyl-2-hydroxy-propyl)-amide,
5-cyclopropylmethoxy-6-(4-fluoro-phenyl)-pyrazine-2-carboxylic acid ((S)-2-cyclopropyl-2-hydroxy-propyl)-amide,
5-(4-fluoro-phenyl)-N-((1R,2R)-2-hydroxy-cyclohexyl)-6-(3-methoxy-propoxy)-nicotinamide,
6-(4-chloro-phenyl)-5-(2,2,2-trifluoro-ethoxy)-pyrazine-2-carboxylic acid ((R)-2-cyclopropyl-2-hydroxy-propyl)-amide,
5,6-bis-(4-chloro-phenyl)-pyrazine-2-carboxylic acid ((S)-2-cyclopropyl-2-hydroxy-propyl)-amide,
5,6-bis-(4-chloro-phenyl)-pyrazine-2-carboxylic acid ((R)-2-cyclopropyl-2-hydroxy-propyl)-amide,
6-(4-chloro-phenyl)-5-[(S)-1-(tetrahydro-furan-2-yl)methoxy]-pyrazine-2-carboxylic acid ((S)-2-cyclopropyl-2-hydroxy-propyl)-amide,
5-(4-chloro-phenyl)-6-(cyclopropylmethyl-methyl-amino)-N-((1R,2R)-2-hydroxy-cyclohexyl)-nicotinamide,
6-(cyclopropylmethyl-methyl-amino)-5-(4-fluoro-phenyl)-N-((1R,2R)-2-hydroxy-cyclohexyl)-nicotinamide,
N-(2-cyclopropyl-2-hydroxy-propyl)-6-(cyclopropylmethyl-methyl-amino)-5-(4-fluoro-phenyl)-nicotinamide,
N—((S)-2-cyclopropyl-2-hydroxy-propyl)-6-cyclopropylmethoxy-5-(4-trifluoromethyl-phenyl)-nicotinamide, 5-butoxy-6-(4-chloro-phenyl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-(methyl-propyl-amino)-nicotinamide,
5-(4-chloro-phenyl)-N-(2-cyclopropyl-2-hydroxy-propyl)-6-(methyl-propyl-amino)-nicotinamide,
5-cyclopropylmethoxy-6-(4-trifluoromethyl-phenyl)-pyrazine-2-carboxylic acid ((R)-2-cyclopropyl-2-hydroxy-propyl)-amide,
5-azepan-1-yl-6-(4-chloro-phenyl)-pyrazine-2-carboxylic acid ((R)-2-cyclopropyl-2-hydroxy-propyl)-amide,
5-[methyl-(3-methyl-butyl)-amino]-6-(4-trifluoromethyl-phenyl)-pyrazine-2-carboxylic acid ((R)-2-cyclopropyl-2-hydroxy-propyl)-amide,
N—((S)-2-cyclopropyl-2-hydroxy-propyl)-6-(2-methoxy-ethoxy)-5-(4-trifluoromethyl-phenyl)-nicotinamide,
5-(4-chloro-phenyl)-N-(2-cyclopropyl-2-hydroxy-propyl)-6-[(2-methoxy-ethyl)-methyl-amino]-nicotinamide,
5-(4-fluoro-phenyl)-N-((1R,2R)-2-hydroxy-cyclohexyl)-6-(methyl-propyl-amino)-nicotinamide,
N—((R)-2-cyclopropyl-2-hydroxy-propyl)-6-cyclopropylmethoxy-5-(4-fluoro-phenyl)-nicotinamide,
3'-(4-chloro-phenyl)-3,4,5,6-tetrahydro-2H-[1,2']bipyridinyl-5'-carboxylic acid (2-cyclopropyl-2-hydroxy-propyl)-amide,
N—((S)-2-cyclopropyl-2-hydroxy-propyl)-6-cyclopropylmethoxy-5-(4-trifluoromethoxy-phenyl)-nicotinamide,
5-(4-chloro-phenyl)-N—((S)-2-cyclopropyl-2-hydroxy-propyl)-6-(2-methyl-2H-[1,2,4]triazol-3-ylmethoxy)-nicotinamide,
5-(4-chloro-phenyl)-N-((1R,2R)-2-hydroxy-cyclohexyl)-6-(1-methyl-1H-imidazol-2-ylmethoxy)-nicotinamide,
5-(4-chloro-phenyl)-N-((1R,2R)-2-hydroxy-cyclohexyl)-6-(2-methyl-2H-[1,2,4]triazol-3-ylmethoxy)-nicotinamide,
5-(4-chloro-phenyl)-N—((S)-2-cyclopropyl-2-hydroxy-propyl)-6-(pyridin-4-ylmethoxy)-nicotinamide,
6-(4-fluoro-phenyl)-5-(2,2,2-trifluoro-ethoxy)-pyrazine-2-carboxylic acid ((S)-2-cyclopropyl-2-hydroxy-propyl)-amide,
6-(4-fluoro-phenyl)-5-(2,2,2-trifluoro-ethoxy)-pyrazine-2-carboxylic acid ((1R,2R)-2-hydroxy-cyclohexyl)-amide,
6-(4-chloro-phenyl)-5-[(2-hydroxy-ethyl)-methyl-amino]-pyrazine-2-carboxylic acid ((R)-2-cyclopropyl-2-hydroxy-propyl)-amide,
6-(4-fluoro-phenyl)-5-(2-methoxy-ethoxy)-pyrazine-2-carboxylic acid ((1R,2R)-2-hydroxy-cyclohexyl)-amide,
5-cyclopropylmethoxy-6-(4-fluoro-phenyl)-pyrazine-2-carboxylic acid ((1R,2R)-2-hydroxy-cyclohexyl)-amide,
5-(4-cyano-phenyl)-N—(R)-2-cyclopropyl-2-hydroxy-propyl)-6-cyclopropylmethoxy-nicotinamide,
5-(4-chloro-phenyl)-N—((R)-2-cyclopropyl-2-hydroxy-propyl)-6-cyclopropylmethoxy-nicotinamide,
5-(4-chloro-phenyl)-N—((S)-2-cyclopropyl-2-hydroxy-propyl)-6-cyclopropylmethoxy-nicotinamide,
5-(4-chloro-phenyl)-N—((R)-2-cyclopropyl-2-hydroxy-propyl)-6-(3-methyl-isoxazol-5-ylmethoxy)-nicotinamide,
6-cyclopropylmethoxy-5-(4-fluoro-phenyl)-N-(1-hydroxymethyl-cyclopentyl)-nicotinamide,
5-[bis-(2-hydroxy-ethyl)-amino]-6-(4-chloro-phenyl)-pyrazine-2-carboxylic acid ((R)-2-cyclopropyl-2-hydroxy-propyl)-amide,
5-cyclopropylmethoxy-6-(4-trifluoromethoxy-phenyl)-pyrazine-2-carboxylic acid ((1R,2R)-2-hydroxy-cyclohexyl)-amide,
5-(cyclopropylmethyl-methyl-amino)-6-(4-trifluoromethoxy-phenyl)-pyrazine-2-carboxylic acid ((1R,2R)-2-hydroxy-cyclohexyl)-amide,
5-cyclopropylmethoxy-6-(4-trifluoromethoxy-phenyl)-pyrazine-2-carboxylic acid ((R)-2-cyclopropyl-2-hydroxy-propyl)-amide,
6-cyclopropylmethoxy-5-(4-fluoro-phenyl)-N-(2-hydroxy-2-methyl-propyl)-nicotinamide,
5-(5-bromo-furan-2-ylethynyl)-6-(4-chloro-phenyl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-(3-methoxy-prop-1-ynyl)-nicotinamide,
5-(4-chloro-phenyl)-6-cyclopropylethynyl-N-((1R,2R)-2-hydroxy-cyclohexyl)-nicotinamide,
5-(4-chloro-phenyl)-6-cyclopropylmethoxy-N-((1R,2R)-2-hydroxy-cyclohexyl)-2-methyl-nicotinamide,
5-(4-chloro-phenyl)-N-((1R,2R)-2-hydroxy-cyclohexyl)-6-(5-methyl-isoxazol-3-ylmethoxy)-nicotinamide,
N—((R)-2-cyclopropyl-2-hydroxy-propyl)-5-(4-fluoro-phenyl)-6-(pyridin-2-ylmethoxy)-nicotinamide,
5-(2-pyridin-3-yl-ethyl)-6-(4-trifluoromethoxy-phenyl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-2-methyl-6-(2,2,2-trifluoro-ethoxy)-nicotinamide,
6-(4-chloro-phenyl)-5-thiomorpholin-4-yl-pyrazine-2-carboxylic acid ((R)-2-cyclopropyl-2-hydroxy-propyl)-amide,
6-(4-chloro-phenyl)-5-(4,4-difluoro-piperidin-1-yl)-pyrazine-2-carboxylic acid ((R)-2-cyclopropyl-2-hydroxy-propyl)-amide,
6-(4-chloro-phenyl)-5-(2-cyclopropyl-ethyl)-pyrazine-2-carboxylic acid ((R)-2-cyclopropyl-2-hydroxy-propyl)-amide,
5-(2-pyridin-2-yl-ethyl)-6-(4-trifluoromethoxy-phenyl)-pyrazine-2-carboxylic acid ((R)-2-cyclopropyl-2-hydroxy-propyl)-amide,
6-cyclopropylmethoxy-N-(3,3,3-trifluoro-2-hydroxy-2-methyl-propyl)-5-(4-trifluoromethyl-phenyl)-nicotinamide,
6-cyclopropylmethoxy-N-(3,3,3-trifluoro-2-hydroxy-2-methyl-propyl)-5-(4-trifluoromethoxy-phenyl)-nicotinamide,
5-(4-fluoro-phenyl)-N-((1R,2R)-2-hydroxy-cyclohexyl)-6-(3-methyl-pyridin-2-ylmethoxy)-nicotinamide,
5-(4-chloro-phenyl)-N-((1R,2R)-2-hydroxy-cyclohexyl)-6-(pyridin-2-ylmethoxy)-nicotinamide,
6-(4-fluoro-phenyl)-5-piperidin-1-yl-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-[2-(1-hydroxy-cyclopentyl)-ethyl]-nicotinamide,
5-(4-cyano-phenyl)-6-cyclopropylmethoxy-N-((1R,2R)-2-hydroxy-cyclohexyl)-nicotinamide,
6-cyclopropylmethoxy-5-(4-fluoro-phenyl)-N—((R)-3,3,3-trifluoro-2-hydroxy-2-methyl-propyl)-nicotinamide,
5-(4-chloro-phenyl)-6-cyclopropylmethoxy-N-((1R,2R)-2-hydroxy-cyclohexyl)-2-trifluoromethyl-nicotinamide
N—((S)-1-hydroxymethyl-3-methyl-butyl)-5-(3-methoxy-phenyl)-6-pyrrolidin-1-yl-nicotinamide,
N—((S)-1-hydroxymethyl-3-methyl-butyl)-5-(4-methoxy-phenyl)-6-pyrrolidin-1-yl-nicotinamide,
5-(4-chloro-3-methyl-phenyl)-N—((R)-1-hydroxymethyl-3-methyl-butyl)-6-pyrrolidin-1-yl-nicotinamide,
N—((R)-1-hydroxymethyl-3-methyl-butyl)-5-(3-methoxy-phenyl)-6-pyrrolidin-1-yl-nicotinamide,
N—((R)-1-hydroxymethyl-3-methyl-butyl)-5-(4-methoxy-phenyl)-6-pyrrolidin-1-yl-nicotinamide, N—((R)-1-hydroxymethyl-3-methyl-butyl)-6-pyrrolidin-1-yl-5-(4-trifluoromethyl-phenyl)-nicotinamide,
N—((R)-1-hydroxymethyl-3-methyl-butyl)-6-pyrrolidin-1-yl-5-(4-trifluoromethoxy-phenyl)-nicotinamide,
5-(4-cyano-phenyl)-N—((R)-1-hydroxymethyl-3-methyl-butyl)-6-pyrrolidin-1-yl-nicotinamide,
5-(4-chloro-phenyl)-N-((1R,2R)-2-hydroxy-cyclohexyl)-6-(2-pyridin-2-yl-ethyl)-nicotinamide,
N-((1R,2R)-2-hydroxy-cyclohexyl)-6-[2-(3-methyl-3H-imidazol-4-yl)-ethyl]-5-(4-trifluoromethyl-phenyl)-nicotinamide,
5-(4-chloro-phenyl)-6-[2-(5-fluoro-pyridin-2-yl)-ethyl]-N-((1R,2R)-2-hydroxy-cyclohexyl)-nicotinamide,
6-[2-(5-fluoro-pyridin-2-yl)-ethyl]-N-((1R,2R)-2-hydroxy-cyclohexyl)-5-(4-trifluoromethyl-phenyl)-nicotinamide,
5-(4-chloro-phenyl)-N—((R)-2-cyclopropyl-2-hydroxy-propyl)-6-(2-pyridin-2-yl-ethyl)-nicotinamide,
N—((R)-2-cyclopropyl-2-hydroxy-propyl)-6-(2-pyridin-2-yl-ethyl)-5-(4-trifluoromethyl-phenyl)-nicotinamide,
2-{[6-(4-fluoro-phenyl)-5-piperidin-1-yl-pyrazine-2-carbonyl]-amino}-2-methyl-propionic acid methyl ester,
(R)-2-{[6-(4-fluoro-phenyl)-5-pyrrolidin-1-yl-pyrazine-2-carbonyl]-amino}-3-methyl-butyric acid methyl ester
6-(4-butylcarbamoyl-butoxy)-5-(4-chloro-phenyl)-N-((1R,2R)-2-hydroxy-cyclohexyl)-nicotinamide,
5-[4-(2-butylcarbamoyl-ethyl)-phenyl]-6-cyclopropylmethoxy-N-((1R,2R)-2-hydroxy-cyclohexyl)-nicotinamide,
5-(2,4-dichloro-phenyl)-N-(2-hydroxy-ethyl)-6-propoxy-nicotinamide,
6-cyclopentylmethoxy-5-(2,4-dichloro-phenyl)-N-(2-hydroxy-ethyl)-nicotinamide,
5-(4-chloro-phenyl)-N—((S)-1-hydroxymethyl-3-methyl-butyl)-6-pyrrolidin-1-yl-nicotinamide,
5-(3,4-dichloro-phenyl)-N—((S)-1-hydroxymethyl-3-methyl-butyl)-6-pyrrolidin-1-yl-nicotinamide,
5-(4-chloro-3-methyl-phenyl)-N—((S)-1-hydroxymethyl-3-methyl-butyl)-6-pyrrolidin-1-yl-nicotinamide,
5-(2-fluoro-phenyl)-N—((R)-1-hydroxymethyl-3-methyl-butyl)-6-pyrrolidin-1-yl-nicotinamide,
5-(4-fluoro-phenyl)-N—((R)-1-hydroxymethyl-3-methyl-butyl)-6-pyrrolidin-1-yl-nicotinamide,
5-(3-chloro-phenyl)-N—((R)-1-hydroxymethyl-3-methyl-butyl)-6-pyrrolidin-1-yl-nicotinamide,
5-(4-chloro-phenyl)-N—((R)-1-hydroxymethyl-3-methyl-butyl)-6-pyrrolidin-1-yl-nicotinamide,
5-(3,4-dichloro-phenyl)-N—((R)-1-hydroxymethyl-3-methyl-butyl)-6-pyrrolidin-1-yl-nicotinamide,
3'-(3-chloro-phenyl)-3,4,5,6-tetrahydro-2H-[1,2']bipyridinyl-5'-carboxylic acid ((S)-1-hydroxymethyl-3-methyl-butyl)-amide, and all pharmaceutically acceptable salts thereof.

Especially preferred is the use of compounds of formula I selected from the group consisting of:
5-(4-chloro-phenyl)-6-cyclopropylmethoxy-N-((1R,2R)-2-hydroxy-cyclohexyl)-nicotinamide,
5-(4-chloro-phenyl)-N-((1R,2R)-2-hydroxy-cyclohexyl)-6-(2-methoxy-ethoxy)-nicotinamide,
N—((R)-2-cyclopropyl-2-hydroxy-propyl)-6-cyclopropylmethoxy-5-(4-fluoro-phenyl)-nicotinamide,
5-(4-chloro-phenyl)-N-((1R,2R)-2-hydroxy-cyclohexyl)-6-(2,2,2-trifluoro-ethoxy)-nicotinamide,
6-cyclopropylmethoxy-5-(4-fluoro-phenyl)-N-((1R,2R)-2-hydroxy-cyclohexyl)-nicotinamide, and all pharmaceutically acceptable salts thereof.

Even more preferred is the use of compounds of formula I selected from the group consisting of:
5-(4-chloro-phenyl)-6-cyclopropylmethoxy-N-((1R,2R)-2-hydroxy-cyclohexyl)-nicotinamide,
5-(4-chloro-phenyl)-N-((1R,2R)-2-hydroxy-cyclohexyl)-6-(2-methoxy-ethoxy)-nicotinamide,
6-cyclopropylmethoxy-5-(4-fluoro-phenyl)-N-((1R,2R)-2-hydroxy-cyclohexyl)-nicotinamide,
5-(4-chloro-phenyl)-N-((1R,2R)-2-hydroxy-cyclohexyl)-6-(2,2,2-trifluoro-ethoxy)-nicotinamide,
N—((R)-2-cyclopropyl-2-hydroxy-propyl)-6-cyclopropylmethoxy-5-(4-fluoro-phenyl)-nicotinamide,
6-butoxy-5-(4-chloro-phenyl)-N-((1R,2R)-2-hydroxy-cyclohexyl)-nicotinamide,
5-(4-chloro-phenyl)-N-(2-cyclopropyl-2-hydroxy-propyl)-6-cyclopropylmethoxy-nicotinamide,
6-cyclopentyloxy-5-(2-fluoro-5-trifluoromethyl-phenyl)-N-((1R,2R)-2-hydroxy-cyclohexyl)-nicotinamide,
6-(2-chloro-phenyl)-5-pyrrolidin-1-yl-pyrazine-2-carboxylic acid ((1R,2R)-2-hydroxy-cyclohexyl)-amide,
6-(2-chloro-phenyl)-5-cyclopentylamino-pyrazine-2-carboxylic acid ((1R,2R)-2-hydroxy-cyclohexyl)-amide,
5-(4-chloro-phenyl)-6-cyclopentyloxy-N-((1R,2R)-2-hydroxy-cyclohexyl)-nicotinamide,
5-(2-chloro-5-trifluoromethyl-phenyl)-N-(2-cyclopropyl-2-hydroxy-propyl)-6-cyclopropylmethoxy-nicotinamide,
6-(4-chloro-phenyl)-5-piperidin-1-yl-pyrazine-2-carboxylic acid (1-hydroxy-indan-2-yl)-amide,
6-(3,4-dichloro-phenyl)-5-pyrrolidin-1-yl-pyrazine-2-carboxylic acid (2-cyclopropyl-2-hydroxy-propyl)-amide,
5-(4-chloro-phenyl)-N—((R)-1-hydroxymethyl-pentyl)-6-(2-methoxy-ethoxy)-nicotinamide,
6-cyclopropylmethoxy-5-(4-fluoro-phenyl)-N-((trans)-2-hydroxy-cyclohexyl)-nicotinamide,
6-cyclopropylmethoxy-5-(3,4-dichloro-phenyl)-N-((trans)-2-hydroxy-cyclohexyl)-nicotinamide,
6-(4-chloro-phenyl)-5-cyclopropylmethoxy-pyrazine-2-carboxylic acid ((R)-1-hydroxymethyl-3-methyl-butyl)-amide,
6-(4-fluoro-phenyl)-5-(3-methoxy-propoxy)-pyrazine-2-carboxylic acid (2-cyclopropyl-2-hydroxy-propyl)-amide,
5-cyclopropylmethoxy-6-(4-fluoro-phenyl)-pyrazine-2-carboxylic acid (2-cyclopropyl-2-hydroxy-propyl)-amide,
6-((R)-sec-butoxy)-5-(4-chloro-phenyl)-N-((1R,2R)-2-hydroxy-cyclohexyl)-nicotinamide,
5-(4-chloro-phenyl)-N-((1R,2R)-2-hydroxy-cyclohexyl)-6-[(2-methoxy-ethyl)-methyl-amino]-nicotinamide,
5-(4-chloro-phenyl)-N-((1R,2R)-2-hydroxy-cyclohexyl)-6-(2-methoxy-1-methyl-ethoxy)-nicotinamide,
5-(4-chloro-phenyl)-N-((1R,2R)-2-hydroxy-cyclohexyl)-6-(1-methoxymethyl-propoxy)-nicotinamide,
6-(4-fluoro-phenyl)-5-((R)-2-methoxy-propoxy)-pyrazine-2-carboxylic acid (2-cyclopropyl-2-hydroxy-propyl)-amide,
6-(4-chloro-phenyl)-5-[(R)-1-(tetrahydro-furan-2-yl)methoxy]-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-((S)-2-methoxy-propoxy)-nicotinamide,
6-sec-butoxy-5-(4-chloro-phenyl)-N-((1R,2R)-2-hydroxy-cyclohexyl)-nicotinamide,
6-(4-chloro-phenyl)-5-(3-methyl-butylamino)-pyrazine-2-carboxylic acid ((R)-2-cyclopropyl-2-hydroxy-propyl)-amide,
6-(4-chloro-phenyl)-5-(cyclopropylmethyl-amino)-pyrazine-2-carboxylic acid ((R)-2-cyclopropyl-2-hydroxy-propyl)-amide, 5-(4-chloro-phenyl)-N-(2-cyclopropyl-2-hydroxy-propyl)-6-(2,2,2-trifluoro-ethoxy)-nicotinamide
5,6-bis-(4-chloro-phenyl)-pyrazine-2-carboxylic acid ((R)-2-cyclopropyl-2-hydroxy-propyl)-amide,
5-(4-chloro-phenyl)-6-(cyclopropylmethyl-methyl-amino)-N-((1R,2R)-2-hydroxy-cyclohexyl)-nicotinamide,
6-(cyclopropylmethyl-methyl-amino)-5-(4-fluoro-phenyl)-N-((1R,2R)-2-hydroxy-cyclohexyl)-nicotinamide,
N-(2-cyclopropyl-2-hydroxy-propyl)-6-(cyclopropylmethyl-methyl-amino)-5-(4-fluoro-phenyl)-nicotinamide,
N—((S)-2-cyclopropyl-2-hydroxy-propyl)-6-cyclopropylmethoxy-5-(4-trifluoromethyl-phenyl)-nicotinamide,
5-butoxy-6-(4-chloro-phenyl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-(methyl-propyl-amino)-nicotinamide,
5-(4-chloro-phenyl)-N-(2-cyclopropyl-2-hydroxy-propyl)-6-(methyl-propyl-amino)-nicotinamide,
5-cyclopropylmethoxy-6-(4-trifluoromethyl-phenyl)-pyrazine-2-carboxylic acid ((R)-2-cyclopropyl-2-hydroxy-propyl)-amide,
N—((S)-2-cyclopropyl-2-hydroxy-propyl)-6-(2-methoxy-ethoxy)-5-(4-trifluoromethyl-phenyl)-nicotinamide,
5-(4-fluoro-phenyl)-N-((1R,2R)-2-hydroxy-cyclohexyl)-6-(methyl-propyl-amino)-nicotinamide,
N—((S)-2-cyclopropyl-2-hydroxy-propyl)-6-cyclopropylmethoxy-5-(4-trifluoromethoxy-phenyl)-nicotinamide,
5-(4-chloro-phenyl)-N—((S)-2-cyclopropyl-2-hydroxy-propyl)-6-(pyridin-4-ylmethoxy)-nicotinamide,
6-(4-fluoro-phenyl)-5-(2,2,2-trifluoro-ethoxy)-pyrazine-2-carboxylic acid ((S)-2-cyclopropyl-2-hydroxy-propyl)-amide,
6-(4-fluoro-phenyl)-5-(2,2,2-trifluoro-ethoxy)-pyrazine-2-carboxylic acid ((1R,2R)-2-hydroxy-cyclohexyl)-amide,
6-(4-fluoro-phenyl)-5-(2-methoxy-ethoxy)-pyrazine-2-carboxylic acid ((1R,2R)-2-hydroxy-cyclohexyl)-amide,
5-cyclopropylmethoxy-6-(4-fluoro-phenyl)-pyrazine-2-carboxylic acid ((1R,2R)-2-hydroxy-cyclohexyl)-amide,
5-(4-chloro-phenyl)-N—((R)-2-cyclopropyl-2-hydroxy-propyl)-6-cyclopropylmethoxy-nicotinamide,
5-(4-chloro-phenyl)-N—((S)-2-cyclopropyl-2-hydroxy-propyl)-6-cyclopropylmethoxy-nicotinamide,
5-(4-chloro-phenyl)-N—((R)-2-cyclopropyl-2-hydroxy-propyl)-6-(3-methyl-isoxazol-5-ylmethoxy)-nicotinamide,
5-cyclopropylmethoxy-6-(4-trifluoromethoxy-phenyl)-pyrazine-2-carboxylic acid ((1R,2R)-2-hydroxy-cyclohexyl)-amide,
5-(cyclopropylmethyl-methyl-amino)-6-(4-trifluoromethoxy-phenyl)-pyrazine-2-carboxylic acid ((1R,2R)-2-hydroxy-cyclohexyl)-amide,
5-cyclopropylmethoxy-6-(4-trifluoromethoxy-phenyl)-pyrazine-2-carboxylic acid ((R)-2-cyclopropyl-2-hydroxy-propyl)-amide,
5-(4-chloro-phenyl)-6-cyclopropylmethoxy-N-((1R,2R)-2-hydroxy-cyclohexyl)-2-methyl-nicotinamide,
N—((R)-2-cyclopropyl-2-hydroxy-propyl)-5-(4-fluoro-phenyl)-6-(pyridin-2-ylmethoxy)-nicotinamide,
6-(4-chloro-phenyl)-5-thiomorpholin-4-yl-pyrazine-2-carboxylic acid ((R)-2-cyclopropyl-2-hydroxy-propyl)-amide,
6-cyclopropylmethoxy-N-(3,3,3-trifluoro-2-hydroxy-2-methyl-propyl)-5-(4-trifluoromethyl-phenyl)-nicotinamide,
5-(4-chloro-phenyl)-N-((1R,2R)-2-hydroxy-cyclohexyl)-6-(pyridin-2-ylmethoxy)-nicotinamide,
5-(4-cyano-phenyl)-6-cyclopropylmethoxy-N-((1R,2R)-2-hydroxy-cyclohexyl)-nicotinamide,
6-cyclopropylmethoxy-5-(4-fluoro-phenyl)-N—((R)-3,3,3-trifluoro-2-hydroxy-2-methyl-propyl)-nicotinamide,
5-(4-chloro-3-methyl-phenyl)-N—((R)-1-hydroxymethyl-3-methyl-butyl)-6-pyrrolidin-1-yl-nicotinamide,
N—((R)-1-hydroxymethyl-3-methyl-butyl)-5-(3-methoxy-phenyl)-6-pyrrolidin-1-yl-nicotinamide,
N—((R)-1-hydroxymethyl-3-methyl-butyl)-6-pyrrolidin-1-yl-5-(4-trifluoromethoxy-phenyl)-nicotinamide,
5-(4-chloro-phenyl)-N-((1R,2R)-2-hydroxy-cyclohexyl)-6-(2-pyridin-2-yl-ethyl)-nicotinamide
5-(4-chloro-phenyl)-6-[2-(5-fluoro-pyridin-2-yl)-ethyl]-N-((1R,2R)-2-hydroxy-cyclohexyl)-nicotinamide,
6-(butylcarbamoyl-butoxy)-5-(4-chloro-phenyl)-N-((1R,2R)-2-hydroxy-cyclohexyl)-nicotinamide,
5-[4-(2-butylcarbamoyl-ethyl)-phenyl]-6-cyclopropylmethoxy-N-((1R,2R)-2-hydroxy-cyclohexyl)-nicotinamide,
5-(2-fluoro-phenyl)-N—((R)-1-hydroxymethyl-3-methyl-butyl)-6-pyrrolidin-1-yl-nicotinamide,
5-(4-fluoro-phenyl)-N—((R)-1-hydroxymethyl-3-methyl-butyl)-6-pyrrolidin-1-yl-nicotinamide,
5-(3-chloro-phenyl)-N—((R)-1-hydroxymethyl-3-methyl-butyl)-6-pyrrolidin-1-yl-nicotinamide,
5-(4-chloro-phenyl)-N—((R)-1-hydroxymethyl-3-methyl-butyl)-6-pyrrolidin-1-yl-nicotinamide,
5-(3,4-dichloro-phenyl)-N—((R)-1-hydroxymethyl-3-methyl-butyl)-6-pyrrolidin-1-yl-nicotinamide,
3'-(3-chloro-phenyl)-3,4,5,6-tetrahydro-2H-[1,2']bipyridinyl-5'-carboxylic acid ((S)-1-hydroxymethyl-3-methyl-butyl)-amide, and pharmaceutically acceptable salts thereof.

The invention thus relates to compounds of formula I as defined herein before for use for the treatment and/or prophylaxis of diseases which can be treated with HDL-cholesterol raising agents.

The invention further relates to new compounds of formula I selected from the group consisting of:
6-cyclohexyloxy-5-(2-fluoro-5-trifluoromethyl-phenyl)-N-((1R,2R)-2-hydroxy-cyclohexyl)-nicotinamide,
6-butoxy-N-(2-cyclopropyl-2-hydroxy-propyl)-5-(2-fluoro-5-trifluoromethyl-phenyl)-nicotinamide,
5-(4-chloro-phenyl)-6-cyclohexyloxy-N-((1R,2R)-2-hydroxy-cyclohexyl)-nicotinamide,
6-cyclopentyloxy-5-(2-fluoro-5-trifluoromethyl-phenyl)-N-((1R,2R)-2-hydroxy-cyclohexyl)-nicotinamide,
6-cyclopentyloxy-N-(2-cyclopropyl-2-hydroxy-propyl)-5-(2-fluoro-5-trifluoromethyl-phenyl)-nicotinamide,
6-(2-chloro-phenyl)-5-pyrrolidin-1-yl-pyrazine-2-carboxylic acid ((1R,2R)-2-hydroxy-cyclohexyl)-amide,
6-(2-chloro-phenyl)-5-cyclopentylamino-pyrazine-2-carboxylic acid ((1R,2R)-2-hydroxy-cyclohexyl)-amide,
5-(4-chloro-phenyl)-6-cyclopentyloxy-N-((1R,2R)-2-hydroxy-cyclohexyl)-nicotinamide,
5-(2-chloro-5-trifluoromethyl-phenyl)-N-(2-cyclopropyl-2-hydroxy-propyl)-6-cyclopropylmethoxy-nicotinamide,
5-(4-chloro-phenyl)-N-((1R,2R)-2-hydroxy-cyclohexyl)-6-phenoxy-nicotinamide,
6-(4-chloro-phenyl)-5-piperidin-1-yl-pyrazine-2-carboxylic acid (1-hydroxy-indan-2-yl)-amide,
6-(3,4-dichloro-phenyl)-5-pyrrolidin-1-yl-pyrazine-2-carboxylic acid (2-cyclopropyl-2-hydroxy-propyl)-amide,
[5-(4-chloro-phenyl)-6-(2-methoxy-ethoxy)-pyridin-3-yl]-morpholin-4-yl-methanone,
5-(4-chloro-phenyl)-N—((R)-1-hydroxymethyl-3-methyl-butyl)-6-(2-propionylamino-ethoxy)-nicotinamide, 5-(4-chloro-phenyl)-N—((R)-1-hydroxymethyl-pentyl)-6-(2-methoxy-ethoxy)-nicotinamide,
5-(4-chloro-phenyl)-N—((S)-1-hydroxymethyl-2,2-dimethyl-propyl)-6-(2-methoxy-ethoxy)-nicotinamide,
6-cyclopropylmethoxy-5-(3,4-dichloro-phenyl)-N-((trans)-2-hydroxy-cyclohexyl)-nicotinamide,
6-(4-chloro-phenyl)-5-cyclopropylmethoxy-pyrazine-2-carboxylic acid ((R)-1-hydroxymethyl-3-methyl-butyl)-amide,
5-(4-chloro-phenyl)-N-(2-hydroxy-3-methoxy-propyl)-6-(2-methoxy-ethoxy)-nicotinamide,
5-(2-chloro-phenoxy)-6-(4-chloro-phenyl)-pyrazine-2-carboxylic acid ((1R,2R)-2-hydroxy-cyclohexyl)-amide,
6-(4-fluoro-phenyl)-5-(3-methoxy-propoxy)-pyrazine-2-carboxylic acid (2-cyclopropyl-2-hydroxy-propyl)-amide,
6-((R)-sec-butoxy)-5-(4-chloro-phenyl)-N-((1R,2R)-2-hydroxy-cyclohexyl)-nicotinamide,
5-(4-chloro-phenyl)-N-((1R,2R)-2-hydroxy-cyclohexyl)-6-isopropoxy-nicotinamide,
5-(4-chloro-phenyl)-N-((1R,2R)-2-hydroxy-cyclohexyl)-6-(2-methoxy-1-methyl-ethoxy)-nicotinamide,
5-(4-chloro-phenyl)-N-((1R,2R)-2-hydroxy-cyclohexyl)-6-(1-methoxymethyl-propoxy)-nicotinamide,
6-(4-fluoro-phenyl)-5-((R)-2-methoxy-propoxy)-pyrazine-2-carboxylic acid (2-cyclopropyl-2-hydroxy-propyl)-amide,
5-(4-chloro-phenyl)-N-((1R,2R)-2-hydroxy-cyclohexyl)-6-((S)-2-methoxy-propoxy)-nicotinamide,
6-sec-butoxy-5-(4-chloro-phenyl)-N-((1R,2R)-2-hydroxy-cyclohexyl)-nicotinamide,
5-cyclopropylmethoxy-6-(4-trifluoromethyl-phenyl)-pyrazine-2-carboxylic acid (2-cyclopropyl-2-hydroxy-propyl)-amide,
6-(4-chloro-phenyl)-5-(3-methyl-butylamino)-pyrazine-2-carboxylic acid ((R)-2-cyclopropyl-2-hydroxy-propyl)-amide,
6-(4-chloro-phenyl)-5-cyclopropylamino-pyrazine-2-carboxylic acid ((R)-2-cyclopropyl-2-hydroxy-propyl)-amide,
6-(4-chloro-phenyl)-5-(3-methoxy-azetidin-1-yl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-[3-(2-oxo-pyrrolidin-1-yl)-propoxy]-nicotinamide,
5-(4-fluoro-phenyl)-N-((1R,2R)-2-hydroxy-cyclohexyl)-6-(3-methoxy-propoxy)-nicotinamide,
6-(4-chloro-phenyl)-5-[(S)-1-(tetrahydro-furan-2-yl)methoxy]-pyrazine-2-carboxylic acid ((S)-2-cyclopropyl-2-hydroxy-propyl)-amide,
N-(2-cyclopropyl-2-hydroxy-propyl)-6-(cyclopropylmethyl-methyl-amino)-5-(4-fluoro-phenyl)-nicotinamide,
5-(4-chloro-phenyl)-N-(2-cyclopropyl-2-hydroxy-propyl)-6-(methyl-propyl-amino)-nicotinamide,
5-cyclopropylmethoxy-6-(4-trifluoromethyl-phenyl)-pyrazine-2-carboxylic acid ((R)-2-cyclopropyl-2-hydroxy-propyl)-amide,
N—((S)-2-cyclopropyl-2-hydroxy-propyl)-6-(2-methoxy-ethoxy)-5-(4-trifluoromethyl-phenyl)-nicotinamide,
5-(4-chloro-phenyl)-N-(2-cyclopropyl-2-hydroxy-propyl)-6-[(2-methoxy-ethyl)-methyl-amino]-nicotinamide,
3'-(4-chloro-phenyl)-3,4,5,6-tetrahydro-2H-[1,2']bipyridinyl-5'-carboxylic acid (2-cyclopropyl-2-hydroxy-propyl)-amide,
N—((S)-2-cyclopropyl-2-hydroxy-propyl)-6-cyclopropylmethoxy-5-(4-trifluoromethoxy-phenyl)-nicotinamide,
5-(4-chloro-phenyl)-N—((S)-2-cyclopropyl-2-hydroxy-propyl)-6-(2-methyl-2H-[1,2,4]triazol-3-ylmethoxy)-nicotinamide,
5-(4-chloro-phenyl)-N—((S)-2-cyclopropyl-2-hydroxy-propyl)-6-(pyridin-4-ylmethoxy)-nicotinamide,
6-(4-fluoro-phenyl)-5-(2,2,2-trifluoro-ethoxy)-pyrazine-2-carboxylic acid ((S)-2-cyclopropyl-2-hydroxy-propyl)-amide,
5-cyclopropylmethoxy-6-(4-fluoro-phenyl)-pyrazine-2-carboxylic acid ((1R,2R)-2-hydroxy-cyclohexyl)-amide,
5-(4-cyano-phenyl)-N—((R)-2-cyclopropyl-2-hydroxy-propyl)-6-cyclopropylmethoxy-nicotinamide,
5-(4-chloro-phenyl)-N—((S)-2-cyclopropyl-2-hydroxy-propyl)-6-cyclopropylmethoxy-nicotinamide,
6-cyclopropylmethoxy-5-(4-fluoro-phenyl)-N-(1-hydroxymethyl-cyclopentyl)-nicotinamide,
5-[bis-(2-hydroxy-ethyl)-amino]-6-(4-chloro-phenyl)-pyrazine-2-carboxylic acid ((R)-2-cyclopropyl-2-hydroxy-propyl)-amide,
5-(5-bromo-furan-2-ylethynyl)-6-(4-chloro-phenyl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-(3-methoxy-prop-1-ynyl)-nicotinamide,
5-(4-chloro-phenyl)-6-cyclopropylethynyl-N-((1R,2R)-2-hydroxy-cyclohexyl)-nicotinamide,
5-(4-chloro-phenyl)-6-cyclopropylmethoxy-N-((1R,2R)-2-hydroxy-cyclohexyl)-2-methyl-nicotinamide,
5-(2-pyridin-3-yl-ethyl)-6-(4-trifluoromethoxy-phenyl)-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-2-methyl-6-(2,2,2-trifluoro-ethoxy)-nicotinamide,
6-(4-chloro-phenyl)-5-thiomorpholin-4-yl-pyrazine-2-carboxylic acid ((R)-2-cyclopropyl-2-hydroxy-propyl)-amide,
6-(4-chloro-phenyl)-5-(4,4-difluoro-piperidin-1-yl)-pyrazine-2-carboxylic acid ((R)-2-cyclopropyl-2-hydroxy-propyl)-amide,
6-(4-chloro-phenyl)-5-(2-cyclopropyl-ethyl)-pyrazine-2-carboxylic acid ((R)-2-cyclopropyl-2-hydroxy-propyl)-amide,
5-(2-pyridin-2-yl-ethyl)-6-(4-trifluoromethoxy-phenyl)-pyrazine-2-carboxylic acid ((R)-2-cyclopropyl-2-hydroxy-propyl)-amide,
6-(4-fluoro-phenyl)-5-piperidin-1-yl-pyrazine-2-carboxylic acid ((R)-2-cyclopropyl-2-hydroxy-propyl)-amide,
5-(4-chloro-phenyl)-N-((1R,2R)-2-hydroxy-cyclohexyl)-6-[2-(1-hydroxy-cyclopentyl)-ethyl]-nicotinamide,
6-cyclopropylmethoxy-5-(4-fluoro-phenyl)-N—((R)-3,3,3-trifluoro-2-hydroxy-2-methyl-propyl)-nicotinamide,
5-(4-chloro-phenyl)-6-cyclopropylmethoxy-N-((1R,2R)-2-hydroxy-cyclohexyl)-2-trifluoromethyl-nicotinamide
N—((S)-1-hydroxymethyl-3-methyl-butyl)-5-(3-methoxy-phenyl)-6-pyrrolidin-1-yl-nicotinamide,
N—((S)-1-hydroxymethyl-3-methyl-butyl)-5-(4-methoxy-phenyl)-6-pyrrolidin-1-yl-nicotinamide,
5-(4-chloro-3-methyl-phenyl)-N—((R)-1-hydroxymethyl-3-methyl-butyl)-6-pyrrolidin-1-yl-nicotinamide,
N—((R)-1-hydroxymethyl-3-methyl-butyl)-5-(3-methoxy-phenyl)-6-pyrrolidin-1-yl-nicotinamide,
N—((R)-1-hydroxymethyl-3-methyl-butyl)-5-(4-methoxy-phenyl)-6-pyrrolidin-1-yl-nicotinamide,
N—((R)-1-hydroxymethyl-3-methyl-butyl)-6-pyrrolidin-1-yl-5-(4-trifluoromethyl-phenyl)-nicotinamide,
N—((R)-1-hydroxymethyl-3-methyl-butyl)-6-pyrrolidin-1-yl-5-(4-trifluoromethoxy-phenyl)-nicotinamide, 5-(4-cyano-phenyl)-N—((R)-1-hydroxymethyl-3-methyl-butyl)-6-pyrrolidin-1-yl-nicotinamide,
N-((1R,2R)-2-hydroxy-cyclohexyl)-6-[2-(3-methyl-3H-imidazol-4-yl)-ethyl]-5-(4-trifluoromethyl-phenyl)-nicotinamide,
(R)-2-{[6-(4-fluoro-phenyl)-5-pyrrolidin-1-yl-pyrazine-2-carbonyl]-amino}-3-methyl-butyric acid methyl ester
6-(4-butylcarbamoyl-butoxy)-5-(4-chloro-phenyl)-N-((1R,2R)-2-hydroxy-cyclohexyl)-nicotinamide,
5-[4-(2-butylcarbamoyl-ethyl)-phenyl]-6-cyclopropylmethoxy-N-((1R,2R)-2-hydroxy-cyclohexyl)-nicotinamide,
5-(2,4-dichloro-phenyl)-N-(2-hydroxy-ethyl)-6-propoxy-nicotinamide,
6-cyclopentylmethoxy-5-(2,4-dichloro-phenyl)-N-(2-hydroxy-ethyl)-nicotinamide,
5-(4-chloro-phenyl)-N—((S)-1-hydroxymethyl-3-methyl-butyl)-6-pyrrolidin-1-yl-nicotinamide,
5-(3,4-dichloro-phenyl)-N—((S)-1-hydroxymethyl-3-methyl-butyl)-6-pyrrolidin-1-yl-nicotinamide,
5-(4-chloro-3-methyl-phenyl)-N—((S)-1-hydroxymethyl-3-methyl-butyl)-6-pyrrolidin-1-yl-nicotinamide,
5-(2-fluoro-phenyl)-N—((R)-1-hydroxymethyl-3-methyl-butyl)-6-pyrrolidin-1-yl-nicotinamide,
5-(4-fluoro-phenyl)-N—((R)-1-hydroxymethyl-3-methyl-butyl)-6-pyrrolidin-1-yl-nicotinamide,
5-(3-chloro-phenyl)-N—((R)-1-hydroxymethyl-3-methyl-butyl)-6-pyrrolidin-1-yl-nicotinamide,
5-(4-chloro-phenyl)-N—((R)-1-hydroxymethyl-3-methyl-butyl)-6-pyrrolidin-1-yl-nicotinamide,
5-(3,4-dichloro-phenyl)-N—((R)-1-hydroxymethyl-3-methyl-butyl)-6-pyrrolidin-1-yl-nicotinamide,
3'-(3-chloro-phenyl)-3,4,5,6-tetrahydro-2H-[1,2']bipyridinyl-5'-carboxylic acid ((S)-1-hydroxymethyl-3-methyl-butyl)-amide, and all pharmaceutically acceptable salts thereof.

The invention further relates to new compounds of the formula I having the formula

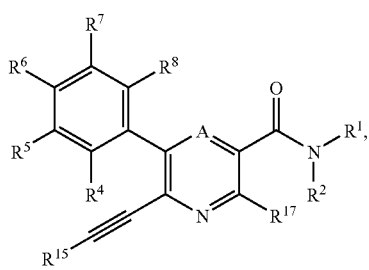

wherein A, $R^1$ to $R^8$, $R^{15}$ and $R^{17}$ are as defined herein before, and pharmaceutically acceptable salts thereof.

Within this group, those compounds of formula I-B are preferred, wherein $R^6$ is chloro and $R^4$, $R^5$, $R^7$ and $R^8$ are hydrogen. Most preferably, the compounds of formula I-B are selected from 5-(5-bromo-furan-2-ylethynyl)-6-(4-chloro-phenyl)-pyrazine-2-carboxylic acid ((R)-2-cyclopropyl-2-hydroxy-propyl)-amide, 5-(4-chloro-phenyl)-N-((1R,2R)-2-hydroxy-cyclohexyl)-6-(3-methoxy-prop-1-ynyl)-nicotinamide, 5-(4-chloro-phenyl)-6-cyclopropylethynyl-N-((1R,2R)-2-hydroxy-cyclohexyl)-nicotinamide, and pharmaceutically acceptable salts thereof.

Compounds of formula I having the formula

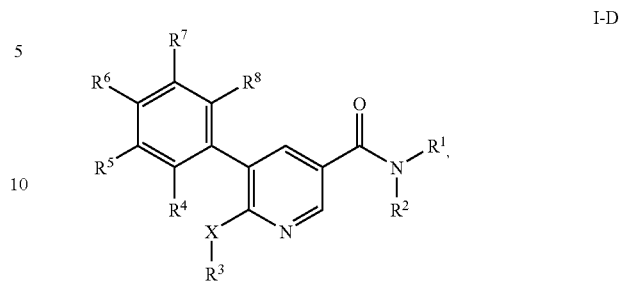

wherein X is O and $R^3$ to $R^8$ are as defined herein before, can be prepared by a process, which process comprises coupling a compound of formula

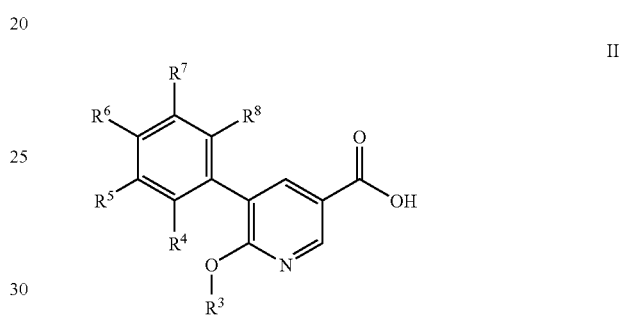

wherein $R^3$ to $R^8$ are as defined herein before, with an amine of the formula $$H—NR^1R^2 \qquad III$$

wherein $R^1$ and $R^2$ are as defined herein before, with the help of an coupling agent under basic conditions, and, if desired, converting the resulting compound of formula I into a pharmaceutically acceptable salt thereof.

Coupling agents for the reaction of compounds of formula II with amines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). Preferred coupling agent is TBTU. Suitable bases include triethylamine, diisopropylethylamine and, preferably, Hünig's base.

Furthermore, compounds of formula I can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The synthesis of compounds with the general structure I, can be accomplished according to the following schemes 1 to 11.

Following the procedure according to scheme 1, compound AA (5-bromo-6-chloro-3-pyridinecarboxylic acid methyl ester, CAS RN 78686-77-8) can be used as starting material. AA is commercially available or can alternatively be prepared by a three step sequence from 6-hydroxy-3-pyridinecarboxylic acid following literature procedures by bromination with bromine in acetic acid, preparation of the 5-bromo-6-chloro-3-pyridine carboxylic acid chloride with phosphorus oxychloride and/or phosphorus pentachloride and solvolysis with methanol.

Compound AC can be prepared from AA by reaction with a suitably substituted primary or secondary alcohol of formula AB or a phenol of formula AB in the presence of a base, for example sodium hydride, in a inert solvent, for example dimethylformamide, at temperatures from room temperature to reflux temperature of the solvent, preferably at room temperature. Compound AE can be prepared by coupling a suitably substituted aryl metal species of formula AD, preferably a arylboronic acid or arylboronic acid ester, with AC in the presence of a suitable catalyst, preferably a palladium catalyst and more preferably palladium(II)acetate/triphenylphosphine mixtures or palladium(II)chloride-dppf (1,1'-bis(diphenylphosphino)ferrocene) complexes and a base, preferably triethylamine or sodium carbonate in an inert solvent such as dimethylformamide or toluene.

Compound AF can then be obtained by saponification of compound AC by methods known in the art, for example by saponification with an alkalimetal hydroxide, for example sodium hydroxide, in a suitable solvent, for example a mixture of dioxane and water.

In the following step compounds of formula I are obtained from compound AF and the corresponding amine of formula AG by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature.

The Suzuki reaction followed by saponification and amide coupling as described in scheme 1 need not necessarily be run in this sequence. An alternative viable sequence would be saponification followed by amide coupling and finally Suzuki reaction.

Scheme 1

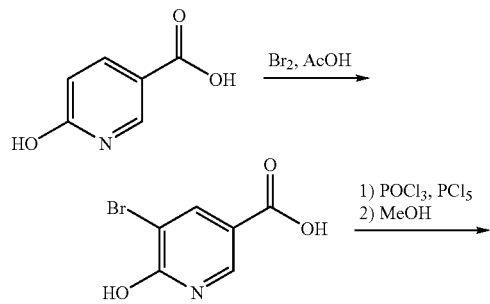

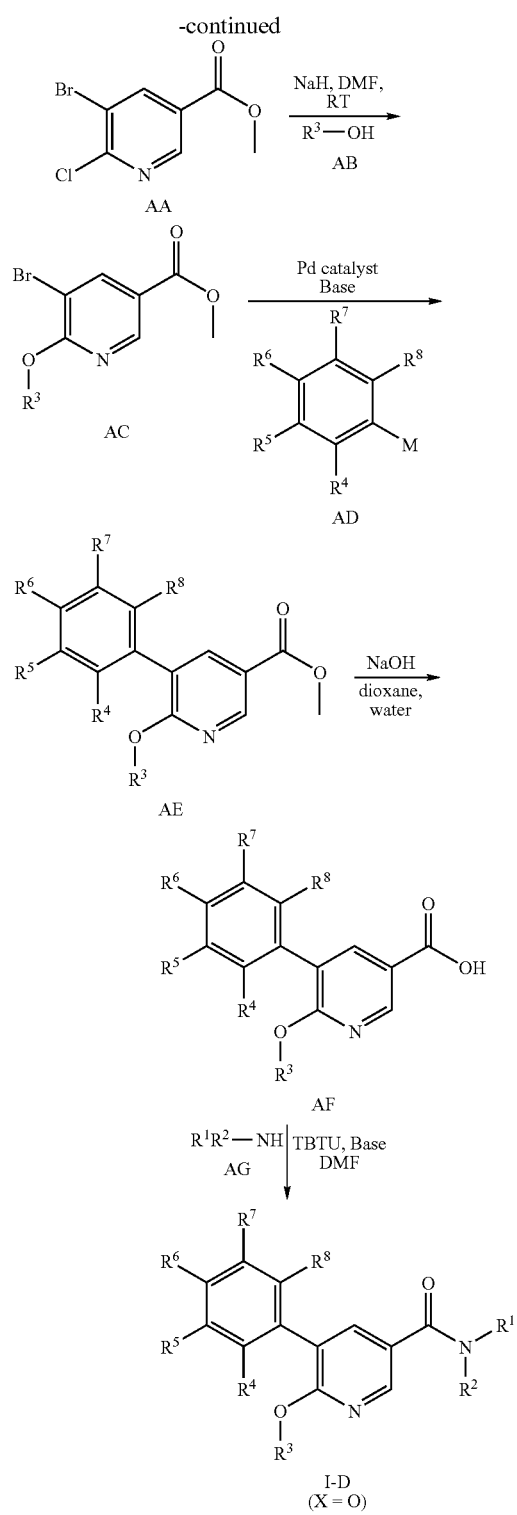

Alternatively, compounds of formula I can be prepared according to scheme 2 starting from compound BA (5-bromo-6-chloro-3-picoline, CAS RN 17282-03-0), which is commercially available or can be prepared starting from 6-hydroxy-3-picoline following literature procedures by bromination with N-bromosuccinimide (NBS) and reaction with phosphorus oxychloride.

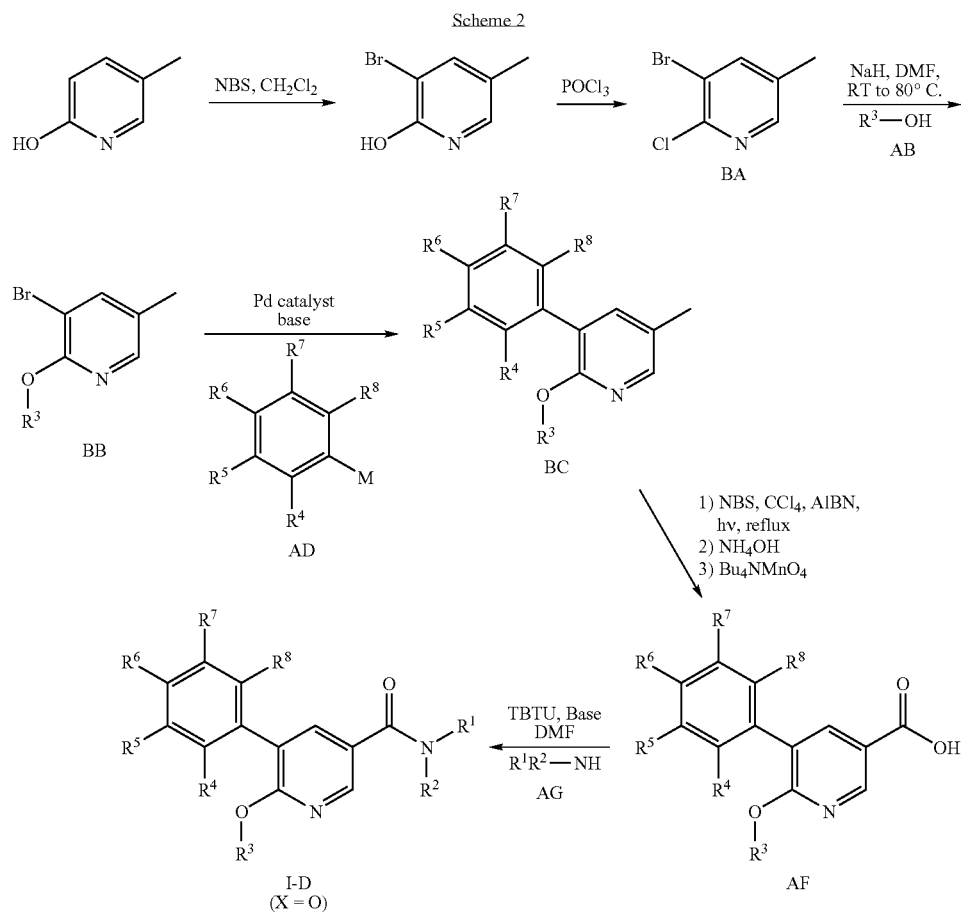

Compound BB is prepared from BA by reaction with a suitably substituted primary or secondary alcohol of formula AB or a phenol of formula AB in the presence of a base, for example sodium hydride, in a inert solvent, for example dimethylformamide, at temperatures from room temperature to reflux temperature of the solvent, preferably at 70° C.

Compound BC can then be prepared by coupling a suitably substituted aryl metal species, preferably a arylboronic acid or arylboronic acid ester of formula AD, with BB in the presence of a suitable catalyst, preferably a palladium catalyst and more preferably palladium(II)chloride-dppf complexes and a base, preferably sodium carbonate in an inert solvent such as toluene.

Starting from BC compound AD can be obtained by direct or multistep oxidation of the methyl group by methods known in the art as for example those reviewed in March, Advanced Organic Chemistry, 5th ed. 2001, Wiley & Sons. More specifically compound BC can be brominated with N-bromosuccinimide (NBS) in the presence of a radical chain initiator as for example azo-bisisobutyronitrile (AIBN) in an inert solvent, for example carbon tetrachloride, by irradiating and heating, saponification of the produced mono- or dibromide with for example ammonium hydroxide to the aldehyde or alcohol and finally by oxidation with a suitable oxidizing agent, for example tetrabutylammonium permanganate, in an inert solvent such as pyridine.

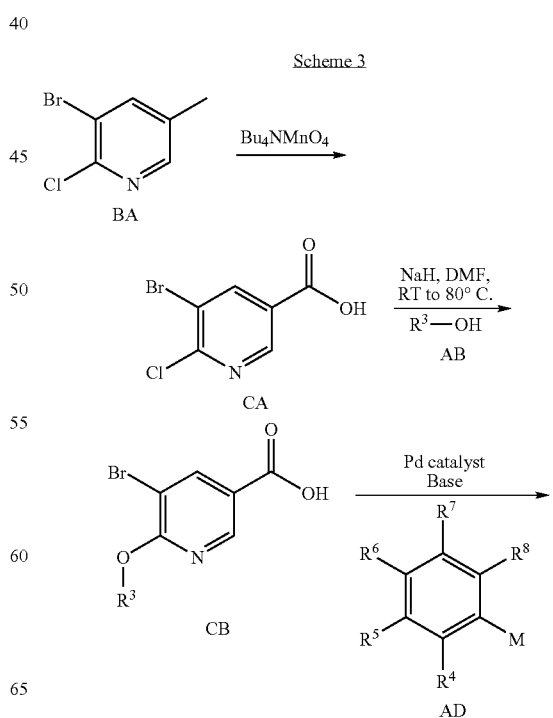

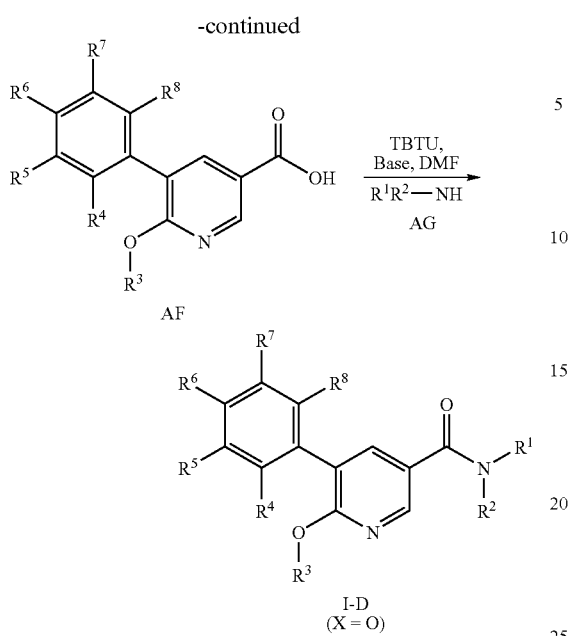

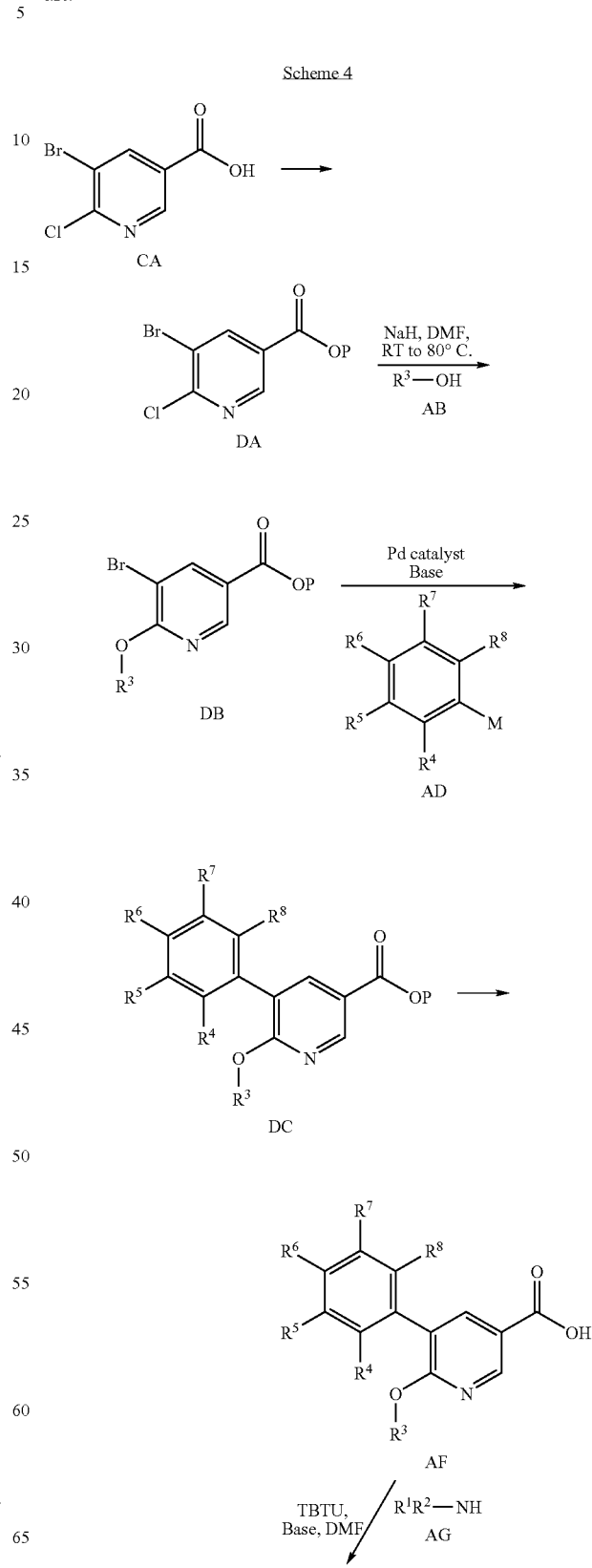

sodium carbonate in an inert solvent such as toluene, a compound DC is obtained. Compound AF can in turn be prepared by de-protection of compound DC by methods known in the art.

Alternatively, compounds of formula I can be prepared according to scheme 3 starting from compound CA (5-bromo-6-chloro-3-pyridinecarboxylic acid, CAS RN 29241-62-1) which is commercially available or can be obtained by literature methods or by oxidation of compound BA with tetrabutylammonium permanganate in pyridine.

Compound CB is obtained from compound CA by reaction with a suitably substituted primary or secondary alcohol of formula AB or a phenol of formula AB in the presence of two or more equivalents of a base, for example sodium hydride, in a inert solvent, for example dimethylformamide, at temperatures from room temperature to reflux temperature of the solvent, preferably at 70° C.

Compound AF can then be prepared by coupling a suitably substituted aryl metal species, preferably a arylboronic acid or arylboronic acid ester of formula AD, with CB in the presence of a suitable catalyst, preferably a palladium catalyst and more preferably palladium(II)chloride-dppf complexes, and a base, preferably sodium carbonate in an inert solvent such as toluene. Alternatively, compounds of formula I can be prepared starting from compound CA by protecting the acid group with a suitable protecting group (P) to give compound DA by methods known in the art (Scheme 4). Suitable acid protecting groups are for example benzyl (Bn), benzyloxymethyl (BOM), methoxyethoxymethyl (MEM) or allyl groups and silyl groups such as trimethylsilyl, triethylsilyl and tert-butyldimethylsilyl esters (for more details see T. W. Greene et al., Protective Groups in Organic Chemistry, John Wiley and Sons Inc. New York 1999, 3$^{rd}$ edition).

Compound DB can be prepared from DA by reaction with a suitably substituted primary or secondary alcohol of formula AB or a phenol of formula AB in the presence of a base, for example sodium hydride, in a inert solvent, for example dimethylformamide, at temperatures from room temperature to reflux temperature of the solvent, preferably at room temperature. By coupling a suitably substituted aryl metal species, preferably a arylboronic acid or arylboronic acid ester of formula AD, with DB in the presence of a suitable catalyst, preferably a palladium catalyst and more preferably palladium(II)chloride-dppf complexes, and a base, preferably

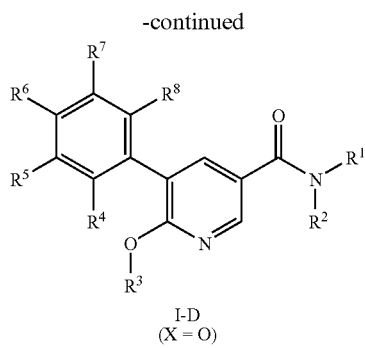

I-D
(X = O)

Alternatively, compounds of formula I can be prepared according to scheme 5. Following the procedure according to scheme 5, compound AA (5-bromo-6-chloro-3-pyridinecarboxylic acid methyl ester, CAS RN 78686-77-8) can be used as starting material. AA is commercially available or can alternatively be prepared by a three step sequence from 6-hydroxy-3-pyridinecarboxylic acid following literature procedures by bromination with bromine in acetic acid, preparation of the 5-bromo-6-chloro-3-pyridine carboxylic acid chloride with phosphorus oxychloride and/or phosphorus pentachloride and solvolysis with methanol.

Compound EB can be prepared from AA by reaction with a suitably substituted primary or secondary amine formula EY in the presence of a base, for example DBU, in either an inert solvent, for example dimethylformamide, or in neat DBU at temperatures from room temperature to reflux temperature of the solvent, preferably at room temperature.

Compound ED can be prepared by coupling a suitably substituted aryl metal species of formula EC, preferably a arylboronic acid or arylboronic acid ester, with EB in the presence of a suitable catalyst, preferably a palladium catalyst and more preferably palladium(II)acetate/triphenylphosphine mixtures or palladium(II)chloride-dppf (1,1'-bis(diphenylphosphino)ferrocene) complexes and a base, preferably triethylamine or sodium carbonate in an inert solvent such as dimethylformamide or toluene.

Compound EF can then be obtained by saponification of compound ED by methods known in the art, for example by saponification with an alkalimetal hydroxide, for example sodium hydroxide, in a suitable solvent, for example a mixture of dioxane and water.

In the following step compounds of formula I are obtained from compound EF and the corresponding amine of formula AG by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature.

Scheme 5

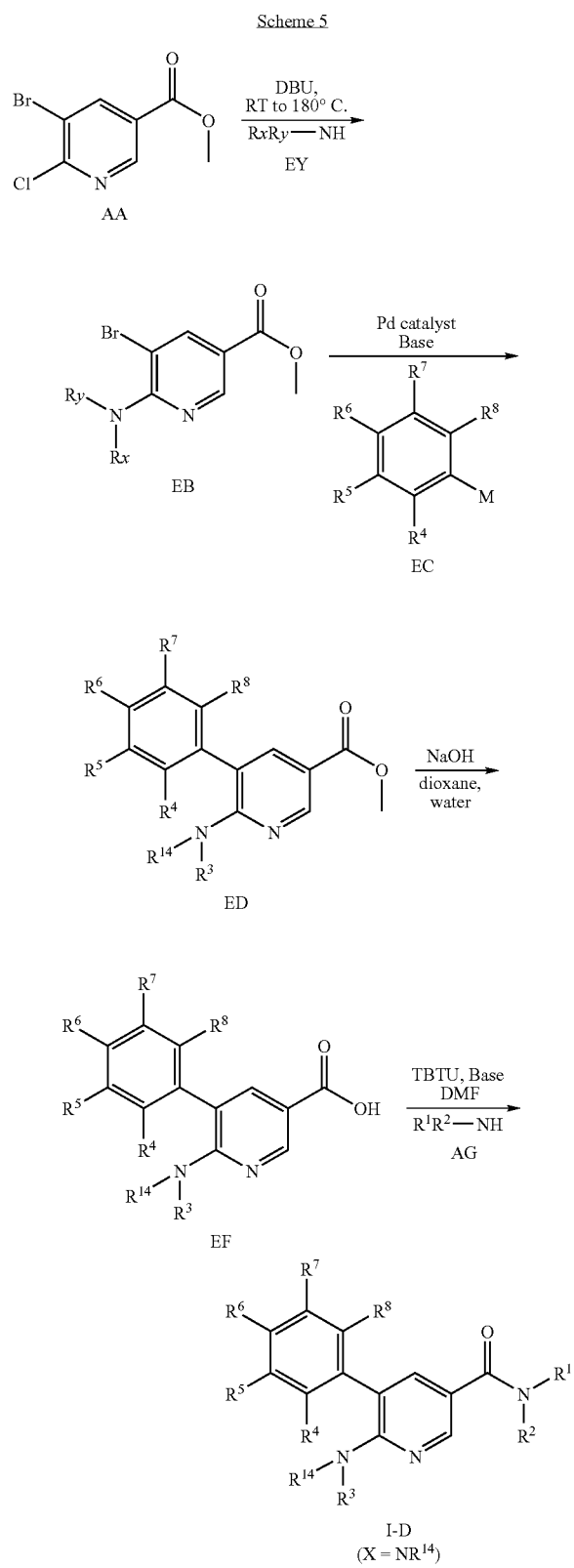

Alternatively, compounds of formula I, wherein A is N, can be prepared by a process, which process comprises coupling a compound of formula

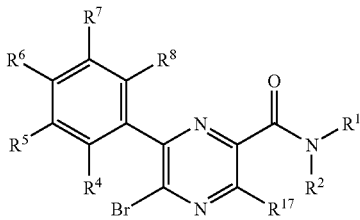

wherein $R^1$, $R^2$, $R^4$ to $R^8$ and $R^{17}$ are as defined herein before, with an amine of the formula $$H—NR^3R^{14} \qquad V$$

wherein $R^3$ and $R^{14}$ are as defined herein before, with the help of an activating agent under basic conditions, and, if desired, converting the resulting compound of formula I into a pharmaceutically acceptable salt thereof.

Activating agents include coupling agents for the reaction of compounds of formula IV with amines of formula V as for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU).

Suitable bases include triethylamine, diisopropylethylamine and, preferably, Hünig's base.

Alternatively, compounds of formula I wherein A is N can be prepared by a process, which process comprises coupling a compound of formula

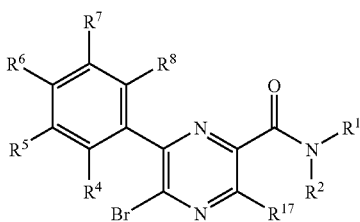

wherein $R^1$, $R^2$, $R^4$ to $R^8$ and $R^{17}$ are as defined herein before, with an alcohol of the formula $$R^3—OH \qquad VI$$

wherein $R^3$ is as defined herein before, in the presence of a metal hydride or metal carbonate, and, if desired, converting the resulting compound of formula I into a pharmaceutically acceptable salt thereof.

Preferably, the metal hydride is sodium hydride. Preferred metal carbonate is cesium carbonate.

The synthesis of compounds with the general formula I wherein A is N, can be accomplished according to the following schemes 6 to 8.

A compound of formula FA can be transformed to a compound of formula FB by reaction with aryl boronic acids (exemplified but by no means restricted to phenylboronic acid; 4-fluorophenylboronic acid; 4-chlorophenylboronic acid, (4-trifluoromethyl)phenylboronic acid or 4-trifluoromethoxyphenylboronic acid) in an appropriate solvent such as 1,2-dimethoxyethane in the presence of a suitable catalyst such as tetrakis(triphenylphosphine) palladium (0) and a suitable base such as sodium carbonate at temperatures typically ranging from 0° C. to 120° C.; a protocol commonly known as the Suzuki reaction.

Transformation of a compound of the formula FB to a compound of formula FC can be effected by palladium catalyzed insertion of carbon monoxide into the aryl-bromine bond in a solvent containing an alcohol such as methanol under an atmosphere of carbon monoxide at pressures typically ranging from 1 bar to 200 bar and temperatures typically ranging from 20° C. to 150° C.

Scheme 6

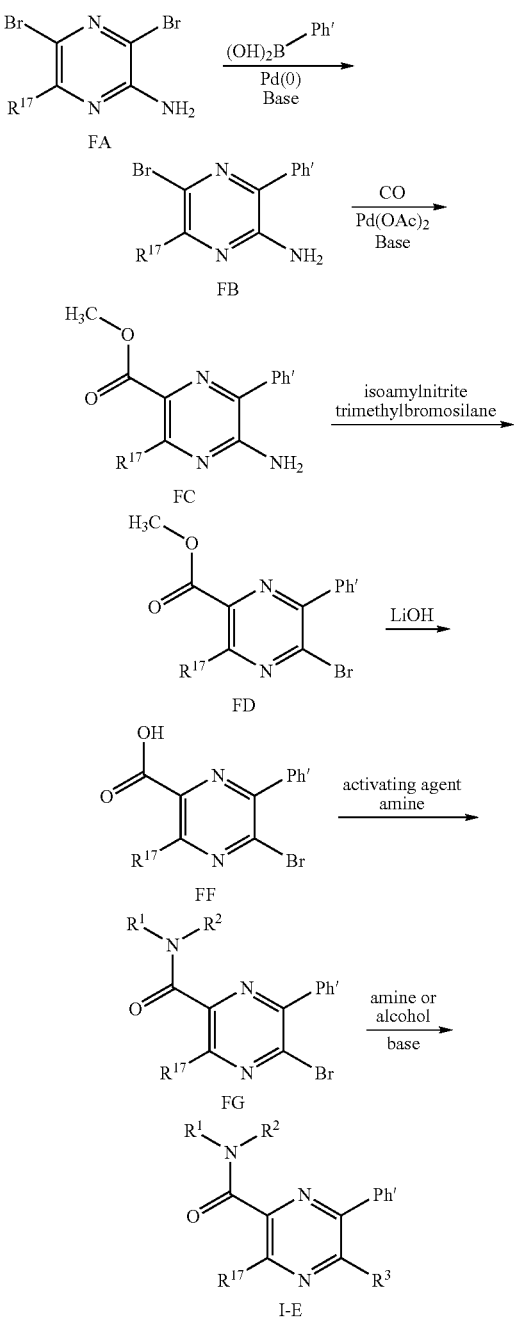

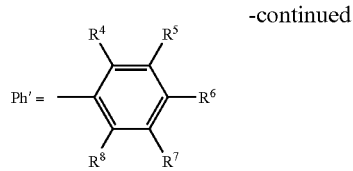

Compounds of the formula FC can be converted to compounds of the formula FD by reaction with a source of nitrite, preferably isoamyl nitrite in the presence of a source of bromide such as metal bromides or bromine containing solvents ence of a suitable base, preferably an excess of the amine itself or tertiary amine bases exemplified by triethylamine, Huenig's base or N,N,N',N'-tetramethylguanidine, in the case of reaction with amines or in case of reaction with alcohols, in presence of suitable bases such as metal hydrides, preferably sodium hydride or metal carbonates such as cesium carbonate to yield compounds of the general formula I-E.

Saponification, amide coupling and reaction with amines or alcohols as described in scheme 6 needs not necessarily to be run in this sequence. An alternative viable sequence would be reaction with amines or alcohols, followed by saponification and finally amide coupling.

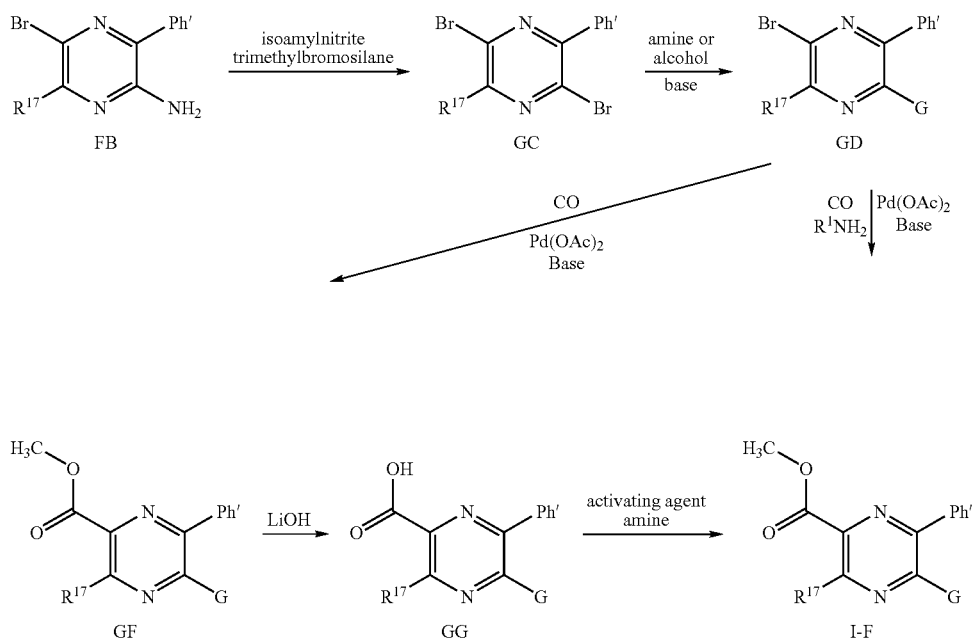

Scheme 7 such as dibromo-methane and an activating agent such as hydrobromic acid or trimethylbromosilane at temperatures ranging from −20° C. to 80° C., typically at ambient temperature.

Saponification of compounds of the formula FD to compounds of the formula FF can be carried out in the presence of a suitable base such as a metal hydroxide, preferably lithium hydroxide, in an appropriate solvent such as tetrahydrofuran and mixtures thereof with water at temperatures ranging from 0° C. to 100° C., preferably at 20° C.

Coupling of compounds of the general formula FF with amines to give compounds of the general formula FG can be carried out by methods used for the formation of peptide bonds. In one particular aspect of the invention compounds of the general formula V can be converted to their acid chlorides by reaction with (1-chloro-2-methyl-propenyl)-dimethyl-amine in an inert solvent such as dichloromethane and subsequently coupled to amines in the presence of suitable bases such as triethylamine or Huenig's base.

Compounds of the general formula FG can be reacted with a wide variety of alcohols and amines in suitable solvents such as dimethylformamide or dimethylsulfoxide in the pres- Alternatively, compounds of the general formula FB can be transformed to compounds of the general formula GC by essentially the same conditions as described above for the conversion of compounds of the general formula FC to compounds of the general formula FD Compounds of formula GC can be reacted with amines or alcohols under conditions described above for conversion of compounds of formula FG to compounds of formula I-F yielding preferentially compounds of formula GD. Further transformation of the compounds of the general formula GD to compounds of the general formula I-F can be accomplished via intermediates of the general formula GG, and compounds of the general formula GG using the methods described for the transformation of compounds of the general formula FB to compounds of the general formula FC and of compounds of the general formula FD to compounds of the general formula FG via compounds of the general formula FF.

In a further aspect of the invention compounds of the general formula GD can be transformed to compounds of the general formula I-F directly by palladium catalyzed carbonylation in the presence of appropriate amines under condition otherwise similar to the above described transformations of compounds of the general formula FB to compounds of the general formula FC.

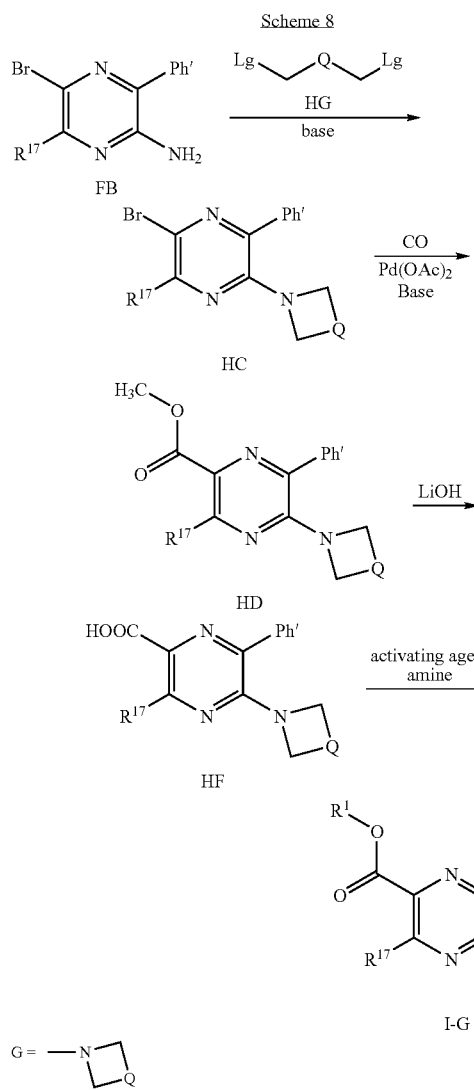

Scheme 8

G = —N⟨Q⟩

Compounds of the general formula FB can be transformed into compounds of the general formula HC by reaction with compounds of the general formula HG in which the abbreviation Lg stands for a suitable leaving group such as a halogen group or a mesylate group and Q stands for a carbon chain consisting of 2 to 3 methylene units or a chain consisting of a methylene unit an oxygen atom and an other methylene unit. Further transformation into compounds of the general formula I-G can be carried out in analogy to the transformation of compounds of the general formula GD to compounds of the general formula I-G.

Compounds of formula I can also be prepared according to scheme 9 starting from compound AA by regioselective arylation using a suitable arylmetalspecies and catalyst system in an inert solvent to give an intermediate IB. Advantageously such a arylmetalspecies might be an arylboronic acid which is reacted with AA in a inert solvent, for example toluene, in the presence of a palladium catalyst, for example tetrakis(triphenylphosphine)palladium(0) or bis(diphenylphoshinofer- rocene)dichloropalladium(II), and a base, like sodium carbonate, at temperatures ranging from room temperature to the boiling point of the solvent.

Saponification of compounds of the formula IB to give compounds of the formula IC can be carried out in the presence of a suitable base such as a metal hydroxide, preferably lithium hydroxide, in an appropriate solvent such as tetrahydrofuran and mixtures thereof with water or methanol at temperatures ranging from 0° C. to 100° C., preferably at 20° C.

Coupling of compounds of the general formula IC with amines to give compounds of the general formula ID can be carried out by methods used for the formation of peptide bonds. In one particular aspect of the invention compounds of the general formula ID are activated with a coupling reagent, for example TBTU (O-benzotriazol-1-yloxy)-N,N,N',N'-tetramethyluronium tetrafluoroborate), and coupled to amines in an inert solvent such as DMF in the presence of suitable bases such as triethylamine or Huenig's base.

Compounds of the general formula ID can be transformed into compounds of the general formula IE by reaction with alkinyls of the general formula XB. Advantageously this reaction is run in the presence of a suitable catalyst system, for example bis(diphenylphoshinoferrocene)dichloropalladium (II), cuprous(I)iodide and triphenylphosphine on polystyrene in the presence of a suitable base, for example diisopropylethylamine or diethylamine, in a inert solvent, for example tetrahydrofuran or dimethylformamide in a microwave oven at 120° C.

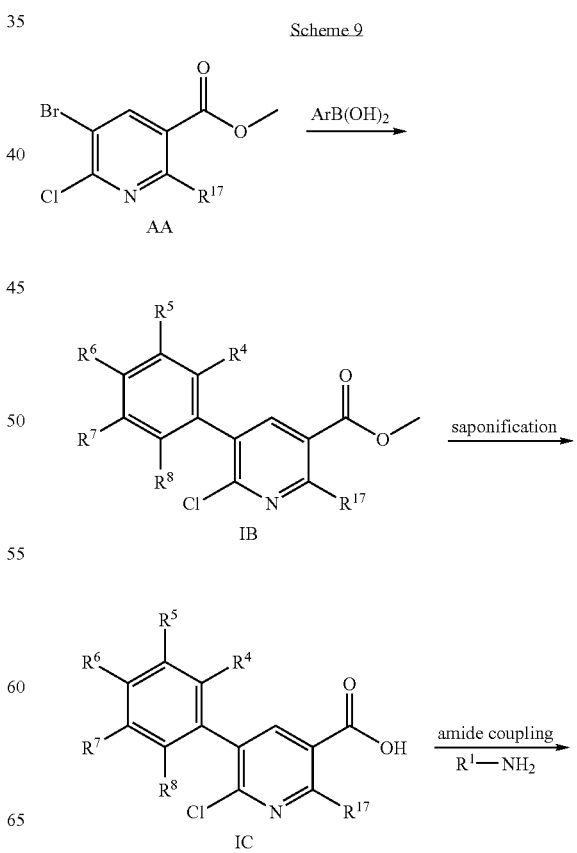

Scheme 9

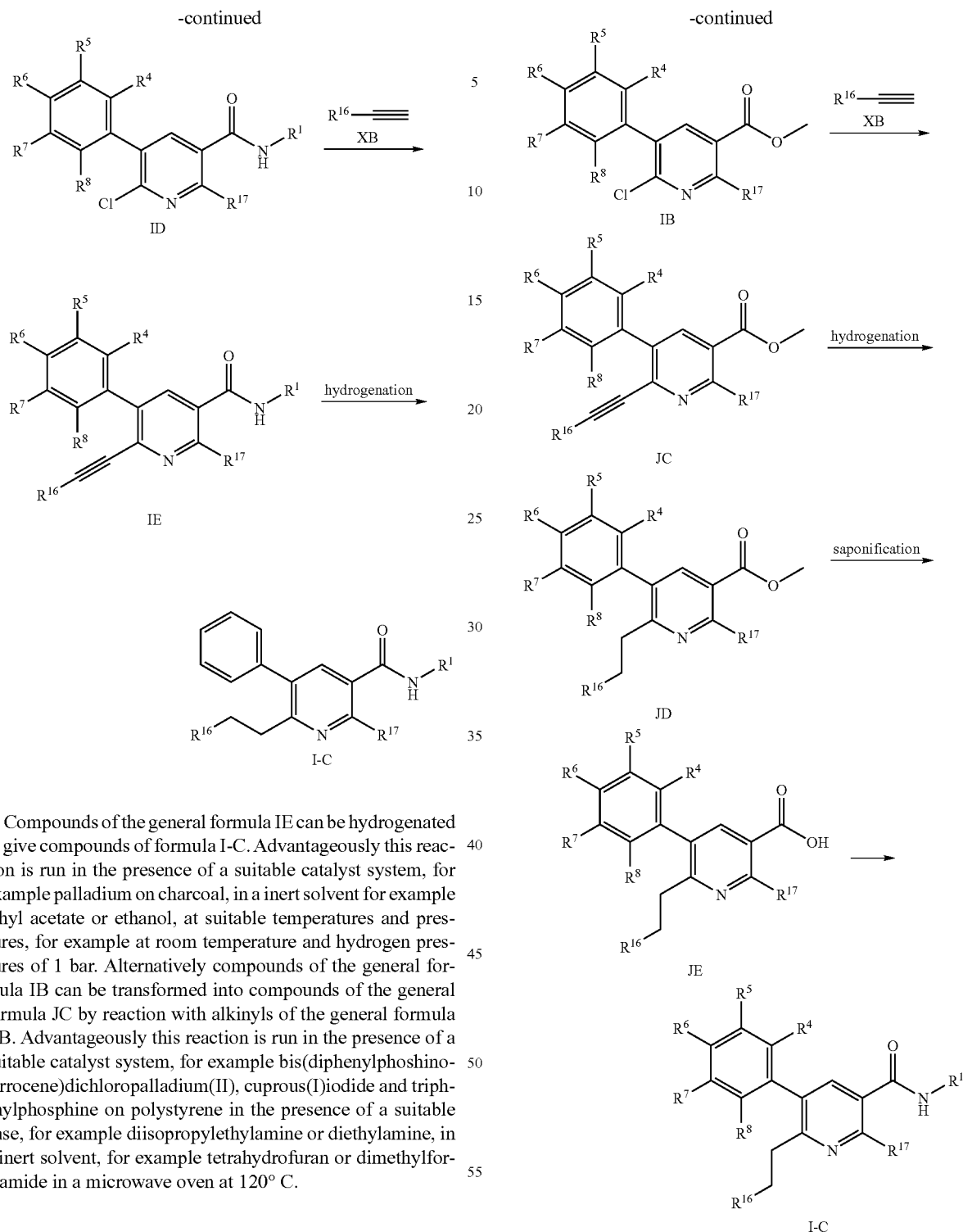

Compounds of the general formula IE can be hydrogenated to give compounds of formula I-C. Advantageously this reaction is run in the presence of a suitable catalyst system, for example palladium on charcoal, in a inert solvent for example ethyl acetate or ethanol, at suitable temperatures and pressures, for example at room temperature and hydrogen pressures of 1 bar. Alternatively compounds of the general formula IB can be transformed into compounds of the general formula JC by reaction with alkinyls of the general formula XB. Advantageously this reaction is run in the presence of a suitable catalyst system, for example bis(diphenylphoshino-ferrocene)dichloropalladium(II), cuprous(I)iodide and triphenylphosphine on polystyrene in the presence of a suitable base, for example diisopropylethylamine or diethylamine, in a inert solvent, for example tetrahydrofuran or dimethylformamide in a microwave oven at 120° C.

Scheme 10

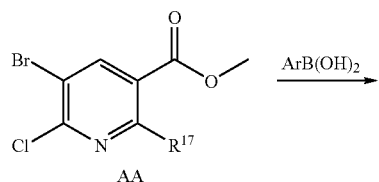

Compounds of the general formula JC can be hydrogenated to give compounds of formula JD. Advantageously this reaction is run in the presence of a suitable catalyst system, for example palladium on charcoal, in an inert solvent for example ethyl acetate or ethanol, at suitable temperatures and pressures, for example at room temperature and hydrogen pressures of 1 bar.

Saponification of compounds of the formula JD to give compounds of the formula JE can be carried out in the presence of a suitable base such as a metal hydroxide, preferably lithium hydroxide, in an appropriate solvent such as tetrahydrofuran and mixtures thereof with water or methanol at temperatures ranging from 0° C. to 100° C., preferably at 20° C.

Coupling of compounds of the general formula JE with amines to give compounds of the general formula I-C can be carried out by methods used for the formation of peptide bonds. In one particular aspect of the invention compounds of the general formula JE are activated with a coupling reagent, for example TBTU (O-benzotriazol-1-yloxy)-N,N,N',N'-tetramethyluronium tetrafluoroborate), and coupled to amines in an inert solvent such as DMF in the presence of suitable bases such as triethylamine or Huenig's base.

Compounds of the general formula XB can, if $R^{16}$ represents an aryl-group, be prepared according to Scheme 11. An aryl bromide of formula X is coupled in a Sonogashira type reaction with (trimethylsilyl)acetylene using a suitable catalyst system, for example tetrakis(triphenylphosphine)palladium(0) and cuprous(I)iodide, in an inert solvent, for example toluene, in the presence of a base, for example diisopropylamine, at elevated temperatures, for example 60° C., to give a compound of formula XA.

Deprotection of a compound of formula XA to give a compound of formula XB, can be achieved with a base, for example potassium carbonate, in a suitable solvent, for example methanol, at room temperature.

Scheme 11

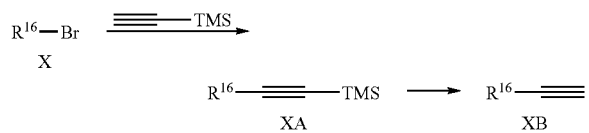

It will be appreciated, that the compounds of formula I in this invention may be derivatised at functional groups to provide derivatives which are capable of conversion back to the parent compound in vivo.

As described above, the compounds of formula I of the present invention can be used as medicaments or pharmaceutical compositions for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia is preferred.

The invention therefore also relates to a pharmaceutical composition comprising a compound as defined above and a pharmaceutically acceptable carrier and/or adjuvant which are useful for the treatment and/or prophylaxis of diseases which can be treated with HDL-cholesterol raising agents.

Thus, the invention relates to a pharmaceutical composition as defined above for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

In addition, the invention relates to the use of compounds of formula I as defined above for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of pharmaceutical compositions for the treatment and/or prophylaxis of dyslipidemia is preferred.

In addition, HDL raising agents of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The invention therefore also relates to a pharmaceutical composition comprising a compound of formula I as defined above in combination or association with a compound selected from the group consisting of an HMG-CoA reductase inhibitor, an microsomal triglyceride transfer protein (MTP)/ApoB secretion inhibitor, aPPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant for the preparation of a medicament for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

The invention also relates to a method for the treatment and/or prophylaxis of diseases which can be treated with HDL-cholesterol raising agents, which method comprises administration of a therapeutically effective amount of a compound according to formula I in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is preferred.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, preferably 5-50 mg, of a compound of formula I.

In the following examples the tests that were carried out in order to determine the activity of the compounds of formula I and especially their valuable pharmacological properties are described.

EXAMPLES

The following are a list of abbreviations and/or acronyms with their corresponding definitions used in the following examples:

MS=mass spectrometry; EI=electron impact; ISP=ion spray, corresponds to ESI (electrospray); NMR data are reported in parts per million ($\delta$) relative to internal tetramethylsilane and are referenced to the deuterium lock signal from the sample solvent ($d_6$-DMSO unless otherwise stated); coupling constants (J) are in Hertz, mp=melting point; bp=boiling point; HPLC=LC=high performance liquid chromatography, Rt=retention time, TLC=thin layer chromatography, RT=room temperature, TBTU=O-(Benzotriazol-1-yl)-N,N',N'-tetramethyl-uronium-tetrafluoroborate; DMA=dimethylacetamide, DMF=dimethylformamide, DBU=1,8-diazabicyclo[5.4.0]undec-7-ene, DIPEA=diisopropylethylamine, CAN=CAS Registry Number.

Example 1

Effects on Plasma Lipid Levels in Lean, Chow Fed Rats

Effects of compounds of formula I on plasma lipid levels were determined in lean, chow-fed male Sprague-Dawley rats with compounds administered by p.o. gavage. After one week of acclimation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using calorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve (AUC). Compound concentration was also determined in plasma.

TABLE 1

HDL cholesterol levels in lean, chow fed rats

| Compound | HDL Cholesterol levels [AUC as % compared to control] @ 30 mg/kg p.o. of compound |
| --- | --- |
| 5-(4-Chloro-phenyl)-6-cyclopropylmethoxy-N-((1R,2R)-2-hydroxy-cyclohexyl)-nicotinamide | +30% |
| N-((R)-2-Cyclopropyl-2-hydroxy-propyl)-6-cyclopropylmethoxy-5-(4-fluoro-phenyl)-nicotinamide | +73% |
| 5-(4-Chloro-phenyl)-N-((1R,2R)-2-hydroxy-cyclohexyl)-6-(2,2,2-trifluoro-ethoxy)-nicotinamide | +78% |
| 6-Cyclopropylmethoxy-5-(4-fluoro-phenyl)-N-((1R,2R)-2-hydroxy-cyclohexyl)-nicotinamide | +35% |

Example 2

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g. liver, fat). Total cholesterol, HDL-cholesterol, and triglycerides were determined by measuring total cholesterol, HDL-cholesterol and triglyceride using calorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve (AUC). Compound concentration was also determined in plasma.

TABLE 2

HDL cholesterol levels in obese, high fat diet fed rats

| Compound | HDL Cholesterol levels [AUC as % compared to control] @ 30 mg/kg food admix of compound* |
| --- | --- |
| 5-(4-Chloro-phenyl)-N-((1R,2R)-2-hydroxy-cyclohexyl)-6-(2-methoxy-ethoxy)-nicotinamide | +50% ($p < 0.01$) |
| 5-(4-Chloro-phenyl)-6-cyclopropylmethoxy-N-((1R,2R)-2-hydroxy-cyclohexyl)-nicotinamide | +84% ($p < 0.01$) |
| Rimonabant, *@ 10 mg/kg food admix | +11% (ns) |

Example 3

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using calorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

TABLE 3

HDL cholesterol levels in hamsters

| Compound | HDL Cholesterol levels [AUC as % compared to control] @ 30 mg/kg po of compound |
| --- | --- |
| 5-(4-Chloro-phenyl)-N-((1R,2R)-2-hydroxy-cyclohexyl)-6-(2,2,2-trifluoro-ethoxy)-nicotinamide | +69% |

Example 4

Effects on Plasma Lipid Levels in Cholesterol/Fat Fed Hamsters

Efficacy of compounds in modulating plasma lipid levels was also determined in cholesterol/fat fed hamsters. The protocol is identical as described above except that animals are fed with chow diet enriched with 10% (w/w) saturated fat and 0.05% (w/w) cholesterol. Animals received this high fat diet 2 weeks before starting compound administration and continued this diet throughout the study. The 2 weeks pre-treatment induced an increase in plasma cholesterol and triglyceride levels allowing a better assessment of LDL-C and triglyceride changes.

Example 5

Preparation of 5-(4-chloro-phenyl)-6-cyclopropyl-methoxy-N-((1R,2R)-2-hydroxy-cyclohexyl)-nicotinamide a) 6-Chloro-5-(4-chloro-phenyl)-Nicotinic Acid Methyl Ester

5-Bromo-6-chloro-3-pyridinecarboxylic acid methyl ester (42.2 g, 0.169 mol, CA 78686-77-8) was dissolved in toluene (840 mL). To this solution was added with stirring [1,1'-bis(diphenylphosphino)ferrocene]dichloropalladium(II)

CH$_2$Cl$_2$ (6.9 g, 8.4 mmol), 4-chlorophenylboronic acid (27.2 g, 0.169 mol) and sodium carbonate solution (2M, 170 mL). This mixture was heated to 90° C. for 1 h and cooled to room temperature. Water (400 mL) was added, the phases were separated and the water mixture was extracted with ethylacetate. Organic phases were pooled, dried with MgSO4 and the volatiles removed in vacuo. The residue was purified by flash chromatography (SiO$_2$, heptane/CH$_2$Cl$_2$) to give the title compound (30.9 g) as a white solid; MS (EI) 281.1, 283.0 (M)$^+$.

b) 6-Chloro-5-(4-chloro-phenyl)-nicotinic Acid

6-Chloro-5-(4-chloro-phenyl)-nicotinic acid methyl ester (30.9 g, 0.11 mol) was dissolved in a mixture of tetrahydrofuran (750 mL) and water (250 mL). Lithiumhydroxid monohydrate (13.8 g, 0.33 mol) was added and the mixture was stirred and heated at reflux-temperature for 1 h. After cooling to room temperature the mixture was acidified with hydrochloric acid (2N, 240 mL) and extracted with methyl-t-butylether. Organic phases were pooled, dried with MgSO$_4$ and the mixture concentrated in vacuo. The title compound crystallized from the concentrated solution as a white solid (quant.); MS (ISP) 266.0 (M–H)

c) 5-(4-Chloro-phenyl)-6-cyclopropylmethoxy-nicotinic Acid

6-Chloro-5-(4-chloro-phenyl)-nicotinic acid (22.3 g, 0.083 mol) was dissolved in dimethylsulfoxide (130 mL). To this solution was added (hydroxymethyl)cyclopropane (10.1 g, 0.125 mol) and potassium hydroxide powder (18.7 g, 0.333 mol). This mixture was reacted (in ten portions) for 20 min in a microwave at 100° C. The reaction mixture was poured into ice-water (500 mL) and citric acid (10%, 3000 mL) was added with stirring. Stirring was continued for 30 min during which time the product precipitated. The product was filtered off washed with water and dissolved in ethylacetate (1500 mL). The solution was concentrated in vacuo and the title compound crystallized from the concentrated solution as a white solid (21.5 g); MS (ISP) 302.2 (M–H)

d) 5-(4-Chloro-phenyl)-6-cyclopropylmethoxy-N-((1R,2R)-2-hydroxy-cyclohexyl)-nicotinamide 5-(4-Chloro-phenyl)-6-cyclopropylmethoxy-nicotinic acid (21.5 g, 0.071 mol) was dissolved in DMF (655 mL). To the solution was added TBTU (25 g, 0.078 mol), N,N-diisopropylethyl amine (60.5 mL, 0.35 mol) and (1R,2R)-2-amino-cyclohexanol (11.8 g, 0.078 mol). The reaction mixture was stirred for 16 h at room temperature. The solvent was evaporated in vacuo and the residue was purified by column chromatography on silica (n-heptane/ethyl acetate gradient) to yield 21.7 g of the title compound as a white solid, MS (ISP) 401.2 (M+H)$^+$.

Example 6

Preparation of 5-(4-chloro-phenyl)-N-((1R,2R)-2-hydroxy-cyclohexyl)-6-(2-methoxy-ethoxy)-nicotinamide a) 5-Bromo-6-(2-methoxy-ethoxy)-nicotinic Acid Methyl Ester 5-Bromo-1,6-dihydro-6-oxo-3-pyridinecarboxylic acid methyl ester (15 g, 65 mmol, CA 381247-99-0) was suspended in THF (500 mL). To this suspension was added with stirring 2-methoxyethanol (7.1 mL, 97 mmol), diisopropylazodicarboxylate (21.5 mL, 97 mmol) and triphenylphosphine (25.4 g, 97 mmol). This mixture was stirred for 1 h at room temperature and the solvent was removed in vacuo. The residue was purified by flash chromatography on silica (heptane/ethylacetate, 2:1) to give the title compound (8.65 g) as a yellow solid; MS (ISP) 290.1 (M+H)$^+$.

b) 5-(4-Chloro-phenyl)-6-(2-methoxy-ethoxy)-nicotinic Acid Methyl Ester

5-Bromo-6-(2-methoxy-ethoxy)-nicotinic acid methyl ester (8.7 g, 29 mmol) was dissolved in toluene (85 mL). To this solution was added with stirring [1,1'-bis(diphenylphosphino)ferrocene]dichloropalladium(II) CH$_2$Cl$_2$ (1.2 g, 1.4 mmol), 4-chlorophenylboronic acid (4.9 g, 29 mmol) and sodium carbonate solution (2M, 30 mL). This mixture was heated to 90° C. for 1.5 h and cooled to room temperature. Water (150 mL) was added, the phases were separated and the water mixture was extracted with ethylacetate. Organic phases were pooled, dried with MgSO4 and the volatiles removed in vacuo. The residue was purified by flash chromatography on silica (heptane/ethylacetate, 1:3) to give the title compound (5.3 g) as a pinkish solid; MS (ISP) 322.1 (M+H)$^+$.

c) 5-(4-Chloro-phenyl)-6-(2-methoxy-ethoxy)-nicotinic Acid

The title compound was synthesized in analogy to Example 5c, using 5-(4-chloro-phenyl)-6-(2-methoxy-ethoxy)-nicotinic acid methyl ester as starting material, MS (ISP) 306.2 (M–H)$^+$.

d) 5-(4-Chloro-phenyl)-N-((1R,2R)-2-hydroxy-cyclohexyl)-6-(2-methoxy-ethoxy)-nicotinamide The title compound was synthesized in analogy to Example 5d, using 5-(4-chloro-phenyl)-6-(2-methoxy-ethoxy)-nicotinic acid and (1R,2R)-2-amino-cyclohexanol as starting materials, MS (ISP) 405.2, 407.2 (M+H)$^+$.

Example 7

Preparation of N—((R)-2-cyclopropyl-2-hydroxy-propyl)-6-cyclopropylmethoxy-5-(4-fluoro-phenyl)-nicotinamide a) 2-Cyclopropyl-2-trimethylsilanyloxy-propionitrile To a well stirred mixture of cyclopropylmethylketone (27.8 mL, 0.3 mol), trimethylsilylcyanide (55.8 mL, 0.45 mol) and 18-crown-6 (4.87 g, 18.5 mmol) was added potassium cyanide (2.44 g, 37.5 mmol). The temperature rose to ~100° C. and stirring was continued for 1 h with heating to 145° C. After cooling the mixture was purified by silicagel chromatography (500 g silica, heptane/ethylacetate 6:1) to yield 47.1 g of the title compound as light brown oil, $^1$H NMR (CDCl$_3$): 0.23 (s, 9H), 0.56 (m, 4H), 1.17 (m, 1H), 1.63 (s, 3H, CH$_3$).

b) α-(Acetyloxy)-α-methyl-cyclopropaneacetonitrile

To a well stirred and ice-cooled solution of 2-cyclopropyl-2-trimethylsilanyloxy-propionitrile (188.5 g, 1.03 mol) in acetonitrile (1000 mL) was added acetic anhydride (194 mL, 2.06 mol) and scandium trifluoromethanesulfonate (5 g, 10.3 mmol). The temperature rose to ~10° C. and stirring was continued for 15' at room temperature. The solvent was evaporated in vacuo and the residue was distilled to yield 138 g of the title compound as colorless liquid, bp: 84-86° C./6 mbar.

c) (R)-α-(Acetyloxy)-α-methyl-cyclopropaneacetonitrile (Warning: Highly toxic hydrogen cyanide is formed in the experiment; use adequate protection). 119.8 g (782 mmol) racemic α-(acetyloxy)-α-methyl-cyclopropaneacetonitrile was emulsified in 7.0 L 0.1 M sodium chloride/3.8 mM sodium phosphate buffer pH 7.0 by stirring. The emulsion was cooled to 10° C. and the hydrolytic reaction started by adding 8.0 g of triacylglycerol lipase from wheat germ (Sigma L-3001) and the pH maintained at 7.0 by the controlled addition of 1.0 N sodium hydroxide solution under vigorous stirring at 10° C. After a consumption of 605.8 mL solution (corresponding to 78% conversion), after 118 h, the reaction was stopped by adding 6 L dichloromethane under vigorous stirring. The emulsion was allowed to stand overnight for phase separation. The organic phase was removed (the turbid part was filtered through silicon-treated Phase Separator (1PS; Whatman) and the filtrate stirred with ca. 1 L of Speedex filter aid). The aqueous phase was extracted again with 2×6 L dichloromethane. The combined organic phases were concentrated in vacuo down to a volume of ca. 40 mL and distilled (final temp. 68-69° C./4 mbar) to give 17.88 g (117 mmol; 15%) of (R)-α-(acetyloxy)-α-methyl-cyclopropaneacetonitrile as a colorless oil. Analysis: purity >99% GC; 98.0% ee (column: BGB-176; 30 m×0.25 mm; 100-140° C. with 2° C./min; $H_2$; 90 kPa; Inj. 200° C.; Det. 210° C.); $\alpha_D^{20}$: +32.92° (c=1.00; EtOH).

d) (R)-α-(aminomethyl)-α-methyl-cyclopropanemethanol

To a well stirred and ice-cooled suspension of lithium aluminiumhydride (10.1 g, 0.266 mol) in THF (250 mL) was added a solution of (R)-α-(acetyloxy)-α-methyl-cyclopropaneacetonitrile (13.6 g, 89 mmol) in THF (50 mL) so that the temperature of the cooled reaction mixture did not rise above 30° C. Once the addition was finished the mixture was refluxed for 2 h with stirring and over night at room temperature. The mixture was cooled and surplus lithium aluminiumhydride was destroyed by sequential addition of water (17 mL); sodium hydroxide solution (15%; 34 mL) and water (51 mL). The mixture was diluted with THF (150 mL), dried with Na2SO4, filtered and evaporated in vacuo. The residue was distilled to yield 4.4 g of the title compound as colorless oil, bp: 70-72° C./7 mbar, $\alpha_D^{20}$: +12.09° (MeOH).

e) 6-Chloro-5-(4-fluoro-phenyl)-nicotinic Acid Methyl Ester

The title compound was synthesized in analogy to Example 5a, using 5-bromo-6-chloro-3-pyridinecarboxylic acid methyl ester and 4-fluorophenylboronic acid as starting materials, MS (ISP) 266.1 $(M+H)^+$.

f) 6-Chloro-5-(4-fluoro-phenyl)-nicotinic Acid

The title compound was synthesized in analogy to Example 5b, using 6-chloro-5-(4-fluoro-phenyl)-nicotinic acid methyl ester as starting material, MS (EI) 251.1 $(M)^+$.

g) 5-(4-Fluoro-phenyl)-6-cyclopropylmethoxy-nicotinic Acid

The title compound was synthesized in analogy to Example 5c, using 6-chloro-5-(4-fluoro-phenyl)-nicotinic acid and (hydroxymethyl)cyclopropane as starting materials, MS (ISP) 286.0 (M–H).

h) N—((R)-2-Cyclopropyl-2-hydroxy-propyl)-6-cyclopropylmethoxy-5-(4-fluoro-phenyl)-nicotinamide The title compound was synthesized in analogy to Example 5d, using 5-(4-fluoro-phenyl)-6-cyclopropyl-methoxy-nicotinic acid and (R)-α-(aminomethyl)-α-methyl-cyclopropanemethanol as starting materials, MS (ISP) 385.2 $(M+H)^+$.

Example 8

Preparation of 5-(4-chloro-phenyl)-N-((1R,2R)-2-hydroxy-cyclohexyl)-6-(2,2,2-trifluoro-ethoxy)-nicotinamide a) 5-(4-Chloro-phenyl)-6-(2,2,2-trifluoro-ethoxy)-nicotinic Acid

The title compound was synthesized in analogy to Example 5c, using 6-chloro-5-(4-chloro-phenyl)-nicotinic acid and 2,2,2-trifluoro-ethanol as starting materials, MS (ISP) 330.3 (M–H).

b) N—((R)-2-Cyclopropyl-2-hydroxy-propyl)-6-cyclopropylmethoxy-5-(4-fluoro-phenyl)-nicotinamide The title compound was synthesized in analogy to Example 5d, using 5-(4-chloro-phenyl)-6-(2,2,2-trifluoro-ethoxy)-nicotinic acid and (1R,2R)-2-amino-cyclohexanol as starting materials, MS (ISP) 429.2 $(M+H)^+$.

Example 9

Preparation of 6-cyclopropylmethoxy-5-(4-fluoro-phenyl)-N-((1R,2R)-2-hydroxy-cyclohexyl)-nicotinamide The title compound was synthesized in analogy to Example 5d, using 5-(4-fluoro-phenyl)-6-cyclopropyl-methoxy-nicotinic acid and (1R,2R)-2-amino-cyclohexanol as starting materials, MS (ISP) 385.2 $(M+H)^+$.

Example 10

Preparation of 5-(2-Chloro-5-trifluoromethyl-phenyl)-6-cyclopentyloxy-N-((1R,2R)-2-hydroxy-cyclohexyl)-nicotinamide a) 5-Bromo-1,6-dihydro-6-oxo-3-pyridinecarboxylic Acid

To a suspension of 1,6-dihydro-6-oxo-pyridinecarboxylic acid (40 g, 288 mmol) in acetic acid (75 mL) bromine (69 g, 431 mmol) is added dropwise with stirring. The temperature increased to 45° C. and the mixture was stirred overnight at 50° C. The reaction mixture was concentrated in vacuo and the crude residue of 5-bromo-1,6-dihydro-6-oxo-3-pyridinecarboxylic acid was used in the next step without purification.

b) 5-Bromo-6-chloro-3-pyridinecarboxylic Acid Methyl Ester

To 63 g of the previous crude material was added with mechanical stirring phosphorus oxychloride (75 mL) and then phosphorus pentachloride (120 g) in portions so that the temperature did not rise above 30° C. The mixture was stirred overnight at 95° C. and concentrated in vacuo. The residue was dissolved in dichloromethane (150 mL) and methanol (150 mL) was added dropwise. The mixture was boiled for 2 h and the solvents were removed in vacuo. The residue was partitioned between diethyl ether and sodium bicarbonate solution. Organic phases were pooled, dried with $MgSO_4$ and the solvent was evaporated. The residue was purified by column chromatography on silica (n-heptane/ethyl acetate 6:1) to yield 4 g of the title compound as a colorless solid, mp 78-79° C.

c) 5-Bromo-6-cyclopentyloxy-3-pyridinecarboxylic Acid Methyl Ester

Cyclopentanol (1 mL, 11 mmol) was dissolved in DMF (25 mL) and a dispersion of sodium hydride in oil (55-65%, 480 mg) was added at room temperature. The mixture was stirred for 1 h at room temperature and 5-bromo-6-chloro-3-pyridinecarboxylic acid methyl ester (2.5 g, 10 mmol) was added. Stirring was continued for 1 h at room temperature and the mixture was afterwards partitioned between water and diethyl ether. Organic phases were pooled, dried with $MgSO_4$ and the solvent was evaporated. The residue was purified by column chromatography on silica (n-heptane/ethyl acetate 9:1) to yield 0.48 g of the title compound as a colorless oil, MS (EI) 299.0, 301.0 $(M)^+$.

d) 5-(2-Chloro-5-trifluoromethyl-phenyl)-6-cyclopentyloxy-3-pyridinecarboxylic Acid Methyl Ester 5-Bromo-6-cyclopentyloxy-3-pyridinecarboxylic acid methyl ester (0.33 g, 1.1 mmol) was dissolved in DMF (3.5 mL). To this solution was added [2-chloro-5-(trifluoromethyl)phenyl]-boronic acid (370 mg, 1.6 mmol), palladium (II)acetate (7 mg), triphenylphosphine (18 mg) and triethylamine (0.46 mL). The whole mixture was heated with stirring at 100° C. for 20 h, cooled to room temperature and partitioned between dichloromethane and a mixture of water and concentrated ammonium hydroxide solution (water/ammonia 4:1 v/v). Organic phases were pooled, dried with $MgSO_4$ and the solvent was evaporated. The residue was purified by column chromatography on silica (n-heptane/ethyl acetate 6:1) to yield 0.27 g of the title compound as a light yellow oil, MS (ISP) 400.4 $(M+H)^+$.

e) 5-(2-Chloro-5-trifluoromethyl-phenyl)-6-cyclopentyloxy-3-pyridinecarboxylic Acid 5-(2-Chloro-5-trifluoromethyl-phenyl)-6-cyclopentyloxy-3-pyridinecarboxylic acid methyl ester (0.27 g, 0.7 mmol) was dissolved in dioxane (6 mL). Water (6 mL) and sodium hydroxide solution (2 mL, 2N) was added and the mixture was boiled with stirring for 2.5 h, cooled to room temperature and partitioned between diethyl ether and hydrochloric acid (1N). Organic phases were pooled, dried with $Na_2SO_4$ and the solvent was evaporated. The residue, 0.27 g of the title compound as a orange-yellow solid was introduced into the next step without purification, MS (ISP) 386.5 $(M+H)^+$.

f) 5-(2-Chloro-5-trifluoromethyl-phenyl)-6-cyclopentyloxy-N-((1R,2R)-2-hydroxy-cyclohexyl)-nicotinamide 5-(2-Chloro-5-trifluoromethyl-phenyl)-6-cyclopentyloxy-3-pyridinecarboxylic acid (0.14 g, 0.3 mmol) was dissolved in DMF (5 mL). To the solution was added TBTU (0.12 g, 0.4 mmol), N,N-diisopropylethyl amine (0.3 mL, 1.7 mmol) and (1R,2R)-2-amino-cyclohexanol (58 mg, 0.4 mmol). The reaction mixture was stirred for 18 h at room temperature. The solvent was evaporated in vacuo and the residue was purified by column chromatography on silica (n-heptane/ethyl acetate gradient) to yield 0.11 g of the title compound as a colorless solid oil, MS (ISP) 483.4 $(M+H)^+$.

Example 11

Preparation of 6-Butoxy-5-(2-fluoro-5-trifluoromethyl-phenyl)-N-((1R,2R)-2-hydroxy-cyclohexyl)-nicotinamide a) 3-Bromo-5-methyl-2(1H)-pyridinone

5-Methyl-2(1H)-pyridinone (50 g, 0.46 mol) was suspended in dichloromethane (500 mL). N-bromosuccinimide (82 g, 0.46 mol) was added in portions with cooling. Addition was finished after 15 min; the mixture was stirred for 1 h at room temperature and afterwards partitioned between dichloromethane and water. Organic phases were pooled, dried with $Na_2SO_4$ and the solvent was evaporated. The residue was purified by crystallization from ethyl acetate to yield 55 g of the title compound as a light yellow solid, mp 156-161° C.

b) 3-Bromo-2-chloro-5-methyl-pyridine

A mixture of 3-bromo-5-methyl-2(1H)-pyridinone (25 g, 0.13 mol) and phosphorus oxychloride (500 mL) was boiled with stirring for 20 h. Phosphorus oxychloride was removed by distillation and the residue was poured onto ice/water (800 mL). The mixture was adjusted to pH 8.5 with 2 N sodium hydroxide solution and extracted with diethyl ether. Organic phases were pooled, dried with $Na_2SO_4$ and the solvent was evaporated. The residue, 23.4 g of the title compound as a greyish solid was introduced into the next step without purification, MS (EI) 204.9, 206.9 $(M)^+$.

c) 3-Bromo-2-butoxy-5-methyl-pyridine

Sodium hydride dispersion in oil (55-65%, 1.16 g) was added in portions to a well stirred solution of 1-butanol (2.4 mL, 27 mmol) in DMF (50 mL). After stirring the mixture for 1 h at room temperature 3-bromo-2-chloro-5-methyl-pyridine (5.0 g, 24 mmol) was added and stirring continued for 18 h at room temperature and for 4 h at 70° C. The cooled mixture was poured into saturated sodium bicarbonate solution and extracted with diethyl ether. Organic phases were pooled, dried with $Na_2SO_4$ and the solvent was evaporated. The residue was purified by column chromatography on silica (n-heptane/ethyl acetate 8:1) to yield 4.2 g of the title compound as a light red oil, MS (EI) 243.1, 245.1 $(M)^+$.

d) 2-Butoxy-3-(2-fluoro-5-trifluoromethyl-phenyl)-5-methyl-pyridine

3-Bromo-2-butoxy-5-methyl-pyridine (0.96 g, 3.9 mmol) was dissolved in toluene (6 mL). To this solution was added [2-fluoro-5-(trifluoromethyl)phenyl]-boronic acid (1.2 g, 5.9 mmol), [1,1'-bis(diphenylphosphino)ferrocene]dichloropalladium(II) dichloro-methane complex (161 mg), and 2 N sodium carbonate solution (5.9 mL). The whole mixture was heated with stirring at 90° C. for 18 h, cooled to room temperature and eluted with ethyl acetate over 10 g ChemElut (Varian). The solvent was evaporated and the residue was purified by column chromatography on silica (n-heptane/ethyl acetate gradient) to yield 0.99 g of the title compound as a yellow oil, MS (ISP) 328.3 (M+H)$^+$.

e) 6-Butoxy-5-(2-fluoro-5-trifluoromethyl-phenyl)-nicotinic Acid

N-Bromosuccinimide (1.2 g, 6.7 mmol) and 2,2'-azobis-(2-methyl-propionitrile) (5 mg) were added to a solution of 2-butoxy-3-(2-fluoro-5-trifluoromethyl-phenyl)-5-methyl-pyridine (0.96 g, 2.9 mmol) in carbon tetrachloride (30 mL). The mixture was irradiated and boiled with a halogen lamp for 2 h during which time 5 mg of 2,2'-azobis-(2-methyl-propionitrile) was added every 30 min. After cooling the mixture was poured onto sodium bisulfite solution (38-40%, 30 mL). This was extracted with dichloromethane. Organic phases were pooled, washed with water and dried $MgSO_4$. The solvent was evaporated and the residue (a mixture of 5-bromomethyl-2-butoxy-3-(2-fluoro-5-trifluoromethyl-phenyl)-pyridine and 2-butoxy-5-dibromomethyl-3-(2-fluoro-5-trifluoromethyl-phenyl)-pyridine) was dissolved in ethanol (19 mL). Ammonium hydroxide solution (conc. 5 mL) was added and the mixture was boiled for 1 h. After cooling the reaction mixture was poured onto hydrochloric acid (1 N, 100 mL) and partitioned into diethyl ether. The solvent was evaporated and the residue (a mixture of [6-butoxy-5-(2-fluoro-5-trifluoromethyl-phenyl)-pyridin-3-yl]-methanol and 6-butoxy-5-(2-fluoro-5-trifluoromethyl-phenyl)-pyridine-3-carbaldehyde) was dissolved in pyridine (28 mL). Tetrabutylammonium permanganate (3.1 g, 8.8 mmol) was added and the mixture was heated with stirring for 5 h. After cooling the reaction mixture was poured onto ice water (100 mL), sodium bisulfite solution (38-40%, 40 mL) was added, the mixture was adjusted to acidic pH with hydrochloric acid (250 mL, 2 N) and partitioned into diethyl ether. Organic phases were pooled, and dried with $MgSO_4$. The solvent was evaporated and the residue was purified by column chromatography on silica (n-heptane/ethyl acetate 3:1) to yield 0.51 g of the title compound as a yellow solid, MS (ISP) 356.1 (M−H)$^+$.

f) 6-Butoxy-5-(2-fluoro-5-trifluoromethyl-phenyl)-N-((1R,2R)-2-hydroxy-cyclohexyl)-nicotinamide 6-Butoxy-5-(2-fluoro-5-trifluoromethyl-phenyl)-nicotinic acid (0.10 g, 0.3 mmol) was dissolved in DMF (5 mL). To the solution was added TBTU (0.10 g, 0.3 mmol), N,N-diisopropylethyl amine (0.24 mL, 1.4 mmol) and (1R,2R)-2-amino-cyclohexanol (47 mg, 0.3 mmol). The reaction mixture was stirred for 18 h at room temperature. The solvent was evaporated in vacuo and the residue was purified by column chromatography on silica (n-heptane/ethyl acetate gradient) to yield 78 mg of the title compound as a light yellow solid, mp 172-178° C., MS (ISP) 455.3 (M+H)$^+$.

Example 12

Preparation of 6-Cyclohexyloxy-5-(2-fluoro-5-trifluoromethyl-phenyl)-N-((1R,2R)-2-hydroxy-cyclohexyl)-nicotinamide The title compound was synthesized in analogy to Example 11, using 3-bromo-2-chloro-5-methyl-pyridine, cyclohexanol, [2-fluoro-5-(trifluoromethyl)phenyl]-boronic acid and (1R,2R)-2-amino-cyclohexanol as starting materials, MS (ISP) 481.1 (M+H)$^+$.

Example 13

Preparation of 6-Butoxy-N-(2-cyclopropyl-2-hydroxy-propyl)-5-(2-fluoro-5-trifluoromethyl-phenyl)-nicotinamide The title compound was synthesized in analogy to Example 11, using 3-bromo-2-chloro-5-methyl-pyridine, n-butanol, [2-fluoro-5-(trifluoromethyl)phenyl]-boronic acid and rac-1-amino-2-cyclopropyl-propan-2-ol as starting materials, MS (ISP) 455.4 (M+H)$^+$.

Example 14

Preparation of 5-(4-Chloro-phenyl)-6-cyclohexyloxy-N-((1R,2R)-2-hydroxy-cyclohexyl)-nicotinamide The title compound was synthesized in analogy to Example 11, using 3-bromo-2-chloro-5-methyl-pyridine, cyclohexanol, [4-chloro-phenyl]-boronic acid and (1R,2R)-2-amino-cyclohexanol as starting materials, MS (ISP) 429.3 (M+H)$^+$.

Example 15

Preparation of 6-Butoxy-5-(4-chloro-phenyl)-N-((1R,2R)-2-hydroxy-cyclohexyl)-nicotinamide The title compound was synthesized in analogy to Example 11, using 3-bromo-2-chloro-5-methyl-pyridine, 1-butanol, [4-chloro-phenyl]-boronic acid and (1R,2R)-2-amino-cyclohexanol as starting materials, MS (ISP) 403.2 (M+H)$^+$.

Example 16

Preparation of 5-(4-Chloro-phenyl)-N-(2-cyclopropyl-2-hydroxy-propyl)-6-cyclopropylmethoxy-nicotinamide The title compound was synthesized in analogy to Example 11, using 3-bromo-2-chloro-5-methyl-pyridine, cyclopropanemethanol, [4-chloro-phenyl]-boronic acid and rac-1-amino-2-cyclopropyl-propan-2-ol as starting materials, MS (ISP) 401.2 (M+H)$^+$.

Example 17

Preparation of 6-Cyclopentyloxy-5-(2-fluoro-5-trifluoromethyl-phenyl)-N-((1R,2R)-2-hydroxy-cyclohexyl)-nicotinamide The title compound was synthesized in analogy to Example 11, using 3-bromo-2-chloro-5-methyl-pyridine, cyclopentanol, [2-fluoro-5-(trifluoromethyl)phenyl]-boronic acid and (1R,2R)-2-amino-cyclohexanol as starting materials, MS (ISP) 467.3 (M+H)$^+$.

Example 18

Preparation of 6-Cyclopentyloxy-N-(2-cyclopropyl-2-hydroxy-propyl)-5-(2-fluoro-5-trifluoromethyl-phenyl)-nicotinamide The title compound was synthesized in analogy to Example 11, using 3-bromo-2-chloro-5-methyl-pyridine, cyclopentanol, [2-fluoro-5-(trifluoromethyl)phenyl]-boronic acid and rac-1-amino-2-cyclopropyl-propan-2-ol as starting materials, MS (ISP) 467.3 (M+H)$^+$.

Example 19

Preparation of 6-(2-Chloro-phenyl)-5-pyrrolidin-1-yl-pyrazine-2-carboxylic Acid ((1R,2R)-2-hydroxy-cyclohexyl)-amide a) 5-Bromo-3-(2-chloro-phenyl)-pyrazin-2-ylamine Tetrakis(triphenylphosphine)palladium (0.24 g) is added at room temperature to a solution of 2-amino-3,5-dibromopyrazine (0.51 g) in dimethoxyethane (12 mL). The mixture is stirred for 30 min and sodium carbonate (0.53 g), water (6 mL) and 2-chlorophenylboronic acid (0.32 g) are added and the mixture is stirred for 18 h at 100° C. The mixture is cooled, citric acid (10%, 20 mL) is added and the mixture is extracted with ethyl acetate (3×50 mL). Organic phases were pooled, washed with sodium bicarbonate and brine, dried with Na$_2$SO$_4$ and the solvent was evaporated. The residue was purified by chromatography on silica gel with dichloromethane to yield 0.31 g of the title compound as a white solid, mp 138.5-139.5° C.

b) 5-Bromo-3-(2-chloro-phenyl)-2-pyrrolidin-1-yl-pyrazine

Sodium hydride (0.55 g) is added at room temperature to a solution of 5-bromo-3-(2-chloro-phenyl)-pyrazin-2-ylamine (0.23 g) in DMF (10 mL). Subsequently 1-bromo-4-chlorobutane (0.21 g) is added and the mixture is stirred for 3 h. Citric acid (10%, 20 mL) is added and the mixture is extracted with ethyl acetate (3×50 mL). Organic phases were pooled, washed with sodium bicarbonate and brine, dried with Na$_2$SO$_4$ and the solvent was evaporated. The residue was purified by chromatography on silica gel with heptane/ethyl acetate 2:1 to yield 0.27 g of the title compound as a yellow oil, MS (ISP) 338.1, 340.0 (M+H)$^+$.

c) 6-(2-Chloro-phenyl)-5-pyrrolidin-1-yl-pyrazine-2-carboxylic Acid Methyl Ester To a solution of 5-bromo-3-(2-chloro-phenyl)-2-pyrrolidin-1-yl-pyrazine (0.25 g) in 7 ml methanol was added 2 ml ethyl acetate, 0.035 g [1,1'-bis(diphenylphosphino)-ferrocen] palladium(II)chloride 1:1 complex with dichloromethane and 0.25 ml triethylamine and the mixture was stirred at 110° C. under 70 bar carbon monoxide for 18 h. The reaction mixture was evaporated and the residue was purified by chromatography on silica gel with heptane:ethyl acetate=2:1 to yield 0.15 g of the title compound as off-white foam, MS (ISP) 318.1 (M+H)$^+$.

d) 6-(2-Chloro-phenyl)-5-pyrrolidin-1-yl-pyrazine-2-carboxylic Acid

To a solution of 6-(2-chloro-phenyl)-5-pyrrolidin-1-yl-pyrazine-2-carboxylic acid methyl ester (0.15 g) in tetrahydrofuran (2 mL), water (0.5 mL) and methanol (0.5 mL) was added at room temperature 1 ml of a 1M solution of lithium hydroxide in water and the mixture was stirred for 2 h. The resulting solution was partitioned between 10% aqueous citric acid and ethyl acetate. The phases were separated and the organic layer was washed with water and brine. The organic phase was dried over magnesium sulfate and evaporated to yield 0.14 g of the title compound as white solid, MS (ISP) 304.1 (M+H)$^+$.

e) 6-(2-Chloro-phenyl)-5-pyrrolidin-1-yl-pyrazine-2-carboxylic Acid ((1R,2R)-2-hydroxy-cyclohexyl)-amide To a solution of 0.10 g 6-(2-chloro-phenyl)-5-pyrrolidin-1-yl-pyrazine-2-carboxylic acid in 3.0 ml of DMF is added at room temperature 0.082 g 1,1'-carbonyl-diimidazole, 0.22 ml N-ethyldiisopropylamine and 0.057 g (1R,2R)-2-amino-cyclohexanol hydrochloride and stirred for 72 hours. To the mixture is added citric acid 10% solution and ethyl acetate. The organic layer is washed with sodium bicarbonate 10% solution and sodium chloride saturated solution. The organic layer is separated and dried over sodium sulfate and evaporated at the rotary evaporator. The residue is purified by chromatography on silica gel with heptane/ethyl acetate 40/60 to yield 0.055 g of the title compound as white solid, MS (ISP) 401.3 (M+H)$^+$.

Example 20

Preparation of 6-(2-Chloro-phenyl)-5-cyclopentylamino-pyrazine-2-carboxylic Acid ((1R,2R)-2-hydroxy-cyclohexyl)-amide The title compound was synthesized in analogy to Example 19, using 5-bromo-3-(2-chloro-phenyl)-pyrazin-2-ylamine and bromocyclopentane in step b, carbonylation as in step c, saponification as in step d and amide coupling with (1R,2R)-2-amino-cyclohexanol hydrochloride as in step e to give the title compound as a white solid, MS (ISP) 415.3 (M+H)$^+$.

Example 21

Preparation of 5-(4-Chloro-phenyl)-6-cyclopentyloxy-N-((1R,2R)-2-hydroxy-cyclohexyl)-nicotinamide The title compound was synthesized in analogy to Example 11, using 3-bromo-2-chloro-5-methyl-pyridine, cyclopentanol, 4-chlorophenyl-boronic acid and (1R,2R)-2-amino-cyclohexanol as starting materials, MS (ISP) 415.2 (M+H)$^+$.

Example 22

Preparation of 5-(2-Chloro-5-trifluoromethyl-phenyl)-N-(2-cyclopropyl-2-hydroxy-propyl)-6-cyclopropylmethoxy-nicotinamide The title compound was synthesized in analogy to Example 11, using 3-bromo-2-chloro-5-methyl-pyridine, (hydroxymethyl)cyclopropane, [2-chloro-5-(trifluoromethyl)phenyl]-boronic acid and rac-1-amino-2-cyclopropyl-propan-2-ol as starting materials, MS (ISP) 469.1, 471.0 $(M+H)^+$.

Example 23

Preparation of 5-(4-Chloro-phenyl)-N-((1R,2R)-2-hydroxy-cyclohexyl)-6-phenoxy-nicotinamide a) 3-Bromo-5-methyl-2-phenoxy-pyridine

Sodium hydride dispersion in oil (~70%, 0.68 g) was added in portions to a well stirred solution of phenol (1.33 g, 14 mmol) in DMA (100 mL). After stirring the mixture for 1 h at 50° C. 3-bromo-2-chloro-5-methyl-pyridine (2.68 g, 13 mmol) was added and stirring continued for 28 h at 100° C. The cooled mixture was poured into water and extracted with diethyl ether. Organic phases were pooled, dried with $Na_2SO_4$ and the solvent was evaporated. The residue was purified by column chromatography on silica (n-heptane/ethyl acetate 8:1) to yield 1.4 g of the title compound as a colorless oil, $^1$H NMR $(CDCl_3)$: δ=2.27 (s, 3H), 7.12 (d, 2H), 7.19 (t, 1H), 7.39 (t, 2H), 7.76 (s, 1H), 7.88 (s, 1H).

b) 3-(4-Chloro-phenyl)-5-methyl-2-phenoxy-pyridine

3-Bromo-5-methyl-2-phenoxy-pyridine (0.79 g, 3.0 mmol) was dissolved in toluene (5 mL). To this solution was added [1,1'-bis(diphenylphosphino)-ferrocene]dichloropalladium(II) dichloro-methane complex (120 mg), 4-chlorophenyl-boronic acid (0.7 g, 4.5 mmol), and 2 N sodium carbonate solution (4.7 mL). The whole mixture was heated with stirring at 90° C. for 18 h, cooled to room temperature and eluted with ethyl acetate over 10 g ChemElut (Varian). The solvent was evaporated and the residue was purified by column chromatography on silica (n-heptane/ethyl acetate gradient) to yield 0.61 g of the title compound as a yellowish oil, MS (ISP) 296.4 $(M+H)^+$.

c) 5-(4-Chloro-phenyl)-N-((1R,2R)-2-hydroxy-cyclohexyl)-6-phenoxy-nicotinamide The title compound was synthesized in analogy to Example 11, step e and f using 3-(4-Chloro-phenyl)-5-methyl-2-phenoxy-pyridine and (1R,2R)-2-amino-cyclohexanol as starting materials, MS (ISP) 422.9 $(M+H)^+$.

Example 24

Preparation of 6-(4-Chloro-phenyl)-5-piperidin-1-yl-pyrazine-2-carboxylic Acid (1-hydroxy-indan-2-yl)-amide The title compound was synthesized in analogy to Example 19, using 2-amino-3,5-dibromopyrazine and 4-chlorophenylboronic acid in step a, 1-bromo-5-chloropentane in step b, carbonylation as in step c, saponification as in step d and amide coupling with 2-amino-1-indanol as in step e to give the title compound as a light yellow foam, MS (ISP) 449.3 $(M+H)^+$.

Example 25

Preparation of 6-(3,4-Dichloro-phenyl)-5-pyrrolidin-1-yl-pyrazine-2-carboxylic Acid (2-cyclopropyl-2-hydroxy-propyl)-amide The title compound was synthesized in analogy to Example 19, using 2-amino-3,5-dibromopyrazine and 3,4-dichlorophenylboronic acid in step a, 1-bromo-4-chlorobutane in step b, carbonylation as in step c, saponification as in step d and amide coupling with rac-1-amino-2-cyclopropyl-propan-2-ol as in step e to give the title compound as a light yellow solid, MS (ISP) 435.3, 437.2 $(M+H)^+$.

Example 26

Preparation of 5-(4-Chloro-phenyl)-N-(2-cyclopropyl-2-hydroxy-propyl)-6-(2-methoxy-ethoxy)-nicotinamide The title compound was synthesized in analogy to the procedure described for the preparation of Example 6, using 5-bromo-1,6-dihydro-6-oxo-3-pyridinecarboxylic acid methyl ester, 2-methoxy-ethanol (commercially available), 4-chlorophenyl-boronic acid (commercially available) and rac-1-amino-2-cyclopropyl-propan-2-ol (commercially available) as starting materials. MS (ISP): 405.4 $(MH^+)$.

Example 27

Preparation of 5-(4-Chloro-phenyl)-N-(2-cyclopropyl-2-hydroxy-propyl)-6-(2-methoxy-ethoxy)-nicotinamide The title compound was synthesized in analogy to the procedure described for the preparation of Example 6, using 5-bromo-1,6-dihydro-6-oxo-3-pyridinecarboxylic acid methyl ester, 2-methoxy-ethanol (commercially available), 4-chlorophenyl-boronic acid (commercially available) and morpholine (commercially available) as starting materials. MS (ISP): 377.1 $(MH^+)$.

Example 28

Preparation of 5-(4-Chloro-phenyl)-N—((R)-1-hydroxymethyl-3-methyl-butyl)-6-(2-propionylamino-ethoxy)-nicotinamide a) 5-Bromo-6-chloro-N—((R)-1-hydroxymethyl-3-methyl-butyl)-nicotinamide

5-Bromo-6-chloro-nicotinic acid (2.0 g, 8.46 mmol) was dissolved in DMA (20 mL). To the solution was added TBTU (3.1 g, 9.3 mmol), N,N-diisopropylethyl amine (7.4 mL, 42 mmol) and (D)-leucinol (1.1 g, 9.3 mmol). The reaction mixture was stirred for 16 h at room temperature. The solvent was evaporated in vacuo and the residue was purified by column chromatography on silica (cyclohexane/ethyl acetate gradient) to yield 2.6 g of the title compound as a yellow oil, MS (ISP) 337.1 $(M+H)^+$.

b) (5-Bromo-6-chloro-pyridin-3-yl)-((R)-4-isobutyl-2,2-dimethyl-oxazolidin-3-yl)-methanone 5-Bromo-6-chloro-N—((R)-1-hydroxymethyl-3-methyl-butyl)-nicotinamide (2.6 g, 8.0 mmol) was dissolved in 2,2-dimethoxypropane (25 mL, 200 mmol). To the solution was added camphorsulfonic acid (19 mg, 0.08 mmol) and the reaction mixture was stirred for 24 h at 60° C. After cooling drops of triethylamine were added and the solvent was evaporated in vacuo. The residue was purified by column chromatography on silica (cyclohexane/ethyl acetate gradient) to yield 2.0 g of the title compound as light yellow oil.

c) [6-Chloro-5-(4-chloro-phenyl)-pyridin-3-yl]-((R)-4-isobutyl-2,2-dimethyl-oxazolidin-3-yl)-methanone (5-Bromo-6-chloro-pyridin-3-yl)-((R)-4-isobutyl-2,2-dimethyl-oxazolidin-3-yl)-methanone (2.0 g, 5.5 mmol) was dissolved in toluene (10 mL). To this solution was added [1,1'-bis(diphenylphosphino)ferrocene]dichloropalladium (II) dichloro-methane complex (226 mg), 4-chlorophenyl-boronic acid (1.34 g, 8.3 mmol), and 2 N sodium carbonate solution (8.3 mL). The whole mixture was heated with stirring at 90° C. for 18 h, cooled to room temperature (RT) and eluted with ethyl acetate over 10 g ChemElut (Varian). The solvent was evaporated and the residue was purified by column chromatography on silica (cyclohexane/ethyl acetate gradient) to yield 0.81 g of the title compound as off-white solid.

d) N-{2-[3-(4-Chloro-phenyl)-5-((R)-4-isobutyl-2,2-dimethyl-oxazolidine-3-carbonyl)-pyridin-2-yloxy]-ethyl}-propionamide Sodium hydride dispersion in oil (~55%, 72 mg) was added in portions to a well stirred solution of N-(2-hydroxyethyl) propionamide (71 mg, 0.6 mmol) in THF (13 mL). After stirring the mixture for 15 min at RT [6-Chloro-5-(4-chloro-phenyl)-pyridin-3-yl]-((R)-4-isobutyl-2,2-dimethyl-oxazolidin-3-yl)-methanone (225 mg, 0.55 mmol) was added and stirring continued for 6 h at RT. The mixture was poured into water and extracted with diethyl ether. Organic phases were pooled, dried with $Na_2SO_4$ and the solvent was evaporated. The residue was purified by column chromatography on silica (cyclohexane/ethyl acetate 8:1) to yield 89 mg of the title compound as a white solid, MS (ISP) 488.2 $(M+H)^+$.

e) 5-(4-Chloro-phenyl)-N—((R)-1-hydroxymethyl-3-methyl-butyl)-6-(2-propionylamino-ethoxy)-nicotinamide N-{2-[3-(4-Chloro-phenyl)-5-((R)-4-isobutyl-2,2-dimethyl-oxazolidine-3-carbonyl)-pyridin-2-yloxy]-ethyl}-propionamide (82 mg, 0.16 mmol) was dissolved in methanol (0.35 mL). To the solution was added camphorsulfonic acid (1.6 mg, 0.007 mmol) and the reaction mixture was stirred for 1 h at RT. The mixture was poured into water, sodiumbicarbonate was added and the mixture extracted with ethyl acetate. Organic phases were pooled, the solvent was evaporated in vacuo and the residue was purified by column chromatography on silica (dichloromethane/methanol gradient) to yield 55 mg of the title compound as a white solid, MS (ISP) 448.3 $(M+H)^+$.

Example 29

Preparation of 5-(4-Chloro-phenyl)-N—((R)-1-hydroxymethyl-pentyl)-6-(2-methoxy-ethoxy)-nicotinamide The title compound was synthesized in analogy to the procedure described for the preparation of Example 6, using 5-bromo-1,6-dihydro-6-oxo-3-pyridinecarboxylic acid methyl ester, 2-methoxy-ethanol (commercially available), 4-chlorophenyl-boronic acid (commercially available) and (R)-(−)-2-amino-1-hexanol (commercially available) as starting materials. MS (ISP): 407.4 $(M+H^+)$.

Example 30

Preparation of 5-(4-Chloro-phenyl)-N—((S)-1-hydroxymethyl-2,2-dimethyl-propyl)-6-(2-methoxy-ethoxy)-nicotinamide The title compound was synthesized in analogy to the procedure described for the preparation of Example 6, using 5-bromo-1,6-dihydro-6-oxo-3-pyridinecarboxylic acid methyl ester, 2-methoxy-ethanol (commercially available), 4-chlorophenyl-boronic acid (commercially available) and L-tert-leucinol (commercially available) as starting materials. MS (ISP): 407.4 $(MH^+)$.

Example 31

Preparation of 6-Cyclopropylmethoxy-5-(3,4-difluoro-phenyl)-N-((trans)-2-hydroxy-cyclohexyl)-nicotinamide a) 5-Bromo-6-cyclopropylmethoxy-nicotinic Acid

A mixture of 3.0 g (13 mmol) 5-Bromo-6-chloro-nicotinic acid, 1.4 g (19 mmol) (hydroxymethyl)cyclopropane and 2.85 g (51 mmol) potassium hydroxide in DMSO (12 mL) was heated under microwave radiation for 6 min to 100° C. 50 mL water and 150 mL citric acid (10%) was added. A solid precipitated, was filtered off, re-dissolved in ethyl acetate and dried with $Na_2SO_4$. The product crystallized upon evaporation of the solvent from ethyl acetate/heptane 1:1 to yield 2.1 g (71%) of the title compound as white solid, MS (ISP): 270.3 (M−H).

b) 5-Bromo-6-cyclopropylmethoxy-N-((trans)-2-hydroxy-cyclohexyl)-nicotinamide 5-Bromo-6-cyclopropylmethoxy-nicotinic acid (2.3 g, 8.5 mmol) was dissolved in DMF (75 mL). To the solution was added TBTU (2.99 g, 9.3 mmol), N,N-diisopropylethyl amine (7.2 mL, 42 mmol) and (trans)-2-amino-cyclohexanol (1.4 g, 9.3 mmol). The reaction mixture was stirred for 16 h at room temperature. The solvent was evaporated in vacuo and the residue was purified by column chromatography on silica (n-heptane/ethyl acetate gradient) to yield 2.5 g of the title compound as a white solid, MS (ISP) 368.9, 371.0 $(M+H)^+$.

c) 6-Cyclopropylmethoxy-5-(3,4-difluoro-phenyl)-N-((trans)-2-hydroxy-cyclohexyl)-nicotinamide The title compound was synthesized in analogy to the Suzuki reaction procedure described for the preparation of Example 5a, from 5-Bromo-6-cyclopropylmethoxy-N-

(trans-2-hydroxy-cyclohexyl)-nicotinamide and 3,4-difluorophenylboronic acid (commercially available). MS (ISP): 403.4 (M+H)$^+$.

Example 32

Preparation of 6-Cyclopropylmethoxy-5-(4-fluorophenyl)-N-((trans)-2-hydroxy-cyclohexyl)-nicotinamide The title compound was synthesized in analogy to the procedure described for the preparation of Example 31, using 5-bromo-N-(trans-2-hydroxy-cyclohexyl)-6-(2-methoxyethoxy)-nicotinamide and 4-fluorophenylboronic acid (commercially available) as starting materials. MS (ISP): 385.4 (M+H)$^+$.

Example 33

Preparation of 6-Cyclopropylmethoxy-N-((trans)-2-hydroxy-cyclohexyl)-5-(4-trifluoromethyl-phenyl)-nicotinamide The title compound was synthesized in analogy to the procedure described for the preparation of Example 31, using 5-bromo-6-cyclopropylmethoxy-N-(trans-2-hydroxy-cyclohexyl)-nicotinamide and 4-trifluoromethylphenylboronic acid (commercially available) as starting materials. MS (ISP): 435.4 (M+H)$^+$.

Example 34

Preparation of 6-Cyclopropylmethoxy-5-(3,4-dichloro-phenyl)-N-((trans)-2-hydroxy-cyclohexyl)-nicotinamide The title compound was synthesized in analogy to the procedure described for the preparation of Example 31, using 5-bromo-6-cyclopropylmethoxy-N-(trans-2-hydroxy-cyclohexyl)-nicotinamide and 3,4-difluorophenylboronic acid (commercially available) as starting materials. MS (ISP): 437.3 (M+H)$^+$.

Example 35

Preparation of 5-(4-Cyano-phenyl)-6-cyclopropylmethoxy-N-((trans)-2-hydroxy-cyclohexyl)-nicotinamide The title compound was synthesized in analogy to the procedure described for the preparation of Example 31, using 5-bromo-6-cyclopropylmethoxy-N-(trans-2-hydroxy-cyclohexyl)-nicotinamide and 4-cyanophenylboronic acid (commercially available) as starting materials. MS (ISP): 392.2 (M+H)$^+$.

Example 36

Preparation of 6-(4-Chloro-phenyl)-5-cyclopropylmethoxy-pyrazine-2-carboxylic Acid ((R)-1-hydroxymethyl-3-methyl-butyl)-amide a) 5-Bromo-3-(4-chloro-phenyl)-pyrazin-2-ylamine To a solution of 2.5 g of 3,5-dibromo-pyrazin-2-ylamine in 60 ml 1,2-dimethoxy-ethane is added 1.19 g tetrakis(triphenylphosphine) palladium at room temperature and stirred for ½ hour. To the resulting orange solution is added a solution of 2.65 g sodium carbonate in 30.0 mL water and 1.56 g of p-chlorophenylboronic acid and the mixture is stirred for 18 hours at 100° C. The starting material is completely consumed as evidenced by tlc. The reaction mixture was partitioned between water and ethyl acetate; the phases are separated and the organic phase is dried over sodium sulfate evaporated and purified by chromatography on silica gel with heptane:ethyl acetate=1:1. to yield 2.37 g of the title compound as light yellow crystals, MS (ISP) 284.0, 286.0 (M+H)$^+$.

b) 2,5-Dibromo-3-(4-chloro-phenyl)-pyrazine

To a solution of 2.36 g 2,5-dibromo-3-(4-chloro-phenyl)-pyrazine in 15 ml dibromomethane was added 1.3 ml isoamylnitrite. To the resulting solution was added dropwise during ca 30 min. a solution of 1.50 g trimethylbromosilane in 5 ml dribromomethane at ambient temperature. The mixture was stirred for 1 h. To the resulting dark solution was added 30 ml of a 10% aqueous sodium bicarbonate solution. The phases were separated and the organic phase was purified by chromatography on silica gel with heptan:ethyl acetate=9:1. The product fractions were collected and concentrated upon which crystallization occurred. The solid was collected by filtration to yield 2.13 g of the title compound as slightly yellow crystals, MS (ISP) 350.0 (M+H)$^+$.

c) 5-Bromo-3-(4-chloro-phenyl)-2-cyclopropyl-methoxy-pyrazine

To a solution of 0.079 g cyclopropanol in 2 ml dimethylsulfoxide was added 0.096 g sodium hydride 55% in oil and the mixture was stirred at room temperature for 45 min. To the resulting mixture was added 0.348 g 2,5-dibromo-3-(4-chloro-phenyl)-pyrazine and the mixture was stirred at room temperature for 3 h. The reaction mixture was partitioned between water and ethyl acetate. The phases were separated and the organic phase was purified by chromatography on silica gel with heptane:dichloromethane=1:1 to yield 0.199 g of the title compound as white crystals melting at 86-87° C.

d) 6-(4-Chloro-phenyl)-5-cyclopropylmethoxy-pyrazine-2-carboxylic Acid ((R)-1-hydroxymethyl-3-methyl-butyl)-amide The title compound was synthesized in analogy to Example 19, carbonylating 5-bromo-3-(4-chloro-phenyl)-2-cyclopropylmethoxy-pyrazine as in step c, saponification as in step d and amide coupling with (R)-leucinol as in step e to give the title compound as a light yellow solid, MS (ISP) 404.5 (M+H)$^+$.

Example 37

Preparation of (RS)-5-(4-Chloro-phenyl)-N-(2-hydroxy-3-methoxy-propyl)-6-(2-methoxy-ethoxy)-nicotinamide The title compound was synthesized in analogy to the procedure described for the preparation of Example 6, using 2,5-dibromo-3-(4-chloro-phenyl)-pyrazine, 2-methoxyethanol (commercially available), and rac-1-amino-3-methoxy-2-propanol (commercially available) as starting materials to give the title compound as a yellow oil. MS (ISP): 395.1 (M+H)$^+$.

Example 38

Preparation of 6-(4-Chloro-phenyl)-5-(3-methyl-butoxy)-pyrazine-2-carboxylic Acid ((1R,2R)-2-hydroxy-cyclohexyl)-amide The title compound was synthesized in analogy to the procedure described for the preparation of Example 36, using 2,5-dibromo-3-(4-chloro-phenyl)-pyrazine, 3-methyl-1-butanol (commercially available), and (1R,2R)-2-amino-cyclohexanol (commercially available) as starting materials to give the title compound as a yellow oil, MS (ISP): 418.2 (M+H)$^+$.

Example 39

Preparation of 5-(2-Chloro-phenoxy)-6-(4-chloro-phenyl)-pyrazine-2-carboxylic Acid ((1R,2R)-2-hydroxy-cyclohexyl)-amide a) 5-Amino-6-(4-chloro-phenyl)-pyrazine-2-carboxylic Acid Methyl Ester The title compound was synthesized in analogy to the procedure described for the preparation of Example 19c, by carbonylation of 5-bromo-3-(4-chloro-phenyl)-pyrazin-2-ylamine to give the title compound as an off white solid, mp.: 186-188° C.

b) 5-Bromo-6-(4-chloro-phenyl)-pyrazine-2-carboxylic Acid Methylester

The title compound was synthesized in analogy to the procedure described for the preparation of Example 36b, using 5-amino-6-(4-chloro-phenyl)-pyrazine-2-carboxylic acid methyl ester as starting material and isoamylnitrite, dibromomethane and trimethylbromosilane as reagents to give the title compound which was used in the next step without further purification.

c) 5-Bromo-6-(4-chloro-phenyl)-pyrazine-2-carboxylic Acid Methylester

The title compound was synthesized in analogy to the procedure described for the preparation of Example 19d, by saponification of 5-bromo-6-(4-chloro-phenyl)-pyrazine-2-carboxylic acid methyl ester to give the title compound as white solid, MS (ISP): 312.9 (M−H)$^+$.

d) 5-Bromo-6-(4-chloro-phenyl)-pyrazine-2-carboxylic Acid ((1R,2R)-2-hydroxy-cyclohexyl)-amide The title compound was synthesized in analogy to the procedure described for the preparation of Example 19e, using 5-bromo-6-(4-chloro-phenyl)-pyrazine-2-carboxylic acid, and (1R,2R)-2-amino-cyclohexanol (commercially available) as starting materials to give the title compound as a light yellow solid, MS (ISP): 410.0, 412.0 (M+H)$^+$.

e) 5-(2-Chloro-phenoxy)-6-(4-chloro-phenyl)-pyrazine-2-carboxylic Acid ((1R,2R)-2-hydroxy-cyclohexyl)-amide The title compound was synthesized in analogy to the procedure described for the preparation of Example 36c, using 5-bromo-6-(4-chloro-phenyl)-pyrazine-2-carboxylic acid ((1R,2R)-2-hydroxy-cyclohexyl)-amide, and chlorophenol (commercially available) as starting materials to give the title compound as a white solid. mp.: 154-155° C., MS (ISP): 458.3, 460.3 (M+H)$^+$.

Example 40

Preparation of 6-(4-Fluoro-phenyl)-5-(3-methoxy-propoxy)-pyrazine-2-carboxylic Acid (2-cyclopropyl-2-hydroxy-propyl)-amide a) 5-Bromo-3-(4-fluoro-phenyl)-pyrazin-2-ylamine The title compound was synthesized in analogy to the procedure described for the preparation of Example 19a using 2-amino-3,5-dibromopyrazine, and 4-fluorophenylboronic acid (commercially available) as starting materials to give the title compound as a white solid, MS (ISP) 268.1, 270.2 (M+H)$^+$.

b) 6-(4-Fluoro-phenyl)-5-(3-methoxy-propoxy)-pyrazine-2-carboxylic Acid (2-cyclopropyl-2-hydroxy-propyl)-amide The title compound was synthesized in analogy to the procedure described for the preparation of Example 39 using 5-Bromo-3-(4-fluoro-phenyl)-pyrazin-2-ylamine, 3-methoxy-1-propanol (commercially available), and rac-1-amino-2-cyclopropyl-propan-2-ol (commercially available) as starting materials to give the title compound as a colorless oil. MS (ISP): 404.4 (M+H)$^+$.

Example 41

Preparation of 5-Cyclopropylmethoxy-6-(4-fluoro-phenyl)-pyrazine-2-carboxylic Acid (2-cyclopropyl-2-hydroxy-propyl)-amide The title compound was synthesized in analogy to the procedure described for the preparation of Example 40 using 5-bromo-3-(4-fluoro-phenyl)-pyrazin-2-ylamine, hydroxymethylcyclopropane (commercially available), and rac-1-amino-2-cyclopropyl-propan-2-ol (commercially available) as starting materials to give the title compound as a white foam. MS (ISP): 386.4 (M+H)$^+$.

Example 42

Preparation of 6-((R)-sec-Butoxy)-5-(4-chloro-phenyl)-N-((1R,2R)-2-hydroxy-cyclohexyl)-nicotinamide The title compound was synthesized in analogy to the procedure described for the preparation of Example 5, using 5-bromo-6-chloro-3-pyridinecarboxylic acid methyl ester, 4-chlorophenyl-boronic acid (commercially available), (R)-(−)-2-butanol (commercially available), and (1R,2R)-2-amino-cyclohexanol (commercially available) as starting materials. MS (ISP): 403.5 (MH$^+$).

Example 43

Preparation of N-((1R,2R)-2-Hydroxy-cyclohexyl)-6-(2-methoxy-ethoxy)-5-(4-trifluoromethyl-phenyl)-nicotinamide a) 5-Bromo-6-(2-methoxy-ethoxy)-nicotinic Acid A mixture of 325 mg (1.3 mmol) 5-bromo-6-chloro-nicotinic acid methyl ester, 233 mg (3.24 mmol) 2-methoxyethanol and 493 mg (3.24 mmol) DBU was heated under microwave radiation for 2 min to 180° C. 0.65 mL water and 0.49 mL 5N KOH aq. was added and the mixture was heated under microwave radiation for 2 min to 160° C. The mixture was acidified with 1N HCl aq. and extracted with ethyl acetate. After evaporation the residue was purified by preparative HPLC on reversed phase eluting with a gradient formed from acetonitrile/water/HCOOH. The combined product fractions were evaporated to yield 237 mg (66%) of the title compound as white solid. MS (ISP): 274 (M−H).

b) N-((1R,2R)-2-Hydroxy-cyclohexyl)-6-(2-methoxy-ethoxy)-5-(4-trifluoromethyl-phenyl)-nicotinamide The title compound was synthesized in analogy to the procedure described for the preparation of Example 31b to c, using 5-bromo-6-(2-methoxy-ethoxy)-nicotinic acid, 4-trifluoromethylphenyl-boronic acid (commercially available) and (1R,2R)-2-amino-cyclohexanol (commercially available) as starting materials. MS (ISP): 439.0 (M+H$^+$).

Example 44

Preparation of N-((1R,2R)-2-Hydroxy-cyclohexyl)-6-(2-methoxy-ethoxy)-5-(4-trifluoromethoxy-phenyl)-nicotinamide The title compound was synthesized in analogy to the procedure described for the preparation of Example 43, using 5-bromo-6-chloro-nicotinic acid methyl ester, 2-methoxyethanol (commercially available), 4-trifluoromethoxyphenyl-boronic acid (commercially available) and (1R,2R)-2-amino-cyclohexanol (commercially available) as starting materials. MS (ISP): 455.1 (M+H$^+$).

Example 45

Preparation of 5-(4-Chloro-phenyl)-N-((1R,2R)-2-hydroxy-cyclohexyl)-6-(2-isopropoxy-ethoxy)-nicotinamide The title compound was synthesized in analogy to the procedure described for the preparation of Example 43, using 5-bromo-6-chloro-nicotinic acid methyl ester, 2-isopropoxyethanol (commercially available), 4-chlorophenyl-boronic acid (commercially available) and (1R,2R)-2-amino-cyclohexanol (commercially available) as starting materials. MS (ISP): 433.2 (M+H$^+$).

Example 46

Preparation of 5-(4-Chloro-phenyl)-N-((1R,2R)-2-hydroxy-cyclohexyl)-6-isopropoxy-nicotinamide The title compound was synthesized in analogy to the procedure described for the preparation of Example 43, using 5-bromo-6-chloro-nicotinic acid methyl ester, 4-chlorophenyl-boronic acid (commercially available), isopropanol (commercially available), and (1R,2R)-2-amino-cyclohexanol (commercially available) as starting materials. MS (ISP): 389.3, 391.4 (M+H$^+$).

Example 47

Preparation of 5-(4-Chloro-phenyl)-N-((1R,2R)-2-hydroxy-cyclohexyl)-6-[(2-methoxy-ethyl)-methyl-amino]-nicotinamide The title compound was synthesized in analogy to the procedure described for the preparation of Example 43, using 5-bromo-6-chloro-nicotinic acid methyl ester, 4-chlorophenyl-boronic acid (commercially available), (2-methoxy-ethyl)-methyl-amine (commercially available), and (1R,2R)-2-amino-cyclohexanol (commercially available) as starting materials. MS (ISP): 452.0 (M+H$^+$).

Example 48

Preparation of 5-(4-Chloro-phenyl)-N-((1R,2R)-2-hydroxy-cyclohexyl)-6-(2-methoxy-1-methyl-ethoxy)-nicotinamide The title compound was synthesized in analogy to the procedure described for the preparation of Example 43, using 5-bromo-6-chloro-nicotinic acid methyl ester, 4-chlorophenyl-boronic acid (commercially available), rac-1-methoxy-2-propanol (commercially available), and (1R,2R)-2-amino-cyclohexanol (commercially available) as starting materials. MS (ISP): 419.1 (M+H$^+$).

Example 49

Preparation of 5-(4-Chloro-phenyl)-N-((1R,2R)-2-hydroxy-cyclohexyl)-6-(1-methoxymethyl-propoxy)-nicotinamide The title compound was synthesized in analogy to the procedure described for the preparation of Example 43, using 5-bromo-6-chloro-nicotinic acid methyl ester, 4-chlorophenyl-boronic acid (commercially available), rac-1-methoxy-2-butanol (commercially available), and (1R,2R)-2-amino-cyclohexanol (commercially available) as starting materials. MS (ISP): 433.3, 435.3 (M+H$^+$).

Example 50

Preparation of 6-(4-Fluoro-phenyl)-5-((S)-2-methoxy-propoxy)-pyrazine-2-carboxylic Acid (2-cyclopropyl-2-hydroxy-propyl)-amide The title compound was synthesized in analogy to the procedure described for the preparation of Example 40 using 5-bromo-3-(4-fluoro-phenyl)-pyrazin-2-ylamine, (S)-(+)-2-methoxypropanol (commercially available), and rac-1-amino-2-cyclopropyl-propan-2-ol (commercially available) as starting materials to give the title compound as a colorless oil. MS (ISP): 404.4 (M+H)$^+$.

Example 51

Preparation of 5-(4-Chloro-phenyl)-N-((1R,2R)-2-hydroxy-cyclohexyl)-6-isobutoxy-nicotinamide The title compound was synthesized in analogy to the procedure described for the preparation of Example 31, using 5-bromo-6-chloro-3-pyridinecarboxylic acid, 2-methyl-1-propanol (commercially available), 4-chlorophenyl-boronic acid (commercially available), and (1R,2R)-2-amino-cyclohexanol (commercially available) as starting materials. MS (ISP): 403.4 (M+H$^+$).

Example 52

Preparation of 5-(4-Chloro-phenyl)-6-(2-ethoxy-ethoxy)-N-((1R,2R)-2-hydroxy-cyclohexyl)-nicotinamide The title compound was synthesized in analogy to the procedure described for the preparation of Example 31, using 5-bromo-6-chloro-3-pyridinecarboxylic acid, 2-ethoxyethanol (commercially available), 4-chlorophenyl-boronic acid (commercially available), and (1R,2R)-2-amino-cyclohexanol (commercially available) as starting materials. MS (ISP): 419.3 (M+H$^+$).

Example 53

Preparation of 6-(4-Chloro-phenyl)-5-[(R)-1-(tetrahydro-furan-2-yl)methoxy]-pyrazine-2-carboxylic Acid ((S)-2-cyclopropyl-2-hydroxy-propyl)-amide The title compound was synthesized in analogy to the procedure described for the preparation of Example 39 using 5-bromo-3-(4-chloro-phenyl)-pyrazin-2-ylamine, (R)-(−)-2-(hydroxymethyl)tetrahydrofurane (commercially available), and (S)-α-(aminomethyl)-α-methyl-cyclopropanemethanol (WO 2006/106054) as starting materials to give the title compound as a colorless foam. MS (ISP): 432.3, 434.3 (M+H)$^+$.

Example 54

Preparation of 6-(4-Chloro-phenyl)-5-[(R)-1-(tetrahydro-furan-2-yl)methoxy]-pyrazine-2-carboxylic Acid ((R)-2-cyclopropyl-2-hydroxy-propyl)-amide The title compound was synthesized in analogy to the procedure described for the preparation of Example 39 using 5-bromo-3-(4-chloro-phenyl)-pyrazin-2-ylamine, (R)-(−)-2-(hydroxymethyl)tetrahydrofurane (commercially available), and (R)-α-(aminomethyl)-α-methyl-cyclopropanemethanol (WO 2006/106054) as starting materials to give the title compound as a colorless foam. MS (ISP): 432.3 (M+H)$^+$.

Example 55

Preparation of 5-(4-Chloro-phenyl)-N-((1R,2R)-2-hydroxy-cyclohexyl)-6-((S)-2-methoxy-propoxy)-nicotinamide The title compound was synthesized in analogy to the procedure described for the preparation of Example 31, using 5-bromo-6-chloro-3-pyridinecarboxylic acid, (S)-(+)-2-methoxypropanol (commercially available), 4-chlorophenyl-boronic acid (commercially available), and (1R,2R)-2-amino-cyclohexanol (commercially available) as starting materials. MS (ISP): 419.2 (M+H$^+$).

Example 56

Preparation of 6-sec-Butoxy-5-(4-chloro-phenyl)-N-((1R,2R)-2-hydroxy-cyclohexyl)-nicotinamide The title compound was synthesized in analogy to the procedure described for the preparation of Example 31, using 5-bromo-6-chloro-3-pyridinecarboxylic acid, rac-2-butanol (commercially available), 4-chlorophenyl-boronic acid (commercially available), and (1R,2R)-2-amino-cyclohexanol (commercially available) as starting materials. MS (ISP): 403.2 (M+H$^+$).

Example 57

Preparation of 5-(4-Chloro-phenyl)-N-((1R,2R)-2-hydroxy-cyclohexyl)-6-(oxetan-2-ylmethoxy)-nicotinamide The title compound was synthesized in analogy to the procedure described for the preparation of Example 31, using 5-bromo-6-chloro-3-pyridinecarboxylic acid, rac-2-hydroxymethyloxetane (commercially available), 4-chlorophenyl-boronic acid (commercially available), and (1R,2R)-2-amino-cyclohexanol (commercially available) as starting materials. MS (ISP): 417.2 (M+H$^+$).

Example 58

Preparation of 5-(2-Methoxy-ethoxy)-6-(4-trifluoromethyl-phenyl)-pyrazine-2-carboxylic Acid (2-cyclopropyl-2-hydroxy-propyl)-amide The title compound was synthesized in analogy to the procedure described for the preparation of Example 40a to b using 2-amino-3,5-dibromopyrazine, 4-trifluoromethylphenylboronic acid, 2-methoxy-ethanol (commercially available), and rac-1-amino-2-cyclopropyl-propan-2-ol as starting materials to give the title compound as a colorless oil, MS (ISP): 440.3 (M+H)$^+$.

Example 59

Preparation of 5-Cyclopropylmethoxy-6-(4-trifluoromethyl-phenyl)-pyrazine-2-carboxylic Acid (2-cyclopropyl-2-hydroxy-propyl)-amide The title compound was synthesized in analogy to the procedure described for the preparation of Example 40a to b, using 2-amino-3,5-dibromopyrazine, 4-trifluoromethylphenylboronic acid, hydroxymethylcyclopropane (commercially available), and rac-1-amino-2-cyclopropyl-propan-2-ol as starting materials to give the title compound as a colorless oil, MS (ISP): 436.1 (M+H)$^+$.

Example 60

Preparation of 5-(3-Methoxy-propoxy)-6-(4-trifluoromethyl-phenyl)-pyrazine-2-carboxylic Acid (2-cyclopropyl-2-hydroxy-propyl)-amide The title compound was synthesized in analogy to the procedure described for the preparation of Example 40a to b, using 2-amino-3,5-dibromopyrazine, 4-trifluoromethylphenylboronic acid, 3-methoxy-1-propanol (commercially available), and rac-1-amino-2-cyclopropyl-propan-2-ol as starting materials to give the title compound as a colorless oil, MS (ISP): 454.2 (M+H)$^+$.

Example 61

Preparation of 5-Butoxy-6-(4-trifluoromethyl-phenyl)-pyrazine-2-carboxylic Acid (2-cyclopropyl-2-hydroxy-propyl)-amide The title compound was synthesized in analogy to the procedure described for the preparation of Example 40a to b, using 2-amino-3,5-dibromopyrazine, 4-trifluoromethylphenylboronic acid, 1-butanol (commercially available), and rac- 1-amino-2-cyclopropyl-propan-2-ol as starting materials to give the title compound as a colorless oil, MS (ISP): 438.1 (M+H)+.

Example 62

Preparation of 6-(4-Chloro-phenyl)-5-pyrrolidin-1-yl-pyrazine-2-carboxylic Acid ((R)-2-cyclopropyl-2-hydroxy-propyl)-amide a) 5-Bromo-6-(4-chloro-phenyl)-pyrazine-2-carboxylic Acid ((R)-2-cyclopropyl-2-hydroxy-propyl)-amide The title compound was synthesized in analogy to the procedure described for the preparation of Example 39a to d using 5-bromo-3-(4-chloro-phenyl)-pyrazin-2-ylamine (Example 36a), and (R)-α-(aminomethy)-α-methyl-cyclopropanemethanol (WO 2006/106054) as starting materials to give the title compound as an off-white solid, mp.: 125-126° C.

b) 6-(4-Chloro-phenyl)-5-pyrrolidin-1-yl-pyrazine-2-carboxylic Acid ((R)-2-cyclopropyl-2-hydroxy-propyl)-amide To a solution of 0.020 g of 5-bromo-6-(4-chloro-phenyl)-pyrazine-2-carboxylic acid ((R-2-cyclopropyl-2-hydroxy-propyl)-amide in 2 ml dimethylsulfoxide was added at room temperature 0.017 g of pyrrolidine. The mixture was stirred for 6 hours. The starting material was completely consumed, as evidenced by HPLC and TLC. The reaction mixture was partitioned between 10% citric acid and ethyl acetate. The phases were separated and the organic layer was washed with 10% sodium bicarbonate and brine and dried over magnesium sulfate and evaporated. The residue was purified by chromatography on silica gel to yield 0.017 g (89% yield) of the title compound as white foam. MS (ISP) (M+H+)=401.3.

Example 63

Preparation of 6-(4-Chloro-phenyl)-5-(3-methyl-butylamino)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and isoamylamine as starting materials to give the title compound as a white foam, MS (ISP): 417.4 (M+H)+.

Example 64

Preparation of 6-(4-Chloro-phenyl)-5-(cyclopropyl-methyl-amino)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and aminomethylcyclopropane as starting materials to give the title compound as a colorless oil, MS (ISP): 401.3 (M+H)+.

Example 65

Preparation of 6-(4-Chloro-phenyl)-5-cyclopropylamino-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and cyclopropylamine as starting materials to give the title compound as a colorless oil, MS (ISP): 387.3 (M+H)+.

Example 66

Preparation of 6-(4-Chloro-phenyl)-5-(3-methoxy-azetidin-1-yl)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and 3-methoxy-azetidine (CAN 110925-17-2) as starting materials to give the title compound as a colorless oil, MS (ISP): 417.5 (M+H)+.

Example 67

Preparation of 6-(4-Chloro-phenyl)-5-(3-hydroxy-azetidin-1-yl)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and 3-hydroxy-azetidine (CAN 45347-82-8) as starting materials to give the title compound as an off-white foam, MS (ISP): 403.3 (M+H)+.

Example 68

Preparation of 5-(4-Chloro-phenyl)-N-(2-cyclopropyl-2-hydroxy-propyl)-6-(2,2,2-trifluoro-ethoxy)-nicotinamide The title compound was synthesized in analogy to the procedure described for the preparation of Example 5, using 5-bromo-6-chloro-nicotinic acid methylester, 2,2,2-trifluoro-ethanol (commercially available), 4-chlorophenyl-boronic acid (commercially available) and rac-1-amino-2-cyclopropyl-propan-2-ol (commercially available) as starting materials. MS (ISP): 429.1 (M+H+).

Example 69

Preparation of N-((1R,2R)-2-Hydroxy-cyclohexyl)-6-(2,2,2-trifluoro-ethoxy)-5-(4-trifluoromethyl-phenyl)-nicotinamide The title compound was synthesized in analogy to the procedure described for the preparation of Example 5, using 5-bromo-6-chloro-nicotinic acid methylester, 2,2,2-trifluoro-ethanol (commercially available), 4-trifluoromethylphenyl-boronic acid (commercially available) and (1R,2R)-2-amino-cyclohexanol (commercially available) as starting materials. MS (ISP): 463.1 (M+H+).

Example 70

Preparation of 5-(4-Chloro-phenyl)-N-((1R,2R)-2-hydroxy-cyclohexyl)-6-[3-(2-oxo-pyrrolidin-1-yl)-propoxy]-nicotinamide The title compound was synthesized in analogy to the procedure described for the preparation of Example 6, using 5-bromo-1,6-dihydro-6-oxo-3-pyridinecarboxylic acid methyl ester, 1-(3-hydroxypropyl)-2-pyrrolidone (commercially available), 4-chlorophenyl-boronic acid (commercially available) and (1R,2R)-2-amino-cyclohexanol (commercially available) as starting materials. MSA^(ISP): 472.1 (M+H$^+$).

Example 71

Preparation of 5-Cyclopropylmethoxy-6-(4-fluoro-phenyl)-pyrazine-2-carboxylic Acid ((R)-2-cyclopropyl-2-hydroxy-propyl)-amide The title compound was synthesized in analogy to the procedure described for the preparation of Example 36 using 5-bromo-3-(4-fluoro-phenyl)-pyrazine-2-ylamine (example 40 a), (R)-α-(aminomethyl)-α-methyl-cyclopropanemethanol (WO 2006/106054) and hydroxymethylcyclopropane as starting materials to give the title compound as an off-white solid, MS (ISP): 386.3 (M+H)$^+$.

Example 72

Preparation of 5-Cyclopropylmethoxy-6-(4-fluoro-phenyl)-pyrazine-2-carboxylic Acid ((S)-2-cyclopropyl-2-hydroxy-propyl)-amide The title compound was synthesized in analogy to the procedure described for the preparation of Example 36 using 5-bromo-3-(4-fluoro-phenyl)-pyrazine-2-ylamine (example 40 a), (S)-α-(aminomethyl)-α-methyl-cyclopropanemethanol (WO 2006/106054) and hydroxymethylcyclopropane as starting materials to give the title compound as an off-white solid, MS (ISP): 386.3 (M+H)$^+$.

Example 73

Preparation of 5-(4-Fluoro-phenyl)-N-((1R,2R)-2-hydroxy-cyclohexyl)-6-(3-methoxy-propoxy)-nicotinamide The title compound was synthesized in analogy to the procedure described for the preparation of Example 31, using 5-bromo-6-chloro-3-pyridinecarboxylic acid, 3-methoxy-1-propanol (commercially available), 4-fluorophenyl-boronic acid (commercially available), and (1R,2R)-2-amino-cyclohexanol (commercially available) to give the title compound as a colorless solid, MS (ISP): 403.5 (M+H)$^+$.

Example 74

Preparation of 6-(4-Chloro-phenyl)-5-(2,2,2-trifluoro-ethoxy)-pyrazine-2-carboxylic Acid ((R)-2-cyclopropyl-2-hydroxy-propyl)-amide To a solution of 0.041 g (0.001 mol) 5-bromo-6-(4-chlorophenyl)-pyrazine-2-carboxylic acid ((R)-2-cyclopropyl-2-hydroxy-propyl)-amide (example 62a) in 1.0 ml 2,2,2-trifluoroethanol was added 0.200 g (0.006 mol) cesium carbonate and the mixture was stirred at room temperature for 7 days. The reaction mixture was partitioned between water and ethyl acetate, the phases were separated and the organic phase was purified by chromatography on silica gel with heptane:ethyl acetate=2:1 to yield 0.042 g (98% yield) of the title compound as white crystals melting at 96-97° C.

Example 75

Preparation of 6-(4-Chloro-phenyl)-5-[(S)-1-(tetrahydro-furan-2-yl)methoxy]-pyrazine-2-carboxylic Acid ((S)-2-cyclopropyl-2-hydroxy-propyl)-amide The title compound was synthesized in analogy to the procedure described for the preparation of Example 39 using 5-bromo-3-(4-chloro-phenyl)-pyrazine-2-ylamine, (S)-α-(aminomethyl)-α-methyl-cyclopropanemethanol (WO 2006/106054) and (S)-(−)-tetrahydrofurfuryl alcohol as starting materials to give the title compound as an off-white solid, MS (ISP): 432.0 (M+H)$^+$.

Example 76

Preparation of 5-(4-Chloro-phenyl)-6-(cyclopropylmethyl-methyl-amino)-N-((1R,2R)-2-hydroxy-cyclohexyl)-nicotinamide The title compound was synthesized in analogy to the procedure described for the preparation of Example 43, using 5-bromo-6-chloro-nicotinic acid methyl ester, cyclopropylmethyl methylamine hydrochloride, (commercially available), 4-chlorophenyl-boronic acid (commercially available) and (1R,2R)-2-amino-cyclohexanol (commercially available) as starting materials. MS (ISP): 414.3 (M+H$^+$).

Example 77

Preparation of 6-(Cyclopropylmethyl-methyl-amino)-5-(4-fluoro-phenyl)-N-((1R,2R)-2-hydroxy-cyclohexyl)-nicotinamide The title compound was synthesized in analogy to the procedure described for the preparation of Example 43, using 5-bromo-6-chloro-nicotinic acid methyl ester, cyclopropylmethyl methylamine hydrochloride (commercially available), 4-fluorophenyl-boronic acid (commercially available) and (1R,2R)-2-amino-cyclohexanol (commercially available) as starting materials. MS (ISP): 398.3 (M+H$^+$).

Example 78

Preparation of N-(2-Cyclopropyl-2-hydroxy-propyl)-6-(cyclopropylmethyl-methyl-amino)-5-(4-fluoro-phenyl)-nicotinamide The title compound was synthesized in analogy to the procedure described for the preparation of Example 43, using 5-bromo-6-chloro-nicotinic acid methyl ester, cyclopropylmethyl methylamine hydrochloride, (commercially available), 4-fluorophenyl-boronic acid (commercially available) and rac-1-amino-2-cyclopropyl-propan-2-ol (commercially available) as starting materials. MS (ISP): 398.0 (M+H$^+$).

Example 79

Preparation of N—((S)-2-Cyclopropyl-2-hydroxy-propyl)-6-cyclopropylmethoxy-5-(4-trifluoromethyl-phenyl)-nicotinamide The title compound was synthesized in analogy to the procedure described for the preparation of Example 43, using 5-bromo-6-chloro-nicotinic acid methyl ester, hydroxymethylcyclopropane (commercially available), 4-trifluoromethylphenyl-boronic acid (commercially available) and (S)-α-(aminomethyl)-α-methyl-cyclopropanemethanol (WO 2006/106054) as starting materials. MS (ISP): 435.3 (M+H$^+$).

Example 80

Preparation of 5-Butoxy-6-(4-chloro-phenyl)-pyrazine-2-carboxylic Acid ((R)-2-cyclopropyl-2-hydroxy-propyl)-amide The title compound was synthesized in analogy to the procedure described for the preparation of Example 39 using 5-bromo-3-(4-chloro-phenyl)-pyrazine-2-ylamine, (R)-α-(aminomethyl)-α-methyl-cyclopropanemethanol (WO 2006/106054) and 1-butanol as starting materials to give the title compound as a colorless oil, MS (ISP): 404.4 (M+H)$^+$.

Example 81

Preparation of 5-(4-Chloro-phenyl)-N-((1R,2R)-2-hydroxy-cyclohexyl)-6-(methyl-propyl-amino)-nicotinamide The title compound was synthesized in analogy to the procedure described for the preparation of Example 43, using 5-bromo-6-chloro-nicotinic acid methyl ester, N-methyl-N-propylamine, (4-chloro-phenyl)-boronic acid and (1R,2R)-2-amino-cyclohexanol hydrochloride as starting materials. MS (ISP): 402.3 (M+H$^+$).

Example 82

Preparation of 5-(4-Chloro-phenyl)-N-(2-cyclopropyl-2-hydroxy-propyl)-6-(methyl-propyl-amino)-nicotinamide The title compound was synthesized in analogy to the procedure described for the preparation of Example 43, using 5-bromo-6-chloro-nicotinic acid methyl ester, N-methyl-N-propylamine, (4-chloro-phenyl)-boronic acid and rac-1-amino-2-cyclopropyl-propan-2-ol as starting materials. MS (ISP): 402.5 (M+H$^+$).

Example 83

Preparation of 5-Cyclopropylmethoxy-6-(4-trifluoromethyl-phenyl)-pyrazine-2-carboxylic Acid ((R)-2-cyclopropyl-2-hydroxy-propyl)-amide The title compound was synthesized in analogy to the procedure described for the preparation of Example 40 using 2-amino-3,5-bromo-pyrazine, 4-trifluoromethyl-phenyl-boronic acid, (R)-α-(aminomethyl)-α-methyl-cyclopropanemethanol (WO 2006/106054) and hydroxymethylcyclopropane as starting materials to give the title compound as a colorless oil, MS (ISP): 436.1 (M+H)$^+$.

Example 84

Preparation of 5-Azepan-1-yl-6-(4-chloro-phenyl)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and hexamethylene imine as starting materials to give the title compound as a colorless oil. MS (ISP): 429.5 (M+H)$^+$.

Example 85

Preparation of 5-[Methyl-(3-methyl-butyl)-amino]-6-(4-trifluoromethyl-phenyl)-pyrazine-2-carboxylic Acid ((R)-2-cyclopropyl-2-hydroxy-propyl)-amide a) 5-Bromo-3-(4-trifluoro-phenyl)-pyrazin-2-ylamine The title compound was synthesized in analogy to the procedure described for the preparation of Example 19a using 2-amino-3,5-dibromopyrazine, and 4-trifluoro-methylphenylboronic acid (commercially available) as starting materials to give the title compound as a yellow solid, MS (ISP) 317.9, 320.0 (M+H)$^+$.

b) 5-Bromo-6-(4-trifluoromethyl-phenyl)-pyrazine-2-carboxylic Acid ((R-2-cyclopropyl-2-hydroxy-propyl)-amide The title compound was synthesized in analogy to the procedure described for the preparation of Example 39a to d using 5-bromo-3-(4-trifluoro-phenyl)-pyrazin-2-ylamine, and (R)-α-(aminomethyl)-α-methyl-cyclopropanemethanol (WO 2006/106054) as starting materials to give the title compound as a colorless foam, MS (ISP): 444.1, 446.0 (M+H)$^+$.

c) 5-[Methyl-(3-methyl-butyl)-amino]-6-(4-trifluoromethyl-phenyl)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-trifluoromethyl-phenyl)-pyrazine-2-carboxylic acid ((R-2-cyclopropyl-2-hydroxy-propyl)-amide and methylisoamylamine as starting materials to give the title compound as an off-white oil.
MS (ISP): 465.5 (M+H)$^+$.

Example 86

Preparation of N—((S)-2-Cyclopropyl-2-hydroxy-propyl)-6-(2-methoxy-ethoxy)-5-(4-trifluoromethyl-phenyl)-nicotinamide The title compound was synthesized in analogy to the procedure described for the preparation of Example 43, using 5-bromo-6-chloro-nicotinic acid methyl ester, methoxyethanol (commercially available), 4-trifluoromethylphenylboronic acid (commercially available) and rac-1-amino-2-cyclopropyl-propan-2-ol (commercially available) as starting

Example 87

Preparation of 5-(4-Chloro-phenyl)-N-(2-cyclopropyl-2-hydroxy-propyl)-6-[(2-methoxy-ethyl)-methyl-amino]-nicotinamide The title compound was synthesized in analogy to the procedure described for the preparation of Example 43, using 5-bromo-6-chloro-nicotinic acid methyl ester, N-(2-methoxyethyl)methylamine (commercially available), 4-chlorophenyl-boronic acid (commercially available) and rac-1-amino-2-cyclopropyl-propan-2-ol (commercially available) as starting materials. MS (ISP): 418.3 (M+H$^+$).

Example 88

Preparation of 5-(4-Fluoro-phenyl)-N-((1R,2R)-2-hydroxy-cyclohexyl)-6-(methyl-propyl-amino)-nicotinamide The title compound was synthesized in analogy to the procedure described for the preparation of Example 43, using 5-bromo-6-chloro-nicotinic acid methyl ester, N-methyl-N-propylamine (commercially available), 4-fluorophenyl-boronic acid (commercially available) and (1R,2R)-2-aminocyclohexanol (commercially available) as starting materials. MS (ISP): 386.2 (M+H$^+$).

Example 89

Preparation of N—((R)-2-Cyclopropyl-2-hydroxy-propyl)-6-cyclopropylmethoxy-5-(4-fluoro-phenyl)-nicotinamide The title compound was synthesized in analogy to the procedure described for the preparation of Example 43, using 5-bromo-6-chloro-nicotinic acid methyl ester, cyclopropylmethanol (commercially available), 4-fluorophenylboronic acid (commercially available) and rac-1-amino-2-cyclopropyl-propan-2-ol (commercially available) as starting materials. The two enantiomers were separated by column chromatography on chiral phase. MS (ISP): 385.3 (M+H$^+$).

Example 90

Preparation of 3'-(4-Chloro-phenyl)-3,4,5,6-tetrahydro-2H-[1,2']bipyridinyl-5'-carboxylic Acid (2-cyclopropyl-2-hydroxy-propyl)-amide The title compound was synthesized in analogy to the procedure described for the preparation of Example 43, using 5-bromo-6-chloro-nicotinic acid methyl ester, piperidine (commercially available), 4-chlorophenyl-boronic acid (commercially available) and rac-1-amino-2-cyclopropyl-propan-2-ol (commercially available) as starting materials. MS (ISP): 414.4 (M+H$^+$).

Example 91

Preparation of N—((S)-2-Cyclopropyl-2-hydroxy-propyl)-6-cyclopropylmethoxy-5-(4-trifluoromethoxy-phenyl)-nicotinamide The title compound was synthesized in analogy to the procedure described for the preparation of Example 43, using 5-bromo-6-chloro-nicotinic acid methyl ester, cyclopropylmethanol (commercially available), 4-trifluoromethoxyphenylboronic acid (commercially available) and rac-1-amino-2-cyclopropyl-propan-2-ol (commercially available) as starting materials. The two enantiomers were separated by column chromatography on chiral phase. MS (ISP): 451.1 (M+H$^+$).

Example 92

Preparation of 5-(4-Chloro-phenyl)-N—((S)-2-cyclopropyl-2-hydroxy-propyl)-6-(2-methyl-2H-[1,2,4]triazol-3-ylmethoxy)-nicotinamide The title compound was synthesized in analogy to the procedure described for the preparation of Example 5, using 5-bromo-6-chloro-3-pyridinecarboxylic acid methyl ester, 4-chlorophenyl-boronic acid (commercially available), 1-methyl-1H-1,2,4-triazole-5-methanol (CAN 91616-36-3), and (S)-α-(aminomethyl)-α-methyl-cyclopropanemethanol (WO 2006/106054) as starting materials. MS (ISP): 442.1 (M+H$^+$).

Example 93

Preparation of 5-(4-Chloro-phenyl)-N-((1R,2R)-2-hydroxy-cyclohexyl)-6-(1-methyl-1H-imidazol-2-ylmethoxy)-nicotinamide a) 5-Bromo-6-(1-methyl-1H-imidazol-2-ylmethoxy)-Nicotinic Acid Methyl Ester 5-Bromo-6-hydroxy-3-pyridinecarboxylic acid methyl ester (1.0 g, 4.3 mmol) was suspended in tetrahydrofurane, 1-methyl-1H-imidazole-2-methanol (0.72 g, 6.5 mmol) and triphenylphosphine was added (1.70 g, 6.5 mmol). To this mixture was added with stirring diisopropyl-azodicarboxylate (1.35 mL, 6.5 mmol) at room temperature. Stirring was continued for 1 h at room temperature, solvent was removed and the residue was purified by chromatography with heptane/ethylacetate/methanol on silica gel to yield 0.38 g of the title compound as a colorless solid, MS (ISP) 326.0, 328.0 (M+H)$^+$.

b) 5-(4-Chloro-phenyl)-6-(1-methyl-1H-imidazol-2-ylmethoxy)-Nicotinic Acid Methyl Ester 5-Bromo-6-(1-methyl-1H-imidazol-2-ylmethoxy)-nicotinic acid methyl ester (0.35 g, 1.1 mmol) was dissolved in toluene (6 mL). To this solution was added (4-chloro-phenyl)-boronic acid (0.17 g, 1.1 mmol), [1,1'-bis(diphenylphosphino)ferrocene]dichloropalladium(II) dichloro-methane complex (43 mg), and 2 N sodium carbonate solution (2 mL). The whole mixture was heated with stirring at 90° C. for 18 h, cooled to room temperature and eluted with ethyl acetate over 10 g ChemElut (Varian). The solvent was evaporated and the residue was purified by column chromatography on silica (n-heptane/ethyl acetate gradient) to yield 0.29 g of the title compound as an off-white solid, MS (ISP) 358.1 (M+H)$^+$.

c) 5-(4-Chloro-phenyl)-6-(1-methyl-1H-imidazol-2-ylmethoxy)-nicotinic Acid 5-(4-Chloro-phenyl)-6-(1-methyl-1H-imidazol-2-ylmethoxy)-nicotinic acid methyl ester (0.28 g, 0.8 mmol) was dissolved in tetrahydrofuran (4.5 mL). Water (1.5 mL) and lithium hydroxide (99 mg, 2.3 mmol) was added and the mixture was stirred for 1 h at 80° C. The mixture was cooled to room temperature; citric acid (4 mL, 10%) was added and the mixture was extracted with ethyl acetate. Organic phases were pooled dried with $Na_2SO_4$ and the solvent evaporated to give a quantitative yield of the title compound as beige solid, MS (ISP) 342.0 $(M-H)^-$.

d) 5-(4-Chloro-phenyl)-N-((1R,2R)-2-hydroxy-cyclohexyl)-6-(1-methyl-1H-imidazol-2-ylmethoxy)-nicotinamide The title compound was synthesized in analogy to Example 5d, using 5-(4-chloro-phenyl)-6-(1-methyl-1H-imidazol-2-ylmethoxy)-nicotinic acid and (1R,2R)-2-amino-1-cyclohexanol as starting materials to yield 5-(4-chloro-phenyl)-N-((1R,2R)-2-hydroxy-cyclohexyl)-6-(1-methyl-1H-imidazol-2-ylmethoxy)-nicotinamide, MS (ISP) 441.2 $(M+H)^+$.

Example 94

Preparation of 5-(4-Chloro-phenyl)-N-((1R,2R)-2-hydroxy-cyclohexyl)-6-(2-methyl-2H-[1,2,4]triazol-3-ylmethoxy)-nicotinamide The title compound was synthesized in analogy to the procedure described for the preparation of Example 5, using 5-bromo-6-chloro-3-pyridinecarboxylic acid methyl ester, 4-chlorophenyl-boronic acid (commercially available), 1-methyl-1H-1,2,4-triazole-5-methanol (CAN 91616-36-3), and (1R,2R)-2-amino-1-cyclohexanol as starting materials. MS (ISP): 442.1 $(M+H^+)$.

Example 95

Preparation of 5-(4-Chloro-phenyl)-N—((S)-2-cyclopropyl-2-hydroxy-propyl)-6-(pyridin-4-yl-methoxy)-nicotinamide The title compound was synthesized in analogy to the procedure described for the preparation of Example 5, using 5-bromo-6-chloro-3-pyridinecarboxylic acid methyl ester, 4-chlorophenyl-boronic acid (commercially available), 4-(hydroxymethyl)-pyridine, and (S)-α-(aminomethyl)-α-methyl-cyclopropanemethanol (WO 2006/106054) as starting materials. MS (ISP): 438.1 $(M+H^+)$.

Example 96

Preparation of 6-(4-Fluoro-phenyl)-5-(2,2,2-trifluoro-ethoxy)-pyrazine-2-carboxylic Acid ((S)-2-cyclopropyl-2-hydroxy-propyl)-amide The title compound was synthesized in analogy to the procedure described for the preparation of Example 36 using 5-bromo-3-(4-fluoro-phenyl)-pyrazine-2-ylamine (example 40 a) and (S)-α-(aminomethyl)-α-methyl-cyclopropanemethanol (WO 2006/106054) as starting materials to produce 5-bromo-6-(4-fluoro-phenyl)-pyrazine-2-carboxylic acid ((S)-2-cyclopropyl-2-hydroxy-propyl)-amide and in analogy to Example 74 reaction with 2,2,2-trifluoroethanol to give the title compound as a white solid, MS (ISP): 414.5 $(M+H)^+$.

Example 97

Preparation of 6-(4-Fluoro-phenyl)-5-(2,2,2-trifluoro-ethoxy)-pyrazine-2-carboxylic Acid ((1R,2R)-2-hydroxy-cyclohexyl)-amide The title compound was synthesized in analogy to the procedure described for the preparation of Example 36 using 5-bromo-3-(4-fluoro-phenyl)-pyrazine-2-ylamine (example 40 a) and (1R,2R)-2-amino-1-cyclohexanol as starting materials to produce 5-bromo-6-(4-fluoro-phenyl)-pyrazine-2-carboxylic acid ((1R,2R)-2-hydroxy-cyclohexyl)-amide and in analogy to Example 74 reaction with 2,2,2-trifluoroethanol to give the title compound as a white solid, mp.: 133-134° C.

Example 98

Preparation of 6-(4-Chloro-phenyl)-5-[(2-hydroxy-ethyl)-methyl-amino]-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and 2-(methylamino)ethanol as starting materials to give the title compound as a light yellow oil. MS (ISP): 405.3 $(M+H)^+$.

Example 99

Preparation of 6-(4-Fluoro-phenyl)-5-(2-methoxy-ethoxy)-pyrazine-2-carboxylic Acid ((1R,2R)-2-hydroxy-cyclohexyl)-amide The title compound was synthesized in analogy to the procedure described for the preparation of Example 36 using 5-bromo-3-(4-fluoro-phenyl)-pyrazine-2-ylamine (example 40 a), (1R,2R)-2-amino-1-cyclohexanol and 2-methoxyethanol as starting materials to give the title compound as a white solid, MS (ISP): 390.4 $(M+H)^+$.

Example 100

Preparation of 5-Cyclopropylmethoxy-6-(4-fluoro-phenyl)-pyrazine-2-carboxylic Acid ((1R,2R)-2-hydroxy-cyclohexyl)-amide The title compound was synthesized in analogy to the procedure described for the preparation of Example 36 using 5-bromo-3-(4-fluoro-phenyl)-pyrazine-2-ylamine (example 40 a), (1R,2R)-2-amino-1-cyclohexanol and hydroxymethyl-cyclopropane as starting materials to give the title compound as a white foam, MS (ISP): 386.3 $(M+H)^+$.

Example 101

Preparation of 5-(4-Cyano-phenyl)-N—((R)-2-cyclopropyl-2-hydroxy-propyl)-6-cyclopropylmethoxy-nicotinamide The title compound was synthesized from 5-bromo-6-cyclopropylmethoxy-nicotinic acid (example 31 a) by Suzuki reaction with 4-cyanophenyl-boronic acid (in analogy to 31 c)

and amide coupling with (R)-α-(aminomethyl)-α-methyl-cyclopropanemethanol (WO 2006/106054) (in analogy to example 31b), to give the title compound as a white solid, MS (ISP): 392.2 (M+H)$^+$.

Example 102

Preparation of 5-(4-Chloro-phenyl)-N—((R)-2-cyclopropyl-2-hydroxy-propyl)-6-cyclopropylmethoxy-nicotinamide The title compound was synthesized in analogy to Example 31, using 5-bromo-6-chloro-3-pyridinecarboxylic acid, cyclopropanemethanol, (4-chloro-phenyl)-boronic acid and (R)-α-(aminomethyl)-α-methyl-cyclopropanemethanol as starting materials to yield 5-(4-chloro-phenyl)-N—((R)-2-cyclopropyl-2-hydroxy-propyl)-6-cyclopropylmethoxy-nicotinamide as a white solid, MS (ISP) 401.3 (M+H)$^+$.

Example 103

Preparation of 5-(4-Chloro-phenyl)-N—((S)-2-cyclopropyl-2-hydroxy-propyl)-6-cyclopropylmethoxy-nicotinamide The title compound was synthesized in analogy to Example 31, using 5-bromo-6-chloro-3-pyridinecarboxylic acid, cyclopropanemethanol, (4-chloro-phenyl)-boronic acid and (S)-α-(aminomethyl)-α-methyl-cyclopropanemethanol as starting materials to yield 5-(4-chloro-phenyl)-N—((S)-2-cyclopropyl-2-hydroxy-propyl)-6-cyclopropylmethoxy-nicotinamide as a colorless solid, MS (ISP) 401.3 (M+H)$^+$.

Example 104

Preparation of 5-(4-Chloro-phenyl)-N—((R)-2-cyclopropyl-2-hydroxy-propyl)-6-(3-methyl-isoxazol-5-ylmethoxy)-nicotinamide The title compound was synthesized in analogy to Example 31, using 5-bromo-6-chloro-3-pyridinecarboxylic acid, 3-methyl-5-isoxazolemethanol, (4-chloro-phenyl)-boronic acid and (R)-α-(aminomethyl)-α-methyl-cyclopropanemethanol as starting materials to yield 5-(4-chloro-phenyl)-N—((R)-2-cyclopropyl-2-hydroxy-propyl)-6-(3-methyl-isoxazol-5-ylmethoxy)-nicotinamide as a white foam, MS (ISP) 442.1 (M+H)$^+$.

Example 105

Preparation of 6-Cyclopropylmethoxy-5-(4-fluoro-phenyl)-N-(1-hydroxymethyl-cyclopentyl)-nicotinamide The title compound was synthesized in analogy to Example 31, using 5-bromo-6-chloro-3-pyridinecarboxylic acid, hydroxymethylcyclopropanol, (4-fluoro-phenyl)-boronic acid and 1-amino-cyclopentanemethanol as starting materials to yield 6-cyclopropylmethoxy-5-(4-fluoro-phenyl)-N-(1-hydroxymethyl-cyclopentyl)-nicotinamide as a colorless foam, MS (ISP) 385.1 (M+H)$^+$.

Example 106

Preparation of 5-[Bis-(2-hydroxy-ethyl)-amino]-6-(4-chloro-phenyl)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and diethanoamine as starting materials to give the title compound as a light yellow oil. MS (ISP): 435.3 (M+H)$^+$.

Example 107

Preparation of 5-Cyclopropylmethoxy-6-(4-trifluoromethoxy-phenyl)-pyrazine-2-carboxylic Acid ((1R,2R)-2-hydroxy-cyclohexyl)-amide The title compound was synthesized in analogy to the procedure described for the preparation of Example 36 using 5-bromo-3-(4-trifluoromethoxy-phenyl)-pyrazine-2-ylamine (prepared in analogy to example 40a), (1R,2R)-2-amino-1-cyclohexanol and hydroxymethylcyclopropane as starting materials to give the title compound as a white foam, MS (ISP): 452.3 (M+H)$^+$.

Example 108

Preparation of 5-(Cyclopropylmethyl-methyl-amino)-6-(4-trifluoromethoxy-phenyl)-pyrazine-2-carboxylic Acid ((1R,2R)-2-hydroxy-cyclohexyl)-amide The title compound was synthesized in analogy to the procedure described for the preparation of Example 62 using 5-bromo-3-(4-trifluoromethoxy-phenyl)-pyrazine-2-ylamine (prepared in analogy to example 40a), (1R,2R)-2-amino-1-cyclohexanol and cyclopropylmethyl-methyl-amine hydrochloride as starting materials to give the title compound as an off-white foam, MS (ISP): 465.4 (M+H)$^+$.

Example 109

Preparation of 5-Cyclopropylmethoxy-6-(4-trifluoromethoxy-phenyl)-pyrazine-2-carboxylic Acid ((R)-2-cyclopropyl-2-hydroxy-propyl)-amide The title compound was synthesized in analogy to the procedure described for the preparation of Example 36 using 5-bromo-3-(4-trifluoromethoxy-phenyl)-pyrazine-2-ylamine (prepared in analogy to example 40a), (R)-α-(aminomethyl)-α-methyl-cyclopropanemethanol and hydroxymethylcyclopropane as starting materials to give the title compound as colorless oil, MS (ISP): 452.0 (M+H)$^+$.

Example 110

Preparation of 6-Cyclopropylmethoxy-5-(4-fluoro-phenyl)-N-(2-hydroxy-2-methyl-propyl)-nicotinamide The title compound was synthesized in analogy to Example 31, using 5-bromo-6-chloro-3-pyridinecarboxylic acid, hydroxymethyl-cyclopropan, 4-fluorophenylboronic acid and 1-amino-2-methyl-propan-2-ol hydrochloride as starting materials to yield 6-cyclopropylmethoxy-5-(4- fluoro-phenyl)-N-(2-hydroxy-2-methyl-propyl)-nicotinamide. MS (ISP) 359.1 (M+H)+.

Example 111

Preparation of 5-(5-Bromo-furan-2-ylethynyl)-6-(4-chloro-phenyl)-pyrazine-2-carboxylic Acid ((R)-2-cyclopropyl-2-hydroxy-propyl)-amide a) 6-(4-Chloro-phenyl)-5-triethylsilanylethynyl-pyrazine-2-carboxylic Acid ((R)-2-cyclopropyl-2-hydroxy-propyl)-amide A mixture of 7.0 mg bistriphenylphosphinpalladium dichloride and 4 mg copperiodide in 5 ml triethylamine was heated to reflux for 30 min. To the resulting solution was added 0.41 g 5-bromo-6-(4-chloro-phenyl)-pyrazine-2-carboxylic acid ((R)-2-cyclopropyl-2-hydroxy-propyl)-amide (example 62a) and 0.28 g triethylsilane and the mixture was refluxed for 0.5 h. The reaction mixture was cooled to room temperature and partitioned between 10% citric acid and ethyl acetate. The organic phase was purified by chromatography on silica gel with heptane:ethyl acetate=1:1 to yield 0.45 g of 6-(4-chloro-phenyl)-5-triethylsilanylethynyl-pyrazine-2-carboxylic acid ((R)-2-cyclopropyl-2-hydroxy-propyl)-amide as a solidifying foam.

b) 6-(4-Chloro-phenyl)-5-ethynyl-pyrazine-2-carboxylic Acid ((R)-2-cyclopropyl-2-hydroxy-propyl)-amide To a solution of 0.40 g 6-(4-chloro-phenyl)-5-triethylsilanylethynyl-pyrazine-2-carboxylic acid ((R)-2-cyclopropyl-2-hydroxy-propyl)-amide in 10 ml methanol was added at room temperature 0.40 g ammonium fluoride and the mixture was stirred at room temperature for 30 min. The orange reaction mixture was partitioned between water and ethyl aceate, the phases were separated and the organic phase was purified by chromatography on silica gel with heptane:ethyl acetate=1:1 to yield 6-(4-chloro-phenyl)-5-ethynyl-pyrazine-2-carboxylic acid ((R)-2-cyclopropyl-2-hydroxy-propyl)-amide as light yellow foam.

c) 5-(5-Bromo-furan-2-ylethynyl)-6-(4-chloro-phenyl)-pyrazine-2-carboxylic Acid ((R)-2-cyclopropyl-2-hydroxy-propyl)-amide A mixture of 7.0 mg bistriphenylphosphinpalladium dichloride and 0.004 g copperiodide in 3 ml triethylamine was heated to reflux for 0.5 h The reaction was cooled to room temperature and 0.100 g 6-(4-chloro-phenyl)-5-ethynyl-pyrazine-2-carboxylic acid ((R)-2-cyclopropyl-2-hydroxy-propyl)-amide and 0.20 g 2-5-dibromofuran was added and the mixture was stirred at room temperature for 15 min (no reaction by tlc) and then refluxed for 30 min. The reaction mixture was cooled to room temperature and partitioned between 10% citric acid and ethyl aceate. The phases were separated and the organic phase was purified by chromatography on silica gel with heptane:ethyl acetate.=1:1 to yield the title compound as orange gum, MS (ISP) 502.0 (M+H)+.

Example 112

Preparation of 5-(4-Chloro-phenyl)-N-((1R,2R)-2-hydroxy-cyclohexyl)-6-(3-methoxy-prop-1-ynyl)-nicotinamide a) 6-Chloro-5-(4-chloro-phenyl)-N-((1R,2R)-2-hydroxy-cyclohexyl)-nicotinamide The title compound was synthesized in analogy to Example 5 d from 6-chloro-5-(4-chloro-phenyl)-nicotinic acid (Example 5b) and (1R,2R)-2-amino-1-cyclohexanol to yield 6-chloro-5-(4-chloro-phenyl)-N-((1R,2R)-2-hydroxy-cyclohexyl)-nicotinamide as a colorless solid, MS (ISP) 364.9, 366.9 (M+H)+.

b) 5-(4-Chloro-phenyl)-N-((1R,2R)-2-hydroxy-cyclohexyl)-6-(3-methoxy-prop-1-ynyl)-nicotinamide To a mixture of 6-chloro-5-(4-chloro-phenyl)-N-((1R,2R)-2-hydroxy-cyclohexyl)-nicotinamide (450 mg), 52 mg bistriphenylphosphinpalladium dichloride, 14 mg copperiodide, 146 mg triphenylphosphine and methyl propargyl ether (0.12 mL) in 10 mL DMF is added diethylamine (1.9 μL). The mixture is heated in the microwave oven for 40 min at 120° C. The reaction mixture was cooled to room temperature and partitioned between 1 N hydrochloric acid and ethyl acetate. The organic phase was purified by gradient chromatography on silica gel with heptane:ethyl acetate to yield 0.13 g of the title compound as a light yellow solid, MS (ISP) 399.1 (M+H)+.

Example 113

Preparation of 5-(4-Chloro-phenyl)-6-cyclopropylethynyl-N-((1R,2R)-2-hydroxy-cyclohexyl)-nicotinamide The title compound was synthesized in analogy to Example 112, using 6-chloro-5-(4-chloro-phenyl)-N-((1R,2R)-2-hydroxy-cyclohexyl)-nicotinamide and ethynylcyclopropane as starting materials to yield the product as an off-white solid, MS (ISP) 395.3, 397.2 (M+H)+.

Example 114

Preparation of 5-(4-Chloro-phenyl)-6-cyclopropylmethoxy-N-((1R,2R)-2-hydroxy-cyclohexyl)-2-methyl-nicotinamide a) 5-Bromo-6-cyclopropylmethoxy-2-methyl-nicotinic Acid Ethyl Ester A mixture of 5-bromo-6-chloro-2-methyl-3-pyridinecarboxylic acid ethyl ester (CAN 41598-77-0) (0.7 g, 2.5 mmol), hydroxymethylcyclopropane (0.57 mL, 6.2 mmol) and DBU (0.94 mL) was heated for 15 min in a microwave oven to 100° C. The reaction mixture was cooled to room temperature and partitioned between 10% citric acid and ethyl acetate. The phases were separated and the organic phase was purified by chromatography on silica gel with a cyclohexane:ethyl acetate gradient to yield the title compound as light yellow solid, MS (ISP) 314.0, 316.0 (M+H)+.

b) 5-Bromo-6-cyclopropylmethoxy-2-methyl-nicotinic Acid

Sodium hydroxide solution (1 N, 3.6 mL) was added to a solution of 5-bromo-6-cyclopropylmethoxy-2-methyl-nicotinic acid ethyl ester (0.58 g, 1.8 mmol) in THF (5.3 mL). The mixture was heated for 5 h to 70° C., cooled and neutralized with hydrochloric acid (1 N, 1.8 mL). After addition of citric acid the product precipitated and was purified by chromatography on silica gel with a dichloromethane:methanol gradient to yield the title compound as colorless solid, MS (ISP) 284.1 (M–H)+.

c) 5-Bromo-6-cyclopropylmethoxy-N-((1R,2R)-2-hydroxy-cyclohexyl)-2-methyl-nicotinamide The title compound was synthesized in analogy to the procedure described for the preparation of Example 31b, using 5-bromo-6-cyclopropylmethoxy-2-methyl-nicotinic acid and (1R,2R)-2-amino-1-cyclohexanol as starting materials, MS (ISP): 383.1, 385.1 (M+H)+.

d) 5-(4-Chloro-phenyl)-6-cyclopropylmethoxy-N-((1R,2R)-2-hydroxy-cyclohexyl)-2-methyl-nicotinamide The title compound was synthesized in analogy to the procedure described for the preparation of Example 31c, using 5-bromo-6-cyclopropylmethoxy-N-((1R,2R)-2-hydroxy-cyclohexyl)-2-methyl-nicotinamide and 5-chlorophenyl-boronic acid as starting materials, MS (ISP): 415.3 (M+H)+.

Example 115

Preparation of 5-(4-Chloro-phenyl)-N-((1R,2R)-2-hydroxy-cyclohexyl)-6-(5-methyl-isoxazol-3-yl-methoxy)-nicotinamide The title compound was synthesized in analogy to Example 31, using 5-bromo-6-chloro-3-pyridinecarboxylic acid, 5-methyl-3-isoxazolemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(5-methyl-isoxazol-3-ylmethoxy)-nicotinamide, MS (ISP) 442.1 (M+H)+.

Example 116

Preparation of N—((R)-2-Cyclopropyl-2-hydroxy-propyl)-5-(4-fluoro-phenyl)-6-(pyridin-2-yl-methoxy)-nicotinamide The title compound was synthesized in analogy to Example 31, using 5-bromo-6-chloro-3-pyridinecarboxylic acid, 2-pyridinemethanol, (4-fluoro-phenyl)-boronic acid and (R)-α-(aminomethyl)-α-methyl-cyclopropanemethanol as starting materials to yield N—((R)-2-cyclopropyl-2-hydroxy-propyl)-5-(4-fluoro-phenyl)-6-(pyridin-2-yl-methoxy)-nicotinamide, MS (ISP) 422.0 (M+H)+.

Example 117

Preparation of 5-(2-Pyridin-3-yl-ethyl)-6-(4-trifluoromethoxy-phenyl)-pyrazine-2-carboxylic Acid ((R)-2-cyclopropyl-2-hydroxy-propyl)-amide To a solution of 0.1 g 5-bromo-6-(4-trifluoromethoxy-phenyl)-pyrazine-2-carboxylic acid ((R)-2-cyclopropyl-2-hydroxy-propyl)-amide in 2.0 ml of TEA is added at room temperature 0.015 g of bis(triphenylphosphine) palladium(II) chloride, 0.002 g cuprous iodide and 0.034 g meta-ethynylpyridine. The mixture is treated at 100° C., 1½ hours at the microwave. The starting material is consumed, as evidenced by HPLC. To the mixture is 1N HCl solution in water and ethyl acetate. The organic layer is washed with sodium bicarbonate and sodium chloride 10% solution in water. The residue is purified by chromatography in silica gel. The intermediate was hydrogenated under a hydrogen atmosphere in the presence of palladium on charcoal to yield after filtration and evaporation of the solvent the title compound as off-white oil, MS (ISP) 487.3 (M+H)+.

Example 118

Preparation of 5-(4-Chloro-phenyl)-N-((1R,2R)-2-hydroxy-cyclohexyl)-2-methyl-6-(2,2,2-trifluoroethoxy)-nicotinamide The title compound was synthesized in analogy to Example 114, using 5-bromo-6-chloro-2-methyl-3-pyridinecarboxylic acid ethyl ester, 2,2,2-trifluoroethanol, ((1R,2R)-2-amino-1-cyclohexanol and (4-chloro-phenyl)-boronic acid as starting materials to yield the product as off-white solid, MS (ISP) 443.4 (M+H)+.

Example 119

Preparation of 6-(4-Chloro-phenyl)-5-thiomorpholin-4-yl-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and thiomorpholine as starting materials to give the title compound as a light yellow foam, MS (ISP): 415.3 (M+H–(H$_2$O))+.

Example 120

Preparation of 6-(4-Chloro-phenyl)-5-(4,4-difluoropiperidin-1-yl)-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-chloro-phenyl)-pyrazine-2-carboxylic acid ((R-2-cyclopropyl-2-hydroxy-propyl)-amide and 4,4-difluoropiperidine hydrochloride as starting materials to give the title compound as white solid, MS (ISP): 451.1 (M+H)+.

Example 121

Preparation of 6-(4-Chloro-phenyl)-5-(2-cyclopropyl-ethyl)-pyrazine-2-carboxylic Acid ((R)-2-cyclopropyl-2-hydroxy-propyl)-amide The title compound was synthesized in analogy to Example 117, using 5-bromo-6-(4-chloro-phenyl)-pyrazine-2-carboxylic acid ((R)-2-cyclopropyl-2-hydroxy-propyl)-amide and ethynylcyclopropane as starting materials to yield the product as colorless foam, MS (ISP) 400.1 $(M+H)^+$.

Example 122

Preparation of 5-(2-Pyridin-2-yl-ethyl)-6-(4-trifluoromethoxy-phenyl)-pyrazine-2-carboxylic Acid ((R)-2-cyclopropyl-2-hydroxy-propyl)-amide The title compound was synthesized in analogy to Example 117, using 5-bromo-6-(4-trifluoromethoxy-phenyl)-pyrazine-2-carboxylic acid ((R)-2-cyclopropyl-2-hydroxy-propyl)-amide and ortho-ethynylpyridine as starting materials to yield the product as light brown oil, MS (ISP) 487.4 $(M+H)^+$.

Example 123

Preparation of (RS)-6-Cyclopropylmethoxy-N-(3,3,3-trifluoro-2-hydroxy-2-methyl-propyl)-5-(4-trifluoromethyl-phenyl)-nicotinamide The title compound was synthesized in analogy to Example 31, using 5-bromo-6-chloro-3-pyridinecarboxylic acid, hydroxymethylcyclopropan, 4-trifluoromethyl-phenylboronic acid and 3-amino-1,1,1-trifluoro-2-methyl-propan-2-ol (CAN [354-68-7]) as starting materials to yield (RS)-6-cyclopropylmethoxy-N-(3,3,3-trifluoro-2-hydroxy-2-methyl-propyl)-5-(4-trifluoromethyl-phenyl)-nicotinamide as off-white solid, MS (ISP) 463.0 $(M+H)^+$.

Example 124

Preparation of (RS)-6-Cyclopropylmethoxy-N-(3,3,3-trifluoro-2-hydroxy-2-methyl-propyl)-5-(4-trifluoromethoxy-phenyl)-nicotinamide The title compound was synthesized in analogy to Example 31, using 5-bromo-6-chloro-3-pyridinecarboxylic acid, hydroxymethylcyclopropane, 4-trifluoromethoxy-phenylboronic acid and 3-amino-1,1,1-trifluoro-2-methyl-propan-2-ol (CAN [354-68-7]) as starting materials to yield (RS)-6-cyclopropylmethoxy-N-(3,3,3-trifluoro-2-hydroxy-2-methyl-propyl)-5-(4-trifluoromethoxy-phenyl)-nicotinamide as light brown solid, MS (ISP) 479.0 $(M+H)^+$.

Example 125

Preparation of 5-(4-Fluoro-phenyl)-N-((1R,2R)-2-hydroxy-cyclohexyl)-6-(3-methyl-pyridin-2-ylmethoxy)-nicotinamide The title compound was synthesized in analogy to Example 31, using 5-bromo-6-chloro-3-pyridinecarboxylic acid, (3-methyl-pyridin-2-yl)-methanol, (4-fluoro-phenyl)-boronic acid and ((1R,2R)-2-amino-1-cyclohexanol as starting materials to yield 5-(4-fluoro-phenyl)-N-((1R,2R)-2-hydroxy-cyclohexyl)-6-(3-methyl-pyridin-2-ylmethoxy)-nicotinamide, MS (ISP) 436.2 $(M+H)^+$.

Example 126

Preparation of 5-(4-Chloro-phenyl)-N-((1R,2R)-2-hydroxy-cyclohexyl)-6-(pyridin-2-ylmethoxy)-nicotinamide The title compound was synthesized in analogy to Example 31, using 5-bromo-6-chloro-3-pyridinecarboxylic acid, 2-pyridinemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(pyridin-2-ylmethoxy)-nicotinamide, MS (ISP) 440.2 $(M+H)^+$.

Example 127

Preparation of 6-(4-Fluoro-phenyl)-5-piperidin-1-yl-pyrazine-2-carboxylic Acid ((R)-2-cyclopropyl-2-hydroxy-propyl)-amide The title compound was synthesized in analogy to the procedure described for the preparation of Example 62 using 5-bromo-6-(4-fluoro-phenyl)-pyrazine-2-carboxylic acid ((R-2-cyclopropyl-2-hydroxy-propyl)-amide and piperidine as starting materials to give the title compound as white solid, MS (ISP): 421.1 $(M+H)^+$.

Example 128

Preparation of 5-(4-Chloro-phenyl)-N-((1R,2R)-2-hydroxy-cyclohexyl)-6-[2-(1-hydroxy-cyclopentyl)-ethyl]-nicotinamide a) 5-(4-Chloro-phenyl)-N-((1R,2R)-2-hydroxy-cyclohexyl)-6-(1-hydroxy-cyclopentylethynyl)-nicotinamide The title compound was synthesized in analogy to Example 112, using 6-chloro-5-(4-chloro-phenyl)-N-((1R,2R)-2-hydroxy-cyclohexyl)-nicotinamide and 1-ethynylcyclopentanol as starting materials to yield the product as colorless solid, MS (ISP) 439.1, 441.2 $(M+H)^+$.

b) 5-(4-Chloro-phenyl)-N-((1R,2R)-2-hydroxy-cyclohexyl)-6-[2-(1-hydroxy-cyclopentyl)-ethyl]-nicotinamide 5-(4-Chloro-phenyl)-N-((1R,2R)-2-hydroxy-cyclohexyl)-6-(1-hydroxy-cyclopentylethynyl)-nicotinamide (120 mg, 0.27 mmol) was dissolved in ethylacetate (15 mL) and hydrogenated in the presence of palladium on charcoal (10%) at room temperature and atmospheric pressure. After filtration and evaporation of the solvent the residue was purified by chromatography on silica gel with a ethyl acetate:methanol gradient to yield the product as colorless foam, MS (ISP) 443.1, 445.1 $(M+H)^+$.

Example 129

Preparation of 5-(4-Cyano-phenyl)-6-cyclopropyl-methoxy-N-((1R,2R)-2-hydroxy-cyclohexyl)-nicotinamide The title compound was synthesized in analogy to Example 31, using 5-bromo-6-chloro-3-pyridinecarboxylic acid, 4-pyridinemethanol, (4-cyano-phenyl)-boronic acid and (1R,2R)-2-amino-1-cyclohexanol as starting materials to yield 5-(4-cyano-phenyl)-6-cyclopropylmethoxy-N-((1R,2R)-2-hydroxy-cyclohexyl)-nicotinamide, MS (ISP) 392.2 $(M+H)^+$.

Example 130

Preparation of 6-Cyclopropylmethoxy-5-(4-fluoro-phenyl)-N—((R)-3,3,3-trifluoro-2-hydroxy-2-methyl-propyl)-nicotinamide The title compound was synthesized in analogy to Example 31, using 5-bromo-6-chloro-3-pyridinecarboxylic acid, hydroxymethylcyclopropan, 4-fluorophenylboronic acid and 3-amino-1,1,1-trifluoro-2-methyl-propan-2-ol (CAN [354-68-7]) as starting materials to yield (RS)-6-cyclopropylmethoxy-N-(3,3,3-trifluoro-2-hydroxy-2-methyl-propyl)-5-(4-fluoro-phenyl)-nicotinamide. The two enantiomers were separated by column chromatography on chiral phase. White solid, MS (ISP) 413.1 $(M+H)^+$.

Example 131

Preparation of 5-(4-Chloro-phenyl)-6-cyclopropyl-methoxy-N-((1R,2R)-2-hydroxy-cyclohexyl)-2-trifluoromethyl-nicotinamide a) 5-Bromo-6-cyclopropylmethoxy-2-trifluoromethyl-nicotinic Acid Ethyl Ester 5-Bromo-1,6-dihydro-6-oxo-2-(trifluoromethyl)-3-pyridinecarboxylic acid ethyl ester (CAN 862111-61-3) (1.3 g, 3.6 mmol) was dissolved in THF (15 mL). To the solution were added hydroxymethylcyclopropane (0.35 mL, 4.3 mmol), triphenylphosphine (1.1 g, 4.3 mmol) and diethyl azodicarboxylate (0.69 mL, 4.3 mmol) at 0° C. The mixture was stirred for 30 min at 0° C. and for 16 h at room temperature. The solvent was removed in vacuo and the residue was purified by chromatography on silica gel with dichloromethane:methanol 4:1 to yield the product as yellowish oil, MS (ISP) 368.0, 370.0 $(M+H)^+$.

b) 5-(4-Chloro-phenyl)-6-cyclopropylmethoxy-2-trifluoromethyl-nicotinic Acid Ethyl Ester 5-Bromo-6-cyclopropylmethoxy-2-trifluoromethyl-nicotinic acid ethyl ester (0.3 g, 0.81 mmol) was dissolved in dioxane (1.6 mL). To this solution was added with stirring [1,1'-bis(diphenylphosphino)ferrocene]dichloropalladium(II) $CH_2Cl_2$ (33 mg, 0.04 mmol), 4-chlorophenylboronic acid (197 mg, 1.2 mmol) and sodium carbonate solution (2M, 1.2 mL). This mixture was heated to 80° C. for 5 h and cooled to room temperature. Water (150 mL) was added, the phases were separated and the water mixture was extracted with ethylacetate. Organic phases were pooled, dried with $MgSO_4$ and the volatiles removed in vacuo. The residue was purified by flash chromatography on silica (dichloromethane/methanol, 4:1) to give the title compound (0.37 g) as light yellow oil; MS (ISP) 400.1 $(M+H)^+$.

c) 5-(4-Chloro-phenyl)-6-cyclopropylmethoxy-2-trifluoromethyl-nicotinic Acid The title compound was synthesized in analogy to Example 5c, using 5-(4-chloro-phenyl)-6-cyclopropyl-methoxy-2-trifluoromethyl-nicotinic acid ethyl ester as starting material, MS (ISP) 370.0 $(M-H)^+$.

d) 5-(4-Chloro-phenyl)-6-cyclopropylmethoxy-N-((1R,2R)-2-hydroxy-cyclohexyl)-2-trifluoromethyl-nicotinamide The title compound was synthesized in analogy to Example 5d, using 5-(4-Chloro-phenyl)-6-cyclopropyl-methoxy-2-trifluoromethyl-nicotinic acid and (1R,2R)-2-amino-1-cyclohexanol as starting materials, MS (ISP) 469.3 $(M+H)^+$.

Example 132

Preparation of N—((S)-1-Hydroxymethyl-3-methyl-butyl)-5-(3-methoxy-phenyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 3-methoxyphenyl-boronic acid (commercially available) and (S)-(+)-leucinol (commercially available) as starting materials. MS (ISP): 398.3 $(M+H^+)$.

Example 133

Preparation of N—((S)-1-Hydroxymethyl-3-methyl-butyl)-5-(4-methoxy-phenyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-methoxyphenyl-boronic acid (commercially available) and (S)-(+)-leucinol (commercially available) as starting materials. MS (ISP): 398.2 $(M+H^+)$.

Example 134

Preparation of 5-(4-Chloro-3-methyl-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 3-chloro-4-methylphenyl-boronic acid (commercially available) and (R)-(−)-leucinol (commercially available) as starting materials. MS (ISP): 416.4 $(M+H^+)$.

Example 135

Preparation of N—((R)-1-Hydroxymethyl-3-methyl-butyl)-5-(3-methoxy-phenyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 3-methoxyphenyl-boronic acid

Example 136

Preparation of N—((R)-1-Hydroxymethyl-3-methyl-butyl)-5-(4-methoxy-phenyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-methoxyphenyl-boronic acid (commercially available) and (R)-(−)-leucinol (commercially available) as starting materials. MS (ISP): 398.2 (M+H$^+$).

Example 137

Preparation of N—((R)-1-Hydroxymethyl-3-methyl-butyl)-6-pyrrolidin-1-yl-5-(4-trifluoromethyl-phenyl)-nicotinamide The title compound was synthesized in analogy to the procedure described for the preparation of Example 43, using 5-bromo-6-chloro-nicotinic acid methyl ester, pyrrolidine (commercially available), 4-trifluoromethylphenyl-boronic acid (commercially available) and (R)-(−)-leucinol (commercially available) as starting materials. MS (ISP): 436.4 (M+H$^+$).

Example 138

Preparation of N—((R)-1-Hydroxymethyl-3-methyl-butyl)-6-pyrrolidin-1-yl-5-(4-trifluoromethoxy-phenyl)-nicotinamide The title compound was synthesized in analogy to the procedure described for the preparation of Example 43, using 5-bromo-6-chloro-nicotinic acid methyl ester, pyrrolidine (commercially available), 4-trifluoromethoxyphenyl-boronic acid (commercially available) and (R)-(−)-leucinol (commercially available) as starting materials. MS (ISP): 452.3 (M+H$^+$).

Example 139

Preparation of 5-(4-Cyano-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-cyanophenyl-boronic acid (commercially available) and (R)-(−)-leucinol (commercially available) as starting materials. MS (ISP): 393.4 (M+H$^+$).

Example 140

Preparation of 5-(4-Chloro-phenyl)-N-((1R,2R)-2-hydroxy-cyclohexyl)-6-(2-pyridin-2-yl-ethyl)-nicotinamide a) 5-(4-Chloro-phenyl)-6-pyridin-2-ylethynyl-Nicotinic Acid Methyl Ester A degassed solution of 2-ethynyl-pyridine (2.0 mmol, CAN 1945-84-2) in tetrahydrofuran and N-ethyldiisopropylamine (1:1, 10 ml) was added to a degassed suspension of 6-chloro-5-(4-chloro-phenyl)-nicotinic acid methyl ester (1.0 mmol), [1,1'-bis(diphenylphosphino)-ferrocene]palladium (II) dichloride dichloromethane complex (1:1) (49 mg, 0.06 mmol), polymer supported triphenylphoshine (135 mg, 1.48 mmol/g, 0.2 mmol) and copper(I)iodide (11 mg, 0.06 mmol) in tetrahydrofuran and N-ethyldiisopropylamine (1:1, 5 ml). The reaction mixture was heated at 120° C. for 20 hours under an atmosphere of nitrogen. The reaction mixture was cooled to room temperature and the solids were removed by filtration. The solids were washed with ethyl acetate (100 ml), the organic liquors were combined and washed with saturated aqueous ammonium chloride solution (3×50 ml). The organic layer was then dried over MgSO$_4$ and concentrated in vacuo. Purification by flash column chromatography (20% ethyl acetate/heptane) gave the title compound as brown oil.

b) 5-(4-Chloro-phenyl)-6-(2-pyridin-2-yl-ethyl)-Nicotinic Acid Methyl Ester

Palladium on carbon (10% w/w, 30 mg) was added to a solution of 5-(4-Chloro-phenyl)-6-pyridin-2-ylethynyl-nicotinic acid methyl ester (0.83 mmol) in ethanol (10 ml). The reaction mixture was stirred at room temperature under an atmosphere of hydrogen for 20 hours. The reaction vessel was purged with nitrogen and catalyst was removed by filtration. The reaction mixture was concentrated in vacuo to give 5-(4-Chloro-phenyl)-6-(2-pyridin-2-yl-ethyl)-nicotinic acid methyl ester (59% yield).

c) 5-(4-Chloro-phenyl)-6-(2-pyridin-2-yl-ethyl)-nicotinic Acid

Aqueous 1M lithium hydroxide solution (2.25 ml, 2.25 mmol) was added to a solution of 65-(4-Chloro-phenyl)-6-(2-pyridin-2-yl-ethyl)-nicotinic acid methyl ester (0.49 mmol) in tetrahydrofuran and methanol (6:1, 7 ml). The reaction mixture was stirred for 20 hours at room temperature then concentrated in vacuo. The residue was treated with 4M HCl in dioxane (0.56 ml, 2.25 mmol) and concentrated in vacuo to give crude 5-(4-Chloro-phenyl)-6-(2-pyridin-2-yl-ethyl)-nicotinic acid. This material was used in the subsequent amide coupling step without further purification.

d) 5-(4-Chloro-phenyl)-N-((1R,2R)-2-hydroxy-cyclohexyl)-6-(2-pyridin-2-yl-ethyl)-nicotinamide The title compound was synthesized in analogy to Example 5d, using 5-(4-chloro-phenyl)-6-(2-pyridin-2-yl-ethyl)-nicotinic acid and (1R,2R)-2-amino-cyclohexanol as starting materials, LC at 215 nm; Rt 3.10: 98%, m/z (ES$^+$): 436.4 (M+H).

Example 141

Preparation of N-((1R,2R)-2-Hydroxy-cyclohexyl)-6-[2-(3-methyl-3H-imidazol-4-yl)-ethyl]-5-(4-trifluoromethyl-phenyl)-nicotinamide The title compound was synthesized in analogy to the procedure described for the preparation of Example 140, using 5-ethynyl-1-methyl-1H-imidazole (CAN 71759-92-7), 6-chloro-5-(4-trifluoromethyl-phenyl)-nicotinic acid methyl ester, and (1R,2R)-2-amino-cyclohexanol (commercially available) as starting materials, LC at 215 nm; Rt 3.11: 100%, m/z (ES$^+$): 473.5 (M+H).

Example 142

Preparation of 5-(4-Chloro-phenyl)-6-[2-(5-fluoro-pyridin-2-yl)-ethyl]-N-((1R,2R)-2-hydroxy-cyclohexyl)-nicotinamide The title compound was synthesized in analogy to the procedure described for the preparation of Example 140, using 2-ethynyl-5-fluoro-pyridine (CAN 884494-34-2), 6-chloro-5-(4-chloro-phenyl)-nicotinic acid methyl ester, and (1R,2R)-2-amino-cyclohexanol (commercially available) as starting materials, LC at 215 nm; Rt 4.12: 99%, m/z (ES$^+$): 454.5 (M+H).

Example 143

Preparation of 6-[2-(5-Fluoro-pyridin-2-yl)-ethyl]-N-((1R,2R)-2-hydroxy-cyclohexyl)-5-(4-trifluoromethyl-phenyl)-nicotinamide The title compound was synthesized in analogy to the procedure described for the preparation of Example 140, using 2-ethynyl-5-fluoro-pyridine (CAN 884494-34-2), 6-chloro-5-(4-trifluoromethyl-phenyl)-nicotinic acid methyl ester, and (1R,2R)-2-amino-cyclohexanol (commercially available) as starting materials, LC at 215 nm; Rt 4.26: 95%, m/z (ES$^+$): 488.5 (M+H).

Example 144

Preparation of 5-(4-Chloro-phenyl)-N—((R)-2-cyclopropyl-2-hydroxy-propyl)-6-(2-pyridin-2-yl-ethyl)-nicotinamide The title compound was synthesized in analogy to the procedure described for the preparation of Example 140, using 2-ethynyl-pyridine (CAN 1945-84-2), 6-chloro-5-(4-chloro-phenyl)-nicotinic acid methyl ester, and (R)-α-(aminomethyl)-α-methyl-cyclopropanemethanol as starting materials, LC at 215 nm; Rt 3.16: 88%, m/z (ES$^+$): 436.4 (M+H).

Example 145

Preparation N—((R)-2-Cyclopropyl-2-hydroxy-propyl)-6-(2-pyridin-2-yl-ethyl)-5-(4-trifluoromethyl-phenyl)-nicotinamide The title compound was synthesized in analogy to the procedure described for the preparation of Example 140, using 2-ethynyl-pyridine (CAN 1945-84-2), 6-chloro-5-(4-trifluoromethyl-phenyl)-nicotinic acid methyl ester, and (R)-α-(aminomethyl)-α-methyl-cyclopropanemethanol as starting materials, LC at 215 nm; Rt 3.30: 98%, m/z (ES$^+$): 470.5 (M+H).

Example 146

Preparation of 2-[{6-(4-Fluoro-phenyl)-5-piperidin-1-yl-pyrazine-2-carbonyl]-amino}-2-methyl-propionic Acid Methyl Ester a) 5-Bromo-3-(4-fluoro-phenyl)-pyrazin-2-ylamine

Tetrakis(triphenylphosphine) palladium (0) (1.12 g, 0.97 mmol, 0.05 eq) was added portion-wise to a solution of 2-amino-3,5-dibromopyrazine (5.01 g, 19.76 mmol, 1.0 eq) in 1,2-dimethoxyethane (100 ml) at room temperature and the reaction stirred for 0.5 hours. A solution of sodium carbonate (5.30 g, 50.5 mmol, 2.6 eq) in water (50 ml) was added portion-wise to the resulting mixture, followed by 4-fluorophenylboronic acid (3.08 g, 21.9 mmol, 1.1 eq). The mixture was heated to 100° C. for 5 h. The resulting yellow solution was partitioned between 10% aqueous citric acid (25 ml) and ethyl acetate (50 ml). The organic layer was washed with 10% aqueous sodium bicarbonate (25 ml), brine (25 ml), dried over magnesium sulfate and concentrated in vacuo. The residue was purified by chromatography on silica gel with a gradient of heptane to dichloromethane to afford 5-Bromo-3-(4-fluoro-phenyl)-pyrazin-2-ylamine as white crystals. Yield=3.22 g (60%). HPLC-MS=100%; 1.89 min (MW=268; M+1=270.1).

b) 5-Amino-6-(4-fluoro-phenyl)-pyrazine-2-carboxylic Acid Methyl Ester

To a methanol solution (35 ml) of 5-bromo-3-(4-fluoro-phenyl)-pyrazin-2-ylamine (1.87 g, 6.97 mmol, 1.0 eq) was added 15 ml ethyl acetate at room temperature. [1,1'-bis(diphenylphosphino) ferrocen]palladium(II)chloride 1:1 complex with dichloromethane (0.26 g, 0.32 mmol, 0.05 eq) was added portion-wise to the reaction mixture followed by triethylamine (1.95 ml, 13.5 mmol, 2.0 eq) and the solution was heated with stirring to 110° C. under 70 bar carbon monoxide for 18 hours. On cooling and removal of carbon monoxide, the reaction mixture was concentrated in vacuo and the residue purified by chromatography on silica gel with heptane:ethyl acetate (1:1) to afford 5-Amino-6-(4-fluoro-phenyl)-pyrazine-2-carboxylic acid methyl ester as white crystals. Yield=1.26 g (73%). $^1$H-NMR (400 MHz, DMSO): δ 3.80 (3H, s), 7.11 (2H, br s), 7.33 (2H, t, J=8.87 Hz), 7.67-7.70 (2H, m), 8.56 (1H, s). HPLC-MS=100%; 1.49 min (MW=247; M+1=248.3).

c) 5-Bromo-6-(4-fluoro-phenyl)-pyrazine-2-carboxylic Acid Methyl Ester

To a suspension of 5-amino-6-(4-fluoro-phenyl)-pyrazine-2-carboxylic acid methyl ester (1.26 g, 5.10 mmol, 1.0 eq) in dibromomethane (25 ml) was added isoamyl nitrite (0.85 ml, 6.29 mmol, 1.2 eq) at room temperature. The resulting suspension was added over 30 minutes at room temperature to a dibromomethane (5 ml) solution of trimethylbromosilane (0.82 ml, 5.90 mmol, 1.15 eq). The mixture was stirred for 2 hours at room temperature after which time the turbid solution was added to aqueous sodium bicarbonate (10%, 15 ml). The phases were mixed, separated and the organic layer dried over magnesium sulfate, concentrated in vacuo and purified by chromatography on silica gel using a gradient of heptane to 10% ethyl acetate in heptane to afford 5-Bromo-6-(4-fluoro-phenyl)-pyrazine-2-carboxylic acid methyl ester as white crystals. Yield=0.81 g (51%). $^1$H NMR (250 MHz, DMSO): δ 3.92 (3H, s), 7.38 (2H, t, J=8.98 Hz), 7.76-7.81 (2H, m), 8.98 (1H, s). HPLC-MS=100%; 2.13 min (MW=311; M+1=313.0).

d) 6-(4-Fluoro-phenyl)-5-piperidin-1-yl-pyrazine-2-carboxylic Acid Methyl Ester Piperidine (0.48 ml, 4.82 mmol, 2.0 eq) was added portion-wise to a acetonitrile (2 ml) solution of 5-Bromo-6-(4-fluoro-phenyl)-pyrazine-2-carboxylic acid methyl ester (0.75 g, 2.41 mmol, 1.0 eq) at room temperature. The mixture was irradiated at 100° C. in a microwave with stirring for 30 minutes.

HPLC-MS indicated complete consumption of starting material. The crude mixture was cooled to room temperature concentrated. The residue was re-dissolved in ethyl acetate (10 ml), washed with water (5 ml) and the organic phase dried over MgSO$_4$. Following filtration and evaporation in vacuo, the residue was purified by chromatography on silica gel using a gradient of heptane to 10% ethyl acetate in heptane to afford 6-(4-fluoro-phenyl)-5-piperidin-1-yl-pyrazine-2-carboxylic acid methyl ester. Yield=0.48 g (63%). $^1$H NMR (250 MHz, CDCl$_3$): δ 1.42-1.53 (6H, m), 3.20-3.24 (4H, m), 3.88 (3H, s), 7.06 (2H, t, J=8.78 Hz), 7.74-7.80 (2H, m), 8.68 (1H, s).

e) 6-(4-Fluoro-phenyl)-5-piperidin-1-yl-pyrazine-2-carboxylic Acid

To a tetrahydrofuran (5 ml) solution of 6-(4-Fluoro-phenyl)-5-piperidin-1-yl-pyrazine-2-carboxylic acid methyl ester (0.48 g, 1.52 mmol, 1.0 eq) was added a solution of lithium hydroxide (1M, 1.52 ml, 1.52 mmol, 1.0 eq) in water. The mixture was stirred overnight at room temperature after which time the resulting solution was acidified with hydrochloric acid (pH~5) and aqueous phase extracted with ethyl acetate (2×10 ml). The organic phase was dried over magnesium sulfate and concentrated in vacuo to afford 6-(4-fluoro-phenyl)-5-piperidin-1-yl-pyrazine-2-carboxylic acid as white crystals. Yield=0.42 g (91%). $^1$H NMR (400 MHz, DMSO): δ 1.46-1.53 (6H, m), 3.22-3.25 (4H, m), 7.32 (2H, t, J=8.87 Hz), 7.82-7.86 (2H, m), 8.62 (1H, s).

f) 2-{[6-(4-Fluoro-phenyl)-5-piperidin-1-yl-pyrazine-2-carbonyl]-amino}-2-methyl-propionic Acid Methyl Ester To a dichloromethane (1 ml) solution of 6-(4-Fluoro-phenyl)-5-piperidin-1-yl-pyrazine-2-carboxylic acid (0.107 g, 0.358 mmol, 1.0 eq) was added oxalyl chloride (0.136 g, 1.07 mmol, 3.0 eq). The reaction was stirred at room temperature for 3 hours after which time the solvent was removed in vacuo. The residue was re-dissolved in dichloromethane (3 ml) and added portion-wise to a dichloromethane (1 ml) solution of aminoisobutyric acid methyl ester (0.066 g, 0.429 mmol, 1.2 eq). PS-N,N-diisopropyl-ethylamine (0.31 g, 1.04 mmol, 3.0 eq) resin was added to the reaction and the mixture stirred overnight at room temperature. PS-isocyanate (0.15 g, 0.358 mmol, 1.0 eq) and PS-aminomethyl (0.15 g, 0.358 mmol, 1.0 eq) resin were added to the reaction and the mixture stirred for a further 12 hrs at room temperature. The reaction was filtered and resin washed successfully with dichloromethane (2×3 ml). The combined filtrates were concentrated in vacuo and the residue purified by chromatography on silica gel with heptane:ethyl acetate (1:1) to afford 2-{[6-(4-fluoro-phenyl)-5-piperidin-1-yl-pyrazine-2-carbonyl]-amino}-2-methyl-propionic acid methyl ester. Yield=0.030 g (21%). HPLC-MS 100%; 2.52 min (MW=400; M+1=401.2).

Example 147

Preparation of (R)-2-{[6-(4-Fluoro-phenyl)-5-pyrrolidin-1-yl-pyrazine-2-carbonyl]-amino}-3-methyl-butyric Acid Methyl Ester The title compound was synthesized in analogy to the procedure described for the preparation of Example 146, using 5-bromo-6-(4-fluoro-phenyl)-pyrazine-2-carboxylic acid methyl ester, pyrrolidine and (R)-valine methyl ester as starting materials, LC at 215 nm; Rt 2.43: 100%, m/z (ES$^+$): 401.2 (M+H).

Example 148

Preparation of 6-(4-Butylcarbamoyl-butoxy)-5-(4-chloro-phenyl)-N-((1R,2R)-2-hydroxy-cyclohexyl)-nicotinamide a) 5-Bromo-6-(5-hydroxy-pentyloxy)-nicotinic Acid The title compound was synthesized in analogy to the procedure described for the preparation of Example 31a, using 5-bromo-6-chloro-nicotinic acid and 1,5-pentanediol as starting materials to give the product as brownish oil, MS (ISP): 302.3 (M−H$^+$).

b) 5-Bromo-N-((1R,2R)-2-hydroxy-cyclohexyl)-6-(5-hydroxy-pentyloxy)-nicotinamide The title compound was synthesized in analogy to the procedure described for the preparation of Example 31b, using 5-bromo-6-(5-hydroxy-pentyloxy)-nicotinic acid and (1R,2R)-2-amino-cyclohexanol as starting materials to give the product as white solid, MS (ISP): 403.4 (MH$^+$).

c) 5-(4-Chloro-phenyl)-N-((1R,2R)-2-hydroxy-cyclohexyl)-6-(5-hydroxy-pentyloxy)-nicotinamide The title compound was synthesized in analogy to the procedure described for the preparation of Example 31c, using 5-Bromo-N-((1R,2R)-2-hydroxy-cyclohexyl)-6-(5-hydroxy-pentyloxy)-nicotinamide and 4-chlorophenyl-boronic acid as starting materials to give the product as white solid, MS (ISP): 433.4, 435.4 (M+H$^+$).

d) 5-[3-(4-Chloro-phenyl)-5-((1R,2R)-2-hydroxy-cyclohexylcarbamoyl)-pyridin-2-yloxy]-pentanoic Acid 5-(4-Chloro-phenyl)-N-((1R,2R)-2-hydroxy-cyclohexyl)-6-(5-hydroxy-pentyloxy)-nicotinamide (0.23 g, 0.5 mmol) was dissolved in dichloromethane (15 mL). To the solution was added 2,2,6,6-tetramethyl-1-piperidinyloxy (1 mg), tetrabutylammoniumchlorid (1.5 mg), 5 mL of an aqueous solution of sodium bicarbonate (0.5 M) and potassium carbonate (0.05 M) and N-chlorosuccinimid (0.146 g, 1.1 mmol). The mixture was stirred for 72 h at room temperature and afterwards poured into citric acid (10%, 20 mL) and extracted with dichloromethane. Organic phases were pooled, dried with Na$_2$SO$_4$ and the solvent was evaporated. The residue (aldehyde contaminated with some starting alcohol) was redissolved in tert-butanol (5 mL). To the solution was added 2-methyl-butene solution (2 M in THF, 5 mL), sodium chlorite (210 mg), and sodium dihydrogenphosphate (0.345 g). The mixture was stirred for 72 h at room temperature and afterwards poured into citric acid (10%, 50 mL) and extracted with ethyl acetate. Organic phases were pooled, dried with MgSO$_4$ and the solvent was evaporated. The residue was purified by column chromatography on silica (dichloromethane/methanol gradient) to yield 0.062 g of the title compound as a white foam, MS (ISP) 445.2 (M−H)$^+$.

e) 6-(4-Butylcarbamoyl-butoxy)-5-(4-chloro-phenyl)-N-((1R,2R)-2-hydroxy-cyclohexyl)-nicotinamide 5-[3-(4-Chloro-phenyl)-5-((1R,2R)-2-hydroxy-cyclohexylcarbamoyl)-pyridin-2-yloxy]-pentanoic acid (20 mg) was dissolved in DMF (1 mL). To the solution was added TBTU (16 mg), N,N-diisopropylethyl amine (0.038 mL, 42) and (N)-butylamine (0.005 mL). The reaction mixture was stirred for 16 h at room temperature. The solvent was evaporated in vacuo and the residue was purified by column chromatography on silica (dichloromethane/methanol gradient) to yield 21 mg of the title compound as a white solid, MS (ISP) 502.1, 504.1 (M+H)$^+$.

Example 149

Preparation of 5-[4-(2-Butylcarbamoyl-ethyl)-phenyl]-6-cyclopropylmethoxy-N-((1R,2R)-2-hydroxy-cyclohexyl)-nicotinamide a) 3-{4-[2-Cyclopropylmethoxy-5-((1R,2R)-2-hydroxy-cyclohexylcarbamoyl)-pyridin-3-yl]-phenyl}-propionic Acid The title compound was synthesized in analogy to the procedure described for the preparation of Example 31c, using 5-bromo-6-cyclopropylmethoxy-N-((1R,2R)-2-hydroxy-cyclohexyl)-nicotinamide and 4-(2-carbethoxyethyl)benzene-boronic acid (commercially available) as starting materials to give the product as white solid, MS (ISP): 437.2 (M−H)$^+$.

b) 5-[4-(2-Butylcarbamoyl-ethyl)-phenyl]-6-cyclopropylmethoxy-N-((1R,2R)-2-hydroxy-cyclohexyl)-nicotinamide The title compound was synthesized in analogy to the procedure described for the preparation of Example 148e, using 3-{4-[2-Cyclopropylmethoxy-5-((1R,2R)-2-hydroxy-cyclohexylcarbamoyl)-pyridin-3-yl]-phenyl}-propionic acid and (N)-butylamine as starting materials to give the product as white foam, MS (ISP): 494.3 (M+H$^+$).

Example 150

Preparation of 5-(2,4-Dichloro-phenyl)-N-(2-hydroxy-ethyl)-6-propoxy-nicotinamide The title compound was synthesized in analogy to the procedure described for the preparation of Example 43, using 5-bromo-6-chloro-nicotinic acid methyl ester, n-propanol (commercially available), 2,4-dichlorophenylboronic acid (commercially available) and aminoethanol (commercially available) as starting materials. MS (ISP): 369.2, 371.2 (M+H$^+$).

Example 151

Preparation of 6-Cyclopentylmethoxy-5-(2,4-dichloro-phenyl)-N-(2-hydroxy-ethyl)-nicotinamide The title compound was synthesized in analogy to the procedure described for the preparation of Example 43, using 5-bromo-6-chloro-nicotinic acid methyl ester, hydroxymethylcyclopentanepropanol (commercially available), 2,4-dichlorophenylboronic acid (commercially available) and aminoethanol (commercially available) as starting materials. MS (ISP): 409.3, 411.3 (M+H$^+$).

Example 152

Preparation of 5-(4-Chloro-phenyl)-N—((S)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-chlorophenyl-boronic acid (commercially available) and (S)-(+)-leucinol (commercially available) as starting materials. MS (ISP): 402.3 (M+H$^+$).

Example 153

Preparation of 5-(3,4-Dichloro-phenyl)-N—((S)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 3,4-dichlorophenyl-boronic acid (commercially available) and (S)-(+)-leucinol (commercially available) as starting materials. MS (ISP): 436.3 (M+H$^+$).

Example 154

Preparation of 5-(4-Chloro-3-methyl-phenyl)-N—((S)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-chloro-3-methylphenyl-boronic acid (commercially available) and (S)-(+)-leucinol (commercially available) as starting materials. MS (ISP): 416.3 (M+H$^+$).

Example 155

Preparation of 5-(2-Fluoro-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 2-fluorophenyl-boronic acid (commercially available) and (R)-(−)-leucinol (commercially available) as starting materials. MS (ISP): 386.4 (M+H$^+$).

Example 156

Preparation of 5-(4-Fluoro-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-fluorophenyl-boronic acid (commercially available) and (R)-(−)-leucinol (commercially available) as starting materials. MS (ISP): 386.4 (M+H$^+$).

Example 157

Preparation of 5-(3-Chloro-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 3-chlorophenyl-boronic acid (commercially available) and (R)-(−)-leucinol (commercially available) as starting materials. MS (ISP): 402.4 (M+H$^+$).

Example 158

Preparation of 5-(4-Chloro-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 4-chlorophenyl-boronic acid (commercially available) and (R)-(−)-leucinol (commercially available) as starting materials. MS (ISP): 402.4 (M+H$^+$).

Example 159

Preparation of 5-(3,4-Dichloro-phenyl)-N—((R)-1-hydroxymethyl-3-methyl-butyl)-6-pyrrolidin-1-yl-nicotinamide The title compound was synthesized in analogy to the procedure described for the preparation of Example 43, using 5-bromo-6-chloro-nicotinic acid methyl ester, pyrrolidine (commercially available), 3,4-dichlorophenyl-boronic acid (commercially available) and (R)-(−)-leucinol (commercially available) as starting materials. MS (ISP): 436.3, 438.3 (M+H$^+$).

Example 160

Preparation of 3′-(3-Chloro-phenyl)-3,4,5,6-tetrahydro-2H-[1,2′]bipyridinyl-5′-carboxylic Acid ((S)-1-hydroxymethyl-3-methyl-butyl)-amide The title compound was synthesized in analogy to the procedure described for the preparation of Example 43, using 5-bromo-6-chloro-nicotinic acid methyl ester, pyrrolidine (commercially available), 3-chlorophenyl-boronic acid (commercially available) and (S)-(+)-leucinol (commercially available) as starting materials. MS (ISP): 416.4 (M+H$^+$).

Example 161

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 μl/L of b-mercaptoethanol, RPMI-1640 medium. Cells are washed once with RPMI-1640 and loaded with RPMI-1640 medium containing 2% FCS, 50 μg/ml acetylated LDL, and 10 μCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 μg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and EC$_{50}$ values were determined.

The compounds of the present invention exhibit EC$_{50}$ values in a range of 0.01 μM to 100 μM in the cholesterol efflux assay. Preferably, the compounds of the present invention have EC$_{50}$ values in a range of 0.01 μM to 10.0 μM; more preferably 0.01 μM to 1 μM.

Example 162

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example 163

Capsules containing the following ingredients can be manufactured in a conventional manner:

| Ingredients | Per capsule |
| --- | --- |
| Compound of formula (I) | 25.0 mg |
| Lactose | 150.0 mg |

-continued

| Ingredients | Per capsule |
|---|---|
| Maize starch | 20.0 mg |
| Talc | 5.0 mg |

The components are sieved and mixed and filled into capsules of size 2.

Example 164

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of the formula:

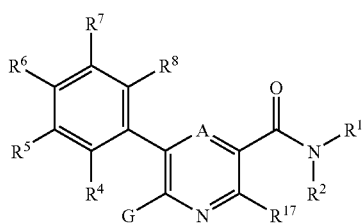

I or a pharmaceutically acceptable salt thereof, wherein:
A is CH;
$R^2$ is hydrogen and $R^1$ is selected from the group consisting of:
 (a) cycloalkyl, which is optionally substituted by hydroxy, lower hydroxyalkyl or lower alkoxy,
 (b) 1-hydroxy-2-indanyl,
 (c) lower hydroxyalkyl,
 (d) lower hydroxyhalogenalkyl,
 (e) lower hydroxyalkoxyalkyl,
 (f) —$CH_2$—$CR^9R^{10}$-cycloalkyl, wherein $R^9$ is hydrogen or lower alkyl; and wherein $R^{10}$ is hydrogen, hydroxy or lower alkoxy; and
 (g) —$CR^{11}R^{12}$—$COOR^{13}$; wherein $R^{11}$ and $R^{12}$ independently from each other are hydrogen or lower alkyl; and wherein $R^{13}$ is lower alkyl;
or alternatively, $R^1$ and $R^2$ together with the nitrogen atom to which they are attached form a morpholinyl ring;
G is a group selected from the group consisting of:
 (a) —X—$R^3$, wherein X is O or $NR^{14}$, wherein $R^{14}$ is selected from the group consisting of hydrogen, lower alkyl and lower hydroxyalkyl; and $R^3$ is lower cycloalkylalkyl,
 (b) —C≡C—$R^{15}$, wherein $R^{15}$ is selected from the group consisting of lower alkoxyalkyl, cycloalkyl and furanyl substituted by halogen; and
 (c) —$CH_2$—$CH_2$—$R^{16}$, wherein $R^{16}$ is selected from the group consisting of:
  (1) a cycloalkyl which is optionally substituted by hydroxy or lower alkoxy,
  (2) a heteroaryl which is pyridyl or imidazolyl, which is optionally substituted by lower alkyl or halogen, and
  (3) lower alkylaminocarbonyl;
$R^4$ and $R^8$ independently from each other are hydrogen or halogen;
$R^5$ and $R^7$ independently from each other are selected from the group consisting of hydrogen, lower alkyl, lower alkoxy, halogen, lower halogenalkyl, lower halogenalkoxy and cyano;
$R^6$ is selected from the group consisting of hydrogen, lower alkoxy, halogen, lower halogenalkyl, lower halogenalkoxy and cyano; and
$R^{17}$ is lower halogenalkyl.

2. A compound of claim 1, wherein X is O.

3. A compound of claim 1, wherein $R^1$ is cycloalkyl substituted by hydroxy.

4. A compound of claim 1, wherein $R^1$ is —$CH_2$—$CR^9R^{10}$-cycloalkyl and wherein $R^9$ is hydrogen and $R^{10}$ is hydroxy.

5. A compound of claim 1, wherein $R^6$ is halogen or lower halogenalkyl and $R^4$, $R^5$, $R^7$ and $R^8$ are hydrogen.

6. A compound of claim 1, wherein:
$R^1$ is cycloalkyl which is substituted by hydroxy, or —$CH_2$—$CR^9R^{10}$-cycloalkyl;
$R^9$ is hydrogen or lower alkyl;
$R^{10}$ is hydrogen, hydroxy or lower alkoxy;
$R^2$ is hydrogen;
X is O;
$R^4$, $R^5$, $R^7$ and $R^8$ are hydrogen; and
$R^6$ is halogen.

7. A compound of claim 1 which is 5-(4-chloro-phenyl)-6-cyclopropylmethoxy-N-((1R,2R)-2-hydroxy-cyclohexyl)-2-trifluoromethyl-nicotinamide or a pharmaceutically acceptable salt thereof.

8. A pharmaceutical composition, comprising a therapeutically effective amount of a compound according to claim 1 and a pharmaceutically acceptable carrier.

* * * * *